US007705120B2

(12) United States Patent
Lillie et al.

(10) Patent No.: US 7,705,120 B2
(45) Date of Patent: Apr. 27, 2010

(54) COMPOSITIONS, KITS, AND METHODS FOR IDENTIFICATION, ASSESSMENT, PREVENTION, AND THERAPY OF BREAST CANCER

(75) Inventors: James Lillie, Westin, MA (US); Manjula Gannavarapu, Acton, MA (US); Karen Glatt, Natick, MA (US); Sebastian Hoersch, Arlington, MA (US); Shubhangi Kamatkar, Newton, MA (US); Maureen Mertens, Hattersley, Stow, MA (US); John E. Monahan, Walpole, MA (US); Vickesh Myer, Harvard, MA (US); Youzhen Wang, Newton, MA (US); Yongyao Xu, Belmont, MA (US); Xumei Zhao, Wayland, MA (US); Rachel E. Meyers, Newton, MA (US); Robert C. Bast, Jr., Houston, TX (US); Gabriel N. Hortobagyi, Houston, TX (US); Lajos Pusztai, Bellaire, TX (US)

(73) Assignees: Millennium Pharmaceuticals, Inc., Cambridge, MA (US); Board of Regents, University of Texas System, Austin, TX (US)

( * ) Notice: Subject to any disclaimer, the term of this patent is extended or adjusted under 35 U.S.C. 154(b) by 783 days.

(21) Appl. No.: 10/177,293

(22) Filed: Jun. 21, 2002

(65) Prior Publication Data
US 2003/0124128 A1 Jul. 3, 2003

Related U.S. Application Data

(60) Provisional application No. 60/299,887, filed on Jun. 21, 2001, now abandoned, provisional application No. 60/301,572, filed on Jun. 27, 2001, now abandoned, provisional application No. 60/306,501, filed on Jul. 18, 2001, now abandoned, provisional application No. 60/325,002, filed on Sep. 25, 2001, now abandoned, provisional application No. 60/362,585, filed on Mar. 5, 2002, now abandoned, provisional application No. 60/380,391, filed on May 14, 2002, now abandoned.

(51) Int. Cl.
C07K 1/00 (2006.01)
C07K 14/00 (2006.01)
C07K 17/00 (2006.01)
C07H 1/00 (2006.01)
C07H 5/00 (2006.01)
C07H 21/00 (2006.01)
C08B 37/00 (2006.01)

(52) U.S. Cl. .............. 530/350; 536/1.11; 536/18.7; 536/23.1; 536/23.4; 536/23.5

(58) Field of Classification Search ........... 530/350; 536/1.11, 18.7, 23.1, 23.4, 23.5
See application file for complete search history.

(56) References Cited

U.S. PATENT DOCUMENTS

| 6,844,325 B2 * | 1/2005 | Jiang et al. ............ 514/44 |
| 2002/0076735 A1 | 6/2002 | Williams et al. |
| 2002/0137160 A1 | 9/2002 | Byatt et al. |
| 2002/0155438 A1 | 10/2002 | Simpson et al. |
| 2002/0155447 A1 | 10/2002 | Zauderer et al. |

FOREIGN PATENT DOCUMENTS

| CN | 1363589 | 1/2001 |
| EP | 1033401 A2 | 9/2000 |
| WO | WO-94/19335 A1 | 9/1994 |
| WO | WO-95/14772 A1 | 6/1995 |
| WO | WO-98/23731 A2 | 6/1998 |
| WO | WO-00/55350 A1 | 9/2000 |
| WO | WO-01/40269 A2 | 6/2001 |
| WO | WO-01/60860 A2 | 8/2001 |
| WO | WO-01/74859 A2 | 10/2001 |
| WO | WO-01/78768 A2 | 10/2001 |
| WO | WO-02/00677 A1 | 1/2002 |
| WO | WO-02/16369 A2 | 2/2002 |
| WO | WO-02/28827 A1 | 4/2002 |
| WO | WO-02/31111 A2 | 4/2002 |
| WO | WO-02/053714 A2 | 7/2002 |
| WO | WO-02/060317 A2 | 8/2002 |
| WO | WO-03/004467 A2 | 1/2003 |

OTHER PUBLICATIONS

Brennan et al (Journal of Autoimmunity, 1989, vol. 2 suppl., pp. 177-186).*
Zimmer (Cell Motility and the Cytoskeleton, 1991, vol. 20, pp. 325-337).*
Eriksson et al (Diabetologia, 1992, vol. 35, pp. 143-147).*
Hell et al (Laboratory Investigation, 1995, vol. 73, pp. 492-496).*

(Continued)

Primary Examiner—Alana M Harris
(74) Attorney, Agent, or Firm—McCarter & English, LLP; Maria Laccotripe Zacharakis; Marcie B. Clarke

(57) ABSTRACT

The invention relates to newly discovered nucleic acid molecules and proteins associated with breast cancer. Compositions, kits, and methods for detecting, characterizing, preventing, and treating human breast cancers are provided.

24 Claims, No Drawings

OTHER PUBLICATIONS

Powell et al (Pharmacogenesis, 1998, vol. 8, pp. 411-421).*
Carrere et al (Gut, 1999, vol. 44, pp. 545-551).*
Vallejo et al (Biochimie, 2000, vol. 82, pp. 1129-1133).*
Guo et al (Journal of Pharmacology and Experimental Therapeutics, 2002, vol. 300, pp. 206-212).*
Jang et al (Clinical and Experimental Metastasis, 1997, vol. 15, pp. 469-483).*
Greenbaum et al. (Genome Biology, 2003, vol. 4, Issue 9, pp. 117.1-117.8).*
Bowie et al (Science, 1990, 257:1306-1310).*
Burgess et al ( J of Cell Bio. 111:2129-2138, 1990).*
Lazar et al (Molecular and Cellular Biology, 1988, 8:1247-1252).*
GenBank AC AAK27326, Jager et al., "Identification of a tissue-specific putative transcription factor in breast tissue by serological screening of a breast cancer library," *Cancer Res.*, vol. 61(5):2055-2061 (Mar. 28, 2001).
Jäger, Dirk et al., "Identification of a Tissue-specific Putative Transcription in Breast Tissue by Serological Screening of a Breast Cancer Library," *Cancer Research*, vol. 61:2055-2061 (2001).

* cited by examiner

COMPOSITIONS, KITS, AND METHODS FOR IDENTIFICATION, ASSESSMENT, PREVENTION, AND THERAPY OF BREAST CANCER

RELATED APPLICATIONS

This application claims benefit to U.S. provisional patent application Ser. No. 60/299,887, filed on Jun. 21, 2001, now abandoned, and to U.S. provisional patent application Ser. No. 60/301,572, filed on Jun. 27, 2001, now abandoned. The present application also claims benefit to U.S. provisional patent application Ser. No. 60/306,501, filed on Jul. 18, 2001, now abandoned, to U.S. provisional patent application Ser. No. 60/325,002, filed Sep. 25, 2001, now abandoned, to U.S. provisional patent application Ser. No. 60/362,585, filed Mar. 5, 2002, now abandoned, and to from U.S. provisional patent application Ser. No. 60/380,391, filed May 14, 2002, now abandoned. All of the above applications are expressly incorporated by reference.

FIELD OF THE INVENTION

The field of the invention is breast cancer, including diagnosis, characterization, management, and therapy of breast cancer.

BACKGROUND OF THE INVENTION

The increased number of cancer cases reported in the United States, and, indeed, around the world, is a major concern. Currently there are only a handful of treatments available for specific types of cancer, and these provide no absolute guarantee of success. In order to be most effective, these treatments require not only an early detection of the malignancy, but a reliable assessment of the severity of the malignancy.

The incidence of breast cancer, a leading cause of death in women, has been gradually increasing in the United States over the last thirty years. In 1997, it was estimated that 181, 000 new cases were reported in the U.S., and that 44,000 people would die of breast cancer (Parker et al, 1997, *CA Cancer J. Clin.* 47:5-27; Chu et al, 1996, *J. Nat. Cancer Inst.* 88:1571-1579). While the pathogenesis of breast cancer is unclear, transformation of normal breast epithelium to a malignant phenotype may be the result of genetic factors, especially in women under 30 (Miki et al., 1994, *Science,* 266:66-71). The discovery and characterization of BRCA1 and BRCA2 has recently expanded our knowledge of genetic factors which can contribute to familial breast cancer. Germline mutations within these two loci are associated with a 50 to 85% lifetime risk of breast and/or ovarian cancer (Casey, 1997, *Curr. Opin. Oncol.* 9:88-93; Marcus et al, 1996, *Cancer* 77:697-709). However, it is likely that other, non-genetic factors also have a significant effect on the etiology of the disease. Regardless of its origin, breast cancer morbidity and mortality increases significantly if it is not detected early in its progression. Thus, considerable effort has focused on the early detection of cellular transformation and tumor formation in breast tissue.

Currently, the principal manner of identifying breast cancer is through detection of the presence of dense tumorous tissue. This may be accomplished to varying degrees of effectiveness by direct examination of the outside of the breast, or through mammography or other X-ray imaging methods (Jatoi, 1999, *Am. J. Surg.* 177:518-524). The latter approach is not without considerable cost, however. Every time a mammogram is taken, the patient incurs a small risk of having a breast tumor induced by the ionizing properties of the radiation used during the test. In addition, the process is expensive and the subjective interpretations of a technician can lead to imprecision, e.g., one study showed major clinical disagreements for about one-third of a set of mammograms that were interpreted individually by a surveyed group of radiologists. Moreover, many women find that undergoing a mammogram is a painful experience. Accordingly, the National Cancer Institute has not recommended mammograms for women under fifty years of age, since this group is not as likely to develop breast cancers as are older women. It is compelling to note, however, that while only about 22% of breast cancers occur in women under fifty, data suggests that breast cancer is more aggressive in pre-menopausal women.

It would therefore be beneficial to provide specific methods and reagents for the diagnosis, staging, prognosis, monitoring, and treatment of diseases associated with breast cancer, or to indicate a predisposition to such for preventative measures.

SUMMARY OF THE INVENTION

The invention relates to cancer markers (hereinafter "markers" or "markers of the inventions"), which are listed in Tables 1-12. The invention provides nucleic acids and proteins that are encoded by or correspond to the markers (hereinafter "marker nucleic acids" and "marker proteins," respectively). Tables 1-12 provide the sequence identifiers of the sequences of such marker nucleic acids and proteins listed in the accompanying Sequence Listing. The invention further provides antibodies, antibody derivatives and antibody fragments which bind specifically with such proteins and/or fragments of the proteins.

Table 1 lists all of the markers of the invention, which are over-expressed in breast cancer cells compared to normal (i.e., non-cancerous) breast cells. Table 2 lists markers identified by transcription profiling using mRNA from 23 invasive ductal carcinoma (IDC) node negative breast tumors with good outcome and16 IDC node negative breast tumors with poor clinical outcome. Table 3 lists markers identified by transcription profiling using mRNA from 16 IDC node negative breast tumors and 19 IDC node positive breast tumors. Table 4 lists markers identified by transcription profiling using mRNA from 25 IDC node negative breast tumors with good outcome and18 IDC node negative breast tumors with poor clinical outcome. Table 5 lists markers particularly useful in screening for the presence of breast cancer ("screening markers"). Table 6 lists markers particularly useful in assessing aggressiveness of breast cancer ("aggressiveness markers"). Table 7 lists markers particularly useful for both screening breast cancer and assessing aggressiveness of breast cancer. Table 8 lists markers whose over-expression correlates with good clinical outcome, i.e., greater than 5 years of disease-free survival. Table 9 lists markers whose over-expression correlates with poor clinical outcome, i.e., less than 3 years of disease-free survival. Table 10 lists newly identified nucleic acid and amino acid sequences. Table 11 lists newly identified nucleic acid sequences. Table 12 lists staging markers whose expression correlates with metastasis to lymph nodes.

Tables 1-12 provide the name of the gene corresponding to the marker ("Gene Name"), the sequence listing identifier of the cDNA sequence of a nucleotide transcript encoded by or corresponding to the marker ("SEQ ID NO (nts)"), the sequence listing identifier of the amino acid sequence of a protein encoded by the nucleotide transcript ("SEQ ID NO (AAs)"), and the location of the protein coding sequence within the cDNA sequence ("CDS").

The invention also relates to various methods, reagents and kits for diagnosing, staging, prognosing, monitoring and treating breast cancer. "Breast cancer" as used herein includes carcinomas, (e.g., carcinoma in situ, invasive carcinoma, metastatic carcinoma) and pre-malignant conditions. In one embodiment, the invention provides a diagnostic method of assessing whether a patient has breast cancer or has higher than normal risk for developing breast cancer, comprising the steps of comparing the level of expression of a marker of the invention in a patient sample and the normal level of expression of the marker in a control, e.g., a sample from a patient without breast cancer. A significantly higher level of expression of the marker in the patient sample, as compared to the normal level, is an indication that the patient is afflicted with breast cancer or has higher than normal risk for developing breast cancer.

The methods of the present invention can be of use in identifying patients having an enhanced risk of developing breast cancer (e.g., patients having a familial history of breast cancer and patients identified as having a mutant oncogene). The methods of the present invention may further be of particular use in evaluating the specific stage of breast cancer, as well as in assessing whether the cancer has metastasized (e.g., metastasis to the lymph nodes). The methods of the present invention are also useful in predicting the clinical outcome for a patient with breast cancer, or for a patient who has undergone therapy to eradicate breast cancer. The methods of the present invention are also be useful in assessing the efficacy of treatment of a breast cancer patient (e.g., the efficacy of chemotherapy).

According to the invention, the markers are selected such that the positive predictive value of the methods of the invention is at least about 10%, preferably about 25%, more preferably about 50% and most preferably about 90%. Also preferred are embodiments of the method wherein the marker is over-expressed by at least five-fold in at least about 15% of stage 0 breast cancer patients, stage I breast cancer patients, stage IIA breast cancer patients, stage IIB breast cancer patients, stage IIIA breast cancer patients, stage IIIB breast cancer patients, stage IV breast cancer patients, grade I breast cancer patients, grade II breast cancer patients, grade III breast cancer patients, malignant breast cancer patients, ductal carcinoma breast cancer patients, and lobular carcinoma breast cancer patients, and all other types of cancers, malignancies and transformations associated with the breast.

In a preferred diagnostic method of assessing whether a patient is afflicted with breast cancer (e.g., new detection ("screening"), detection of recurrence, reflex testing), the method comprises comparing:
 a) the level of expression of a marker listed in Table 1 in a sample from the patient, and
 b) the level of expression of the marker in a control subject not having breast cancer.

A significantly higher level of expression of the marker in the patient sample, as compared to the level in the control subject, is an indication that the patient is afflicted with breast cancer. In one embodiment, the marker is listed in Table 5.

The invention additionally provides a diagnostic method for determining whether a patient has an aggressive breast cancer, the method comprising comparing:
 a) the level of expression of a marker listed in Table 1 in a sample from the patient, and
 b) the level of expression of the marker in a sample from a control subject having an indolent breast tumor or no breast tumor.

A significantly higher level of expression in the patient sample, as compared to the level in the sample from the control subject, is an indication that the patient has an aggressive breast cancer or is likely to develop an aggressive breast tumor. No difference in expression between the patient sample and the control sample, or a significantly lower level of expression in the patient sample, as compared to the control level, indicates that the patient has an indolent breast cancer. In one embodiment, the marker is listed in Table 6.

The invention further provides a diagnostic method for determining whether a patient has breast cancer that has metastasized or is likely to metastasize, the method comprising comparing:
 a) the level of expression of a marker listed in Table 1 in a sample from the patient, and
 b) the level of expression of the marker in a sample from a control subject having a non-metastasized breast tumor or no breast tumor.

A significantly higher level of expression in the patient sample as compared to the level in the sample from the control subject is an indication that the breast cancer has metastasized or is likely to metastasize. In one embodiment, the marker is selected from the markers in Tables 6 and 12.

In another embodiment, the present invention includes a method for determining whether a patient has breast cancer that has metastasized to lymph nodes, or is likely to metastasize to lymph nodes, the method comprising comparing:
 a) the level of expression of a marker listed in Table 1 in a sample from the patient, and
 b) the level of expression in a sample from a control subject having a non-metastasized breast tumor or no breast tumor.

A significantly higher level of expression in the patient sample as compared to the level in the sample from the control subject, is an indication that the patient is afflicted with metastatic breast cancer that has metastasized to lymph nodes, or is likely to metastasize to lymph nodes. In one embodiment, the marker is selected from the markers of Table 12.

The invention also provides a method for predicting the clinical outcome of a breast cancer patient, the method comprising comparing:
 a) the level of expression of a marker listed in Table 1 in a sample from the patient, and
 b) the level of expression of the marker in a sample from a control subject having a good clinical outcome (i.e., a former breast cancer patient having greater than five years of disease-free survival level).

A significantly higher level of expression in the patient sample as compared to the expression level in the sample from the control subject is an indication that the patient has a poor clinical outcome, i.e. less than 3 years of disease-free survival. In one embodiment, the marker is selected from the markers of Table 9.

The invention also provides methods for assessing the efficacy of a therapy for inhibiting breast cancer in a patient. Such methods comprise comparing:
 a) expression of a marker of the invention in a first sample obtained from the patient prior to providing at least a portion of the therapy to the patient, and
 b) expression of the marker in a second sample obtained from the patient following provision of the portion of the therapy.

A significantly lower level of expression of the marker in the second sample relative to that in the first sample is an indication that the therapy is efficacious for inhibiting breast cancer in the patient.

It will be appreciated that in these methods the "therapy" may be any therapy for treating breast cancer including, but not limited to, chemotherapy, radiation therapy, surgical removal of tumor tissue, gene therapy and biologic therapy such as the administering of antibodies and chemokines. Thus, the methods of the invention may be used to evaluate a patient before, during and after therapy, for example, to evaluate the reduction in tumor burden.

In a preferred embodiment, the methods are directed to therapy using a chemical or biologic agent. These methods comprise comparing:
 a) expression of a marker of the invention in a first sample obtained from the patient and maintained in the presence of the chemical or biologic agent, and
 b) expression of the marker in a second sample obtained from the patient and maintained in the absence of the agent.

A significantly lower level of expression of the marker in the second sample relative to that in the first sample is an indication that the agent is efficacious for inhibiting breast cancer, in the patient. In one embodiment, the first and second samples can be portions of a single sample obtained from the patient or portions of pooled samples obtained from the patient.

The invention additionally provides a monitoring method for assessing the progression of breast cancer in a patient, the method comprising:
 a) detecting in a sample from the patient at a first time point, the expression of a marker of the invention;
 b) repeating step a) at a subsequent time point in time; and
 c) comparing the level of expression detected in steps a) and b), and therefrom monitoring the progression of breast cancer in the patient.

A significantly higher level of expression of the marker in the sample at the subsequent time point from that of the sample at the first time point is an indication that the breast cancer has progressed in the patient, whereas a significantly lower level of expression is an indication that the breast cancer has regressed.

The invention moreover provides a test method for selecting a composition for inhibiting breast cancer in a patient. This method comprises the steps of:
 a) obtaining a sample comprising cancer cells from the patient;
 b) separately maintaining aliquots of the sample in the presence of a plurality of test compositions;
 c) comparing expression of a marker of the invention in each of the aliquots; and
 d) selecting one of the test compositions which significantly reduces the level of expression of the marker in the aliquot containing that test composition, relative to the levels of expression of the marker in the presence of the other test compositions.

The invention additionally provides a test method of assessing the breast carcinogenic potential of a compound. This method comprises the steps of:
 a) maintaining separate aliquots of breast cells in the presence and absence of the compound; and
 b) comparing expression of a marker of the invention in each of the aliquots.

A significantly higher level of expression of the marker in the aliquot maintained in the presence of the compound, relative to that of the aliquot maintained in the absence of the compound, is an indication that the compound possesses breast carcinogenic potential.

In addition, the invention further provides a method of inhibiting breast cancer in a patient. This method comprises the steps of:
 a) obtaining a sample comprising cancer cells from the patient;
 b) separately maintaining aliquots of the sample in the presence of a plurality of compositions;
 c) comparing expression of a marker of the invention in each of the aliquots; and
 d) administering to the patient at least one of the compositions which significantly lowers the level of expression of the marker in the aliquot containing that composition, relative to the levels of expression of the marker in the presence of the other compositions.

In the aforementioned methods, the samples or patient samples comprise cells obtained from the patient, e.g., a lump biopsy, body fluids including blood fluids, lymph and cystic fluids, as well as nipple aspirates. In a further embodiment, the patient sample is in vivo.

According to the invention, the level of expression of a marker of the invention in a sample can be assessed, for example, by detecting the presence in the sample of:
 the corresponding marker protein (e.g., a protein having one of the sequences of SEQ ID NO (AAs)) or a fragment of the protein (e.g. by using a reagent, such as an antibody, an antibody derivative, an antibody fragment or single-chain antibody, which binds specifically with the protein or protein fragment)
 the corresponding marker nucleic acid (e.g. a nucleotide transcript having one of the sequences of the SEQ ID NO (nts)), or a complement thereof), or a fragment of the nucleic acid (e.g. by contacting transcribed polynucleotides obtained from the sample with a substrate having affixed thereto one or more nucleic acids having the entire or a segment of the sequence of any of the SEQ ID NO (nts)), or a complement thereof)
 a metabolite which is produced directly (i.e., catalyzed) or indirectly by the corresponding marker protein.

According to the invention, any of the aforementioned methods may be performed using a plurality (e.g. 2, 3, 5, or 10 or more) of breast cancer markers, including breast cancer markers known in the art. In such methods, the level of expression in the sample of each of a plurality of markers, at least one of which is a marker of the invention, is compared with the normal level of expression of each of the plurality of markers in samples of the same type obtained from control humans not afflicted with breast cancer. A significantly altered (i.e., increased or decreased as specified in the above-described methods using a single marker) level of expression in the sample of one or more markers of the invention, or some combination thereof, relative to that marker's corresponding normal or control level, is an indication that the patient is afflicted with breast cancer. For all of the aforementioned methods, the marker(s) are preferably selected such that the positive predictive value of the method is at least about 10%.

In a further aspect, the invention provides an antibody, an antibody derivative, or an antibody fragment, which binds specifically with a marker protein (e.g., a protein having the sequence of any of the SEQ ID NO (AAs)) or a fragment of the protein. The invention also provides methods for making such antibody, antibody derivative, and antibody fragment. Such methods may comprise immunizing a mammal with a protein or peptide comprising the entirety, or a segment of 10 or more amino acids, of a marker protein (e.g., a protein having the sequence of any of the SEQ ID NO (AAs)), wherein the protein or peptide may be obtained from a cell or by chemical synthesis. The methods of the invention also encompass producing monoclonal and single-chain antibodies, which would further comprise isolating splenocytes from the immunized mammal, fusing the isolated splenocytes with an immortalized cell line to form hybridomas, and screening individual hybridomas for those that produce an antibody that binds specifically with a marker protein or a fragment of the protein.

In another aspect, the invention relates to various diagnostic and test kits. In one embodiment, the invention provides a kit for assessing whether a patient is afflicted with breast cancer. The kit comprises a reagent for assessing expression of a marker of the invention. In another embodiment, the invention provides a kit for assessing the suitability of a chemical or biologic agent for inhibiting breast cancer in a patient. Such a kit comprises a reagent for assessing expression of a marker of the invention, and may also comprise one or more of such agents. In a further embodiment, the invention provides kits for assessing the presence of breast cancer cells or treating breast cancers. Such kits comprise an antibody, an antibody derivative, or an antibody fragment, which binds specifically with a marker protein, or a fragment of the protein. Such kits may also comprise a plurality of antibodies, antibody derivatives, or antibody fragments wherein the plurality of such antibody agents binds specifically with a marker protein, or a fragment of the protein.

In an additional embodiment, the invention also provides a kit for assessing the presence of breast cancer cells, wherein the kit comprises a nucleic acid probe that binds specifically with a marker nucleic acid or a fragment of the nucleic acid. The kit may also comprise a plurality of probes, wherein each of the probes binds specifically with a marker nucleic acid, or a fragment of the nucleic acid.

In a further aspect, the invention relates to methods for treating a patient afflicted with breast cancer or at risk of developing breast cancer. Such methods may comprise reducing the expression and/or interfering with the biological function of a marker of the invention. In one embodiment, the method comprises providing to the patient an antisense oligonucleotide or polynucleotide complementary to a marker nucleic acid, or a segment thereof. For example, an antisense polynucleotide may be provided to the patient through the delivery of a vector that expresses an anti-sense polynucleotide of a marker nucleic acid or a fragment thereof. In another embodiment, the method comprises providing to the patient an antibody, an antibody derivative, or antibody fragment, which binds specifically with a marker protein or a fragment of the protein. In a preferred embodiment, the antibody, antibody derivative or antibody fragment binds specifically with a protein having the sequence of a SEQ ID NO (AAs), or a fragment of the protein.

It will be appreciated that the methods and kits of the present invention may also include known cancer markers including known breast cancer markers. It will further be appreciated that the methods and kits may be used to identify cancers other than breast cancer.

DETAILED DESCRIPTION OF THE INVENTION

The invention relates to newly discovered breast cancer markers associated with the cancerous state of breast cells. It has been discovered that the higher than normal level of expression of any of these markers or combination of these markers correlates with the presence of breast cancer in a patient. Methods are provided for detecting the presence of breast cancer in a sample, the absence of breast cancer in a sample, the stage of breast cancer, assessing whether a breast cancer has metastasized, predicting the likely clinical outcome of a breast cancer patient, and with other characteristics of breast cancer that are relevant to prevention, diagnosis, characterization, and therapy of breast cancer in a patient. Methods of treating breast cancer are also provided.

Table 1 lists all of the markers of the invention, which are over-expressed in breast cancer cells compared to normal (i.e., non-cancerous) breast cells. Table 2 lists markers identified by transcription profiling using mRNA from 23 IDC node negative breast tumors with good outcome and 16 IDC node negative breast tumors with poor clinical outcome. Table 3 lists markers identified by transcription profiling using mRNA from 16 IDC node negative breast tumors and 19 IDC node positive breast tumors. Table 4 lists markers identified by transcription profiling using mRNA from 25 IDC node negative breast tumors with good outcome and 18 IDC node negative breast tumors with poor clinical outcome. Table 5 lists markers particularly useful in screening for the presence of breast cancer ("screening markers"). Table 6 lists markers particularly useful in assessing aggressiveness of breast cancer ("aggressiveness markers"). Table 7 lists markers particularly useful for both screening breast cancer and assessing aggressiveness of breast cancer. Table 8 lists markers whose over-expression correlates with good clinical outcome, i.e., greater than 5 years of disease-free survival. Table 9 lists markers whose over-expression correlates with poor clinical outcome, i.e., less than 3 years of disease-free survival. Table 10 lists newly identified nucleic acid and amino acid sequences. Table 1 lists newly identified nucleic acid sequences. Table 12 lists staging markers whose expression correlates with metastasis to lymph nodes.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

A "marker" is a gene whose altered level of expression in a tissue or cell from its expression level in normal or healthy tissue or cell is associated with a disease state, such as cancer. A "marker nucleic acid" is a nucleic acid (e.g., mRNA, cDNA) encoded by or corresponding to a marker of the invention. Such marker nucleic acids include DNA (e.g., cDNA) comprising the entire or a partial sequence of any of the SEQ ID NO (nts) or the complement of such a sequence. The marker nucleic acids also include RNA comprising the entire or a partial sequence of any SEQ ID NO (nts) or the complement of such a sequence, wherein all thymidine residues are replaced with uridine residues. A "marker protein" is a protein encoded by or corresponding to a marker of the invention. A marker protein comprises the entire or a partial sequence of any of the SEQ ID NO (AAs). The terms "protein" and "polypeptide" are used interchangeably.

The term "probe" refers to any molecule which is capable of selectively binding to a specifically intended target molecule, for example, a nucleotide transcript or protein encoded by or corresponding to a marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

A "breast-associated" body fluid is a fluid which, when in the body of a patient, contacts or passes through breast cells or into which cells, nucleic acids or proteins shed from breast cells are capable of passing. Exemplary breast-associated body fluids include blood fluids, lymph, cystic fluid, and nipple aspirates.

The "normal" level of expression of a marker is the level of expression of the marker in breast cells of a human subject or patient not afflicted with breast cancer.

An "over-expression" or "significantly higher level of expression" of a marker refers to an expression level in a test sample that is greater than the standard error of the assay employed to assess expression, and is preferably at least twice, and more preferably three, four, five or ten times the expression level of the marker in a control sample (e.g., sample from a healthy subjects not having the marker associated disease) and preferably, the average expression level of the marker in several control samples.

A "significantly lower level of expression" of a marker refers to an expression level in a test sample that is at least twice, and more preferably three, four, five or ten times lower than the expression level of the marker in a control sample (e.g., sample from a healthy subjects not having the marker associated disease) and preferably, the average expression level of the marker in several control samples.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue-specific manner.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a marker of the invention and normal post-transcriptional processing (e.g. splicing), if any, of the RNA transcript, and reverse transcription of the RNA transcript.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

A molecule is "fixed" or "affixed" to a substrate if it is covalently or non-covalently associated with the substrate such the substrate can be rinsed with a fluid (e.g. standard saline citrate, pH 7.4) without a substantial fraction of the molecule dissociating from the substrate.

As used herein, a "naturally-occurring" nucleic acid molecule refers to an RNA or DNA molecule having a nucleotide sequence that occurs in an organism found in nature.

A cancer is "inhibited" if at least one symptom of the cancer is alleviated, terminated, slowed, or prevented. As used herein, breast cancer is also "inhibited" if recurrence or metastasis of the cancer is reduced, slowed, delayed, or prevented.

A kit is any manufacture (e.g. a package or container) comprising at least one reagent, e.g. a probe, for specifically detecting the expression of a marker of the invention. The kit may be promoted, distributed, or sold as a unit for performing the methods of the present invention.

"Proteins of the invention" encompass marker proteins and their fragments; variant marker proteins and their fragments; peptides and polypeptides comprising an at least 15 amino acid segment of a marker or variant marker protein; and fusion proteins comprising a marker or variant marker protein, or an at least 15 amino acid segment of a marker or variant marker protein.

Unless otherwise specified herewithin, the terms "antibody" and "antibodies" broadly encompass naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

Description

The present invention is based, in part, on newly identified markers which are over-expressed in breast cancer cells as compared to their expression in normal (i.e. non-cancerous) breast cells. The enhanced expression of one or more of these markers in breast cells is herein correlated with the cancerous state of the tissue. An enhanced expression of some of these markers is also correlated with the stage, nodal status and clinical outcome of the patient. The invention provides compositions, kits, and methods for assessing the cancerous state of breast cells (e.g. cells obtained from a human, cultured human cells, archived or preserved human cells and in vivo cells) as well as treating patients afflicted with breast cancer.

The compositions, kits, and methods of the invention have the following uses, among others:

1) assessing whether a patient is afflicted with breast cancer;
2) assessing the stage of breast cancer in a human patient;
3) predicting the clinical outcome of a breast cancer patient;
4) assessing the grade of breast cancer in a patient;
5) assessing the benign or malignant nature of breast cancer in a patient;
6) assessing the metastatic potential of breast cancer in a patient;
7) determining if breast cancer has metastasized to lymph nodes;
8) assessing the histological type of neoplasm associated with breast cancer in a patient;
9) making antibodies, antibody fragments or antibody derivatives that are useful for treating breast cancer and/ or assessing whether a patient is afflicted with breast cancer;
10) assessing the presence of breast cancer cells;
11) assessing the efficacy of one or more test compounds for inhibiting breast cancer in a patient;
12) assessing the efficacy of a therapy for inhibiting breast cancer in a patient;
13) monitoring the progression of breast cancer in a patient;
14) selecting a composition or therapy for inhibiting breast cancer in a patient;
15) treating a patient afflicted with breast cancer;
16) inhibiting breast cancer in a patient;
17) assessing the breast carcinogenic potential of a test compound; and
18) preventing the onset of breast cancer in a patient at risk for developing breast cancer.

The invention thus includes a method of assessing whether a patient is afflicted with breast cancer. This method comprises comparing the level of expression of a marker of the invention (listed in Table 1) in a patient sample and the normal level of expression of the marker in a control, e.g., a non-breast cancer sample. A significantly higher level of expression of the marker in the patient sample as compared to the normal level is an indication that the patient is afflicted with breast cancer.

Gene delivery vehicles, host cells and compositions (all described herein) containing nucleic acids comprising the entirety, or a segment of 15 or more nucleotides, of any of the sequences of SEQ ID NO (nts) or the complement of such sequences, and polypeptides comprising the entirety, or a segment of 10 or more amino acids, of any of the sequences of SEQ ID NO (AAs) are also provided by this invention.

As described herein, breast cancer in patients is associated with an increased level of expression of one or more markers of the invention. While, as discussed above, some of these changes in expression level result from occurrence of the breast cancer, others of these changes induce, maintain, and promote the cancerous state of breast cancer cells. Thus, breast cancer characterized by an increase in the level of expression of one or more markers of the invention can be inhibited by reducing and/or interfering with the expression of the markers and/or function of the proteins encoded by those markers.

Expression of a marker of the invention can be inhibited in a number of ways generally known in the art. For example, an antisense oligonucleotide can be provided to the breast cancer cells in order to inhibit transcription, translation, or both, of the marker(s). Alternately, a polynucleotide encoding an antibody, an antibody derivative, or an antibody fragment which specifically binds a marker protein, and operably linked with an appropriate promoter/regulator region, can be provided to the cell in order to generate intracellular antibodies which will inhibit the function or activity of the protein. The expression and/or function of a marker may also be inhibited by treating the breast cancer cell with an antibody, antibody derivative or antibody fragment that specifically binds a marker protein. Using the methods described herein, a variety of molecules, particularly including molecules sufficiently small that they are able to cross the cell membrane, can be screened in order to identify molecules which inhibit expression of a marker or inhibit the function of a marker protein. The compound so identified can be provided to the patient in order to inhibit breast cancer cells of the patient.

Any marker or combination of markers of the invention, as well as any known markers in combination with the markers of the invention, may be used in the compositions, kits, and methods of the present invention. In general, it is preferable to use markers for which the difference between the level of expression of the marker in breast cancer cells and the level of expression of the same marker in normal breast cells is as great as possible. Although this difference can be as small as the limit of detection of the method for assessing expression of the marker, it is preferred that the difference be at least greater than the standard error of the assessment method, and preferably a difference of at least 2-, 3-, 4-, 5-, 6-, 7-, 8-, 9-, 10-, 15-, 20-, 25-, 100-, 500-, 1000-fold or greater than the level of expression of the same marker in normal breast tissue.

It is recognized that certain marker proteins are secreted from breast cells (i.e. one or both of normal and cancerous cells) to the extracellular space surrounding the cells. These markers are preferably used in certain embodiments of the compositions, kits, and methods of the invention, owing to the fact that the such marker proteins can be detected in a breast-associated body fluid sample, which may be more easily collected from a human patient than a tissue biopsy sample. In addition, preferred in vivo techniques for detection of a marker protein include introducing into a subject a labeled antibody directed against the protein. For example, the antibody can be labeled with a radioactive marker whose presence and location in a subject can be detected by standard imaging techniques.

It is a simple matter for the skilled artisan to determine whether any particular marker protein is a secreted protein. In order to make this determination, the marker protein is expressed in, for example, a mammalian cell, preferably a human breast cell line, extracellular fluid is collected, and the presence or absence of the protein in the extracellular fluid is assessed (e.g. using a labeled antibody which binds specifically with the protein).

The following is an example of a method which can be used to detect secretion of a protein. About $8 \times 10^5$ 293T cells are incubated at 37° C. in wells containing growth medium (Dulbecco's modified Eagle's medium {DMEM} supplemented with 10% fetal bovine serum) under a 5% (v/v) $CO_2$, 95% air atmosphere to about 60-70% confluence. The cells are then transfected using a standard transfection mixture comprising 2 micrograms of DNA comprising an expression vector encoding the protein and 10 microliters of LipofectAMINE (GIBCO/BRL Catalog no. 18342-012) per well. The transfection mixture is maintained for about 5 hours, and then replaced with fresh growth medium and maintained in an air atmosphere. Each well is gently rinsed twice with DMEM which does not contain methionine or cysteine (DMEM-MC; ICN Catalog no. 16-424-54). About 1 milliliter of DMEM-MC and about 50 microcuries of Trans-S™ reagent (ICN Catalog no. 51006) are added to each well. The wells are maintained under the 5% $CO_2$ atmosphere described above and incubated at 37° C. for a selected period. Following incubation, 150 microliters of conditioned medium is removed and centrifuged to remove floating cells and debris. The presence of the protein in the supernatant is an indication that the protein is secreted.

It will be appreciated that patient samples containing breast cells may be used in the methods of the present invention. In these embodiments, the level of expression of the marker can be assessed by assessing the amount (e.g. absolute amount or concentration) of the marker in a breast cell sample, e.g., breast biopsies obtained from a patient. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample. Likewise, breast biopsies may also be subjected to post-collection preparative and storage techniques, e.g., fixation.

The compositions, kits, and methods of the invention can be used to detect expression of marker proteins having at least one portion which is displayed on the surface of cells which express it. It is a simple matter for the skilled artisan to determine whether a marker protein, or a portion thereof, is exposed on the cell surface. For example, immunological methods may be used to detect such proteins on whole cells, or well known computer-based sequence analysis methods may be used to predict the presence of at least one extracellular domain (i.e. including both secreted proteins and proteins having at least one cell-surface domain). Expression of a marker protein having at least one portion which is displayed on the surface of a cell which expresses it may be detected without necessarily lysing the cell (e.g. using a labeled antibody which binds specifically with a cell-surface domain of the protein).

Expression of a marker of the invention may be assessed by any of a wide variety of well known methods for detecting expression of a transcribed nucleic acid or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In a preferred embodiment, expression of a marker is assessed using an antibody (e.g. a radio-labeled, chromophore-labeled, fluorophore-labeled, or enzyme-labeled antibody), an antibody derivative (e.g. an antibody conjugated with a substrate or with the protein or ligand of a protein-ligand pair {e.g. biotin-streptavidin}), or an antibody fragment (e.g. a single-chain antibody, an isolated antibody hypervariable domain, etc.) which binds specifically with a marker protein or fragment thereof, including a marker protein which has undergone all or a portion of its normal post-translational modification.

In another preferred embodiment, expression of a marker is assessed by preparing mRNA/cDNA (i.e. a transcribed polynucleotide) from cells in a patient sample, and by hybridizing the mRNA/cDNA with a reference polynucleotide which is a complement of a marker nucleic acid, or a fragment thereof. cDNA can, optionally, be amplified using any of a variety of polymerase chain reaction methods prior to hybridization with the reference polynucleotide; preferably, it is not amplified. Expression of one or more markers can likewise be detected using quantitative PCR to assess the level of expression of the marker(s). Alternatively, any of the many known methods of detecting mutations or variants (e.g. single nucleotide polymorphisms, deletions, etc.) of a marker of the invention may be used to detect occurrence of a marker in a patient.

In a related embodiment, a mixture of transcribed polynucleotides obtained from the sample is contacted with a substrate having fixed thereto a polynucleotide complementary to or homologous with at least a portion (e.g. at least 7, 10, 15, 20, 25, 30, 40, 50, 100, 500, or more nucleotide residues) of a marker nucleic acid. If polynucleotides complementary to or homologous with are differentially detectable on the substrate (e.g. detectable using different chromophores or fluorophores, or fixed to different selected positions), then the levels of expression of a plurality of markers can be assessed simultaneously using a single substrate (e.g. a "gene chip" microarray of polynucleotides fixed at selected positions). When a method of assessing marker expression is used which involves hybridization of one nucleic acid with another, it is preferred that the hybridization be performed under stringent hybridization conditions.

Because the compositions, kits, and methods of the invention rely on detection of a difference in expression levels of one or more markers of the invention, it is preferable that the level of expression of the marker is significantly greater than the minimum detection limit of the method used to assess expression in at least one of normal breast cells and cancerous breast cells.

It is understood that by routine screening of additional patient samples using one or more of the markers of the invention, it will be realized that certain of the markers are over-expressed in cancers of various types, including specific breast cancers, as well as other cancers such as lung cancer, ovarian cancer, etc. For example, it will be confirmed that some of the markers of the invention are over-expressed in most (i.e. 50% or more) or substantially all (i.e. 80% or more) of breast cancer. Furthermore, it will be confirmed that certain of the markers of the invention are associated with breast cancer of various stages (i.e. stage 0, I, II, II, and IV breast cancers, as well as subclassifications IIA, IIB, IIIA, and IIIB, using the FIGO Stage Grouping system for primary carcinoma of the breast; (see Breast, In: *American Joint Committee on Cancer: AJCC Cancer Staging Manual*. Lippincott-Raven Publishers, 5th ed., 1997, pp. 171-180), of various histologic subtypes (e.g. serous, mucinous, endometroid, and clear cell subtypes, as well as subclassifications and alternate classifications adenocarcinoma, papillary adenocarcinoma, papillary cystadenocarcinoma, surface papillary carcinoma, malignant adenofibroma, cystadenofibroma, adenocarcinoma, cystadenocarcinoma, adenoacanthoma, endometrioid stromal sarcoma, mesodermal (Mullerian) mixed tumor, mesonephroid tumor, malignant carcinoma, Brenner tumor, mixed epithelial tumor, and undifferentiated carcinoma, using the WHO/FIGO system for classification of malignant breast tumors; Scully, *Atlas of Tumor Pathology*, 3d series, Washington D.C.), and various grades (i.e. grade I {well differentiated}, grade II {moderately well differentiated}, and grade III {poorly differentiated from surrounding normal tissue})). In addition, as a greater number of patient samples are assessed for expression of the markers of the invention and the outcomes of the individual patients from whom the samples were obtained are correlated, it will also be confirmed that altered expression of certain of the markers of the invention are strongly correlated with malignant cancers and that altered expression of other markers of the invention are strongly correlated with benign tumors. The compositions, kits, and methods of the invention are thus useful for characterizing one or more of the stage, grade, histological type, and benign/malignant nature of breast cancer in patients.

When the compositions, kits, and methods of the invention are used for characterizing one or more of the stage, grade, histological type, and benign/malignant nature of breast cancer in a patient, it is preferred that the marker or panel of markers of the invention is selected such that a positive result is obtained in at least about 20%, and preferably at least about 40%, 60%, or 80%, and more preferably in substantially all patients afflicted with a breast cancer of the corresponding stage, grade, histological type, or benign/malignant nature. Preferably, the marker or panel of markers of the invention is selected such that a positive predictive value (PPV) of greater than about 10% is obtained for the general population (more preferably coupled with an assay specificity greater than 80%).

When a plurality of markers of the invention are used in the compositions, kits, and methods of the invention, the level of expression of each marker in a patient sample can be compared with the normal level of expression of each of the plurality of markers in non-cancerous samples of the same type, either in a single reaction mixture (i.e. using reagents, such as different fluorescent probes, for each marker) or in individual reaction mixtures corresponding to one or more of the markers. In one embodiment, a significantly increased level of expression of more than one of the plurality of markers in the sample, relative to the corresponding normal levels, is an indication that the patient is afflicted with breast cancer. When a plurality of markers is used, it is preferred that 2, 3, 4, 5, 8, 10, 12, 15, 20, 30, or 50 or more individual markers be used, wherein fewer markers are preferred.

In order to maximize the sensitivity of the compositions, kits, and methods of the invention (i.e. by interference attributable to cells of non-breast origin in a patient sample), it is preferable that the marker of the invention used therein be a marker which has a restricted tissue distribution, e.g., normally not expressed in a non-breast tissue.

Only a small number of markers are known to be associated with breast cancers (e.g. BRCA1 and BRCA2). These markers are not, of course, included among the markers of the invention, although they may be used together with one or more markers of the invention in a panel of markers, for example. It is well known that certain types of genes, such as oncogenes, tumor suppressor genes, growth factor-like genes, protease-like genes, and protein kinase-like genes are often involved with development of cancers of various types. Thus, among the markers of the invention, use of those which correspond to proteins which resemble known proteins encoded by known oncogenes and tumor suppressor genes, and those which correspond to proteins which resemble growth factors, proteases, and protein kinases are preferred.

It is recognized that the compositions, kits, and methods of the invention will be of particular utility to patients having an enhanced risk of developing breast cancer and their medical advisors. Patients recognized as having an enhanced risk of developing breast cancer include, for example, patients having a familial history of breast cancer, patients identified as having a mutant oncogene (i.e. at least one allele), and patients of advancing age (i.e. women older than about 50 or 60 years).

The level of expression of a marker in normal (i.e. non-cancerous) breast tissue can be assessed in a variety of ways. In one embodiment, this normal level of expression is assessed by assessing the level of expression of the marker in a portion of breast cells which appears to be non-cancerous and by comparing this normal level of expression with the level of expression in a portion of the breast cells which is suspected of being cancerous. Alternately, and particularly as further information becomes available as a result of routine performance of the methods described herein, population-average values for normal expression of the markers of the invention may be used. In other embodiments, the 'normal' level of expression of a marker may be determined by assessing expression of the marker in a patient sample obtained from a non-cancer-afflicted patient, from a patient sample obtained from a patient before the suspected onset of breast cancer in the patient, from archived patient samples, and the like.

The invention includes compositions, kits, and methods for assessing the presence of breast cancer cells in a sample (e.g. an archived tissue sample or a sample obtained from a patient). These compositions, kits, and methods are substantially the same as those described above, except that, where necessary, the compositions, kits, and methods are adapted for use with samples other than patient samples. For example, when the sample to be used is a parafinized, archived human tissue sample, it can be necessary to adjust the ratio of compounds in the compositions of the invention, in the kits of the invention, or the methods used to assess levels of marker expression in the sample. Such methods are well known in the art and within the skill of the ordinary artisan.

The invention includes a kit for assessing the presence of breast cancer cells (e.g. in a sample such as a patient sample). The kit comprises a plurality of reagents, each of which is capable of binding specifically with a marker nucleic acid or protein. Suitable reagents for binding with a marker protein include antibodies, antibody derivatives, antibody fragments, and the like. Suitable reagents for binding with a marker nucleic acid (e.g. a genomic DNA, an mRNA, a spliced mRNA, a cDNA, or the like) include complementary nucleic acids. For example, the nucleic acid reagents may include oligonucleotides (labeled or non-labeled) fixed to a substrate, labeled oligonucleotides not bound with a substrate, pairs of PCR primers, molecular beacon probes, and the like.

The kit of the invention may optionally comprise additional components useful for performing the methods of the invention. By way of example, the kit may comprise fluids (e.g. SSC buffer) suitable for annealing complementary nucleic acids or for binding an antibody with a protein with which it specifically binds, one or more sample compartments, an instructional material which describes performance of a method of the invention, a sample of normal breast cells, a sample of breast cancer cells, and the like.

The invention also includes a method of making an isolated hybridoma which produces an antibody useful for assessing whether a patient is afflicted with breast cancer. In this method, a protein or peptide comprising the entirety or a segment of a marker protein is synthesized or isolated (e.g. by purification from a cell in which it is expressed or by transcription and translation of a nucleic acid encoding the protein or peptide in vivo or in vitro using known methods). A vertebrate, preferably a mammal such as a mouse, rat, rabbit, or sheep, is immunized using the protein or peptide. The vertebrate may optionally (and preferably) be immunized at least one additional time with the protein or peptide, so that the vertebrate exhibits a robust immune response to the protein or peptide. Splenocytes are isolated from the immunized vertebrate and fused with an immortalized cell line to form hybridomas, using any of a variety of methods well known in the art. Hybridomas formed in this manner are then screened using standard methods to identify one or more hybridomas which produce an antibody which specifically binds with the marker protein or a fragment thereof. The invention also includes hybridomas made by this method and antibodies made using such hybridomas.

The invention also includes a method of assessing the efficacy of a test compound for inhibiting breast cancer cells. As described above, differences in the level of expression of the markers of the invention correlate with the cancerous state of breast cells. Although it is recognized that changes in the levels of expression of certain of the markers of the invention likely result from the cancerous state of breast cells, it is likewise recognized that changes in the levels of expression of other of the markers of the invention induce, maintain, and promote the cancerous state of those cells. Thus, compounds which inhibit a breast cancer in a patient will cause the level of expression of one or more of the markers of the invention to change to a level nearer the normal level of expression for that marker (i.e. the level of expression for the marker in non-cancerous breast cells).

This method thus comprises comparing expression of a marker in a first breast cell sample and maintained in the presence of the test compound and expression of the marker in a second breast cell sample and maintained in the absence of the test compound. A significantly reduced expression of a marker of the invention in the presence of the test compound is an indication that the test compound inhibits breast cancer. The breast cell samples may, for example, be aliquots of a single sample of normal breast cells obtained from a patient, pooled samples of normal breast cells obtained from a patient, cells of a normal breast cell line, aliquots of a single sample of breast cancer cells obtained from a patient, pooled samples of breast cancer cells obtained from a patient, cells of a breast cancer cell line, or the like. In one embodiment, the samples are breast cancer cells obtained from a patient and a plurality of compounds known to be effective for inhibiting various breast cancers are tested in order to identify the compound which is likely to best inhibit the breast cancer in the patient.

This method may likewise be used to assess the efficacy of a therapy for inhibiting breast cancer in a patient. In this method, the level of expression of one or more markers of the invention in a pair of samples (one subjected to the therapy, the other not subjected to the therapy) is assessed. As with the method of assessing the efficacy of test compounds, if the therapy induces a significantly lower level of expression of a marker of the invention then the therapy is efficacious for inhibiting breast cancer. As above, if samples from a selected patient are used in this method, then alternative therapies can be assessed in vitro in order to select a therapy most likely to be efficacious for inhibiting breast cancer in the patient.

As described above, the cancerous state of human breast cells is correlated with changes in the levels of expression of the markers of the invention. The invention includes a method for assessing the human breast cell carcinogenic potential of a test compound. This method comprises maintaining separate aliquots of human breast cells in the presence and absence of the test compound. Expression of a marker of the invention in each of the aliquots is compared. A significantly higher level of expression of a marker of the invention in the aliquot maintained in the presence of the test compound (relative to the aliquot maintained in the absence of the test compound) is an indication that the test compound possesses human breast cell carcinogenic potential. The relative carcinogenic potentials of various test compounds can be assessed by comparing the degree of enhancement or inhibition of the level of expression of the relevant markers, by comparing the number of markers for which the level of expression is enhanced or inhibited, or by comparing both.

Various aspects of the invention are described in further detail in the following subsections.

I. Isolated Nucleic Acid Molecules

One aspect of the invention pertains to isolated nucleic acid molecules, including nucleic acids which encode a marker protein or a portion thereof. Isolated nucleic acids of the invention also include nucleic acid molecules sufficient for use as hybridization probes to identify marker nucleic acid molecules, and fragments of marker nucleic acid molecules, e.g., those suitable for use as PCR primers for the amplification or mutation of marker nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention can be isolated using standard molecular biology techniques and the sequence information in the database records described herein. Using all or a portion of such nucleic acid sequences, nucleic acid molecules of the invention can be isolated using standard hybridization and cloning techniques (e.g., as described in Sambrook et al., ed., *Molecular Cloning: A Laboratory Manual*, 2nd ed., Cold Spring Harbor Laboratory Press, Cold Spring Harbor, N.Y., 1989).

A nucleic acid molecule of the invention can be amplified using cDNA, mRNA, or genomic DNA as a template and appropriate oligonucleotide primers according to standard PCR amplification techniques. The nucleic acid so amplified can be cloned into an appropriate vector and characterized by DNA sequence analysis. Furthermore, nucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which has a nucleotide sequence complementary to the nucleotide sequence of a marker nucleic acid or to the nucleotide sequence of a nucleic acid encoding a marker protein. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule of the invention can comprise only a portion of a nucleic acid sequence, wherein the full length nucleic acid sequence comprises a marker nucleic acid or which encodes a marker protein. Such nucleic acids can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a nucleic acid of the invention.

Probes based on the sequence of a nucleic acid molecule of the invention can be used to detect transcripts or genomic sequences corresponding to one or more markers of the invention. The probe comprises a label group attached thereto, e.g., a radioisotope, a fluorescent compound, an enzyme, or an enzyme co-factor. Such probes can be used as part of a diagnostic test kit for identifying cells or tissues which mis-express the protein, such as by measuring levels of a nucleic acid molecule encoding the protein in a sample of cells from a subject, e.g., detecting mRNA levels or determining whether a gene encoding the protein has been mutated or deleted.

The invention further encompasses nucleic acid molecules that differ, due to degeneracy of the genetic code, from the nucleotide sequence of nucleic acids encoding a marker protein (e.g., protein having the sequence of a SEQ ID NO (AAs)), and thus encode the same protein.

It will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

As used herein, the phrase "allelic variant" refers to a nucleotide sequence which occurs at a given locus or to a polypeptide encoded by the nucleotide sequence.

As used herein, the terms "gene" and "recombinant gene" refer to nucleic acid molecules comprising an open reading frame encoding a polypeptide corresponding to a marker of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

In another embodiment, an isolated nucleic acid molecule of the invention is at least 7, 15, 20, 25, 30, 40, 60, 80, 100, 150, 200, 250, 300, 350, 400, 450, 550, 650, 700, 800, 900, 1000, 1200, 1400, 1600, 1800, 2000, 2200, 2400, 2600, 2800, 3000, 3500, 4000, 4500, or more nucleotides in length and hybridizes under stringent conditions to a marker nucleic acid or to a nucleic acid encoding a marker protein. As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6×sodium chloride/sodium citrate (SSC) at about 45° C., followed by one or more washes in 0.2×SSC, 0.1% SDS at 50-65° C.

In addition to naturally-occurring allelic variants of a nucleic acid molecule of the invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the invention pertains to nucleic acid molecules encoding a variant marker protein that contain changes in amino acid residues that are not essential for activity. Such variant marker proteins differ in amino acid sequence from the naturally-occurring marker proteins, yet retain biological activity. In one embodiment, such a variant marker protein has an amino acid sequence that is at least about 40% identical, 50%, 60%, 70%, 80%, 90%, 95%, or 98% identical to the amino acid sequence of a marker protein.

An isolated nucleic acid molecule encoding a variant marker protein can be created by introducing one or more nucleotide substitutions, additions or deletions into the nucleotide sequence of marker nucleic acids, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

The present invention encompasses antisense nucleic acid molecules, i.e., molecules which are complementary to a sense nucleic acid of the invention, e.g., complementary to the coding strand of a double-stranded marker cDNA molecule or complementary to a marker mRNA sequence. Accordingly, an antisense nucleic acid of the invention can hydrogen bond to (i.e. anneal with) a sense nucleic acid of the invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a marker protein. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a marker protein to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the invention includes direct injection at a tissue site or infusion of the antisense nucleic acid into a breast-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, *Nucleic Acids Res.* 15:6625-6641). The antisense nucleic acid molecule can also comprise a 2'-o-methyiribonucleotide (Inoue et al., 1987, *Nucleic Acids Res.* 15:6131-6148) or a chimeric RNA-DNA analogue (Inoue et al., 1987, *FEBS Lett.* 215:327-330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a marker protein can be designed based upon the nucleotide sequence of a cDNA corresponding to the marker. For example, a derivative of a Tetrahymena L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the invention can be used to select a catalytic RNA having a specific ribonuclease activity from a pool of RNA molecules (see, e.g., Bartel and Szostak, 1993, *Science* 261:1411-1418).

The invention also encompasses nucleic acid molecules which form triple helical structures. For example, expression of a marker of the invention can be inhibited by targeting nucleotide sequences complementary to the regulatory region of the gene encoding the marker nucleic acid or protein (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl) amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

The invention also includes molecular beacon nucleic acids having at least one region which is complementary to a nucleic acid of the invention, such that the molecular beacon is useful for quantitating the presence of the nucleic acid of the invention in a sample. A "molecular beacon" nucleic acid is a nucleic acid comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid are not annealed with one another, fluorescence of the fluorophore is quenched to a lesser degree. Molecular beacon nucleic acids are described, for example, in U.S. Pat. No. 5,876,930.

II. Isolated Proteins and Antibodies

One aspect of the invention pertains to isolated marker proteins and biologically active portions thereof, as well as polypeptide fragments suitable for use as immunogens to raise antibodies directed against a marker protein or a fragment thereof. In one embodiment, the native marker protein can be isolated from cells or tissue sources by an appropriate purification scheme using standard protein purification techniques. In another embodiment, a protein or peptide comprising the whole or a segment of the marker protein is produced by recombinant DNA techniques. Alternative to recombinant expression, such protein or peptide can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a marker protein include polypeptides comprising amino acid sequences sufficiently identical to or derived from the amino acid sequence of the marker protein, which include fewer amino acids than the full length protein, and exhibit at least one activity of the corresponding full-length protein. Typically, biologically active portions comprise a domain or motif with at least one activity of the corresponding full-length protein. A biologically active portion of a marker protein of the invention can be a polypeptide which is, for example, 10, 25, 50, 100 or more amino acids in length. Moreover, other biologically active portions, in which other regions of the marker protein are deleted, can be prepared by recombinant techniques and evaluated for one or more of the functional activities of the native form of the marker protein.

Preferred marker proteins are encoded by nucleotide sequences comprising the sequence of any of the SEQ ID NO (AAs). Other useful proteins are substantially identical (e.g., at least about 40%, preferably 50%, 60%, 70%, 80%, 90%, 95%, or 99%) to one of these sequences and retain the functional activity of the corresponding naturally-occurring marker protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=#of identical positions/total #of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the BLASTN and BLASTX programs of Altschul, et al. (1990) *J. Mol. Biol.* 215:403-410. BLAST nucleotide searches can be performed with the BLASTN program, score=100, wordlength=12 to obtain nucleotide sequences homologous to a nucleic acid molecules of the invention. BLAST protein searches can be performed with the BLASTP program, score=50, wordlength=3 to obtain amino acid sequences homologous to a protein molecules of the invention. To obtain gapped alignments for comparison purposes, a newer version of the BLAST algorithm called Gapped BLAST can be utilized as described in Altschul et al. (1997) *Nucleic Acids Res.* 25:3389-3402, which is able to perform gapped local alignments for the programs BLASTN, BLASTP and BLASTX. Alternatively, PSI-Blast can be used to perform an iterated search which detects distant relationships between molecules. When utilizing BLAST, Gapped BLAST, and PSI-Blast programs, the default parameters of the respective programs (e.g., BLASTX and BLASTN) can be used. See http://www.ncbi.nlm.nih.gov. Another preferred, non-limiting example of a mathematical algorithm utilized for the comparison of sequences is the algorithm of Myers and Miller, (1988) *CABIOS* 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The invention also provides chimeric or fusion proteins comprising a marker protein or a segment thereof. As used herein, a "chimeric protein" or "fusion protein" comprises all or part (preferably a biologically active part) of a marker protein operably linked to a heterologous polypeptide (i.e., a polypeptide other than the marker protein). Within the fusion protein, the term "operably linked" is intended to indicate that the marker protein or segment thereof and the heterologous polypeptide are fused in-frame to each other. The heterologous polypeptide can be fused to the amino-terminus or the carboxyl-terminus of the marker protein or segment.

One useful fusion protein is a GST fusion protein in which a marker protein or segment is fused to the carboxyl terminus of GST sequences. Such fusion proteins can facilitate the purification of a recombinant polypeptide of the invention.

In another embodiment, the fusion protein contains a heterologous signal sequence at its amino terminus. For example, the native signal sequence of a marker protein can be removed and replaced with a signal sequence from another protein. For example, the gp67 secretory sequence of the baculovirus envelope protein can be used as a heterologous signal sequence (Ausubel et al., ed., *Current Protocols in Molecular Biology*, John Wiley & Sons, NY, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an immunoglobulin fusion protein in which all or part of a marker protein is fused to sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a marker protein. Inhibition of ligand/receptor interaction can be useful therapeutically, both for treating proliferative and differentiative disorders and for modulating (e.g. promoting or inhibiting) cell survival. Moreover, the immunoglobulin fusion proteins of the invention can be used as immunogens to produce antibodies directed against a marker protein in a subject, to purify ligands and in screening assays to identify molecules which inhibit the interaction of the marker protein with ligands.

Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence can be used to facilitate secretion and isolation of marker proteins. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to marker proteins, fusion proteins or segments thereof having a signal sequence, as well as to such proteins from which the signal sequence has been proteolytically cleaved (i.e., the cleavage products). In one embodiment, a nucleic acid sequence encoding a signal sequence can be operably linked in an expression vector to a protein of interest, such as a marker protein or a segment thereof. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the marker proteins. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a marker protein which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the marker proteins from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198:1056; Ike et al., 1983 *Nucleic Acid Res.* 11:477).

In addition, libraries of segments of a marker protein can be used to generate a variegated population of polypeptides for screening and subsequent selection of variant marker proteins or segments thereof. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan, 1992, *Proc. Natl. Acad. Sci. USA* 89:7811-7815; Delgrave et al., 1993, *Protein Engineering* 6(3):327-331).

Another aspect of the invention pertains to antibodies directed against a protein of the invention. In preferred embodiments, the antibodies specifically bind a marker protein or a fragment thereof. The terms "antibody" and "antibodies" as used interchangeably herein refer to immunoglobulin molecules as well as fragments and derivatives thereof that comprise an immunologically active portion of an immunoglobulin molecule, (i.e., such a portion contains an antigen binding site which specifically binds an antigen, such as a marker protein, e.g. an epitope of a marker protein). An antibody which specifically binds to a protein of the invention is an antibody which binds the protein, but does not substantially bind other molecules in a sample, e.g., a biological sample, which naturally contains the protein. Examples of an immunologically active portion of an immunoglobulin molecule include, but are not limited to, single-chain antibodies (scAb), F(ab) and F(ab')$_2$ fragments.

An isolated protein of the invention or a fragment thereof can be used as an immunogen to generate antibodies. The full-length protein can be used or, alternatively, the invention provides antigenic peptide fragments for use as immunogens. The antigenic peptide of a protein of the invention comprises at least 8 (preferably 10, 15, 20, or 30 or more) amino acid residues of the amino acid sequence of one of the proteins of the invention, and encompasses at least one epitope of the protein such that an antibody raised against the peptide forms a specific immune complex with the protein. Preferred epitopes encompassed by the antigenic peptide are regions that are located on the surface of the protein, e.g., hydrophilic regions. Hydrophobicity sequence analysis, hydrophilicity sequence analysis, or similar analyses can be used to identify hydrophilic regions. In preferred embodiments, an isolated marker protein or fragment thereof is used as an immunogen.

An immunogen typically is used to prepare antibodies by immunizing a suitable (i.e. immunocompetent) subject such as a rabbit, goat, mouse, or other mammal or vertebrate. An appropriate immunogenic preparation can contain, for example, recombinantly-expressed or chemically-synthesized protein or peptide. The preparation can further include an adjuvant, such as Freund's complete or incomplete adjuvant, or a similar immunostimulatory agent. Preferred immunogen compositions are those that contain no other human proteins such as, for example, immunogen compositions made using a non-human host cell for recombinant expression of a protein of the invention. In such a manner, the resulting antibody compositions have reduced or no binding of human proteins other than a protein of the invention.

The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope. Preferred polyclonal and monoclonal antibody compositions are ones that have been selected for antibodies directed against a protein of the invention. Particularly preferred polyclonal and monoclonal antibody preparations are ones that contain only antibodies directed against a marker protein or fragment thereof.

Polyclonal antibodies can be prepared by immunizing a suitable subject with a protein of the invention as an immunogen The antibody titer in the immunized subject can be monitored over time by standard techniques, such as with an enzyme linked immunosorbent assay (ELISA) using immobilized polypeptide. At an appropriate time after immunization, e.g., when the specific antibody titers are highest, antibody-producing cells can be obtained from the subject and used to prepare monoclonal antibodies (mAb) by standard techniques, such as the hybridoma technique originally described by Kohler and Milstein (1975) *Nature* 256:495-497, the human B cell hybridoma technique (see Kozbor et al., 1983, *Immunol. Today* 4:72), the EBV-hybridoma technique (see Cole et al., pp. 77-96 In *Monoclonal Antibodies and Cancer Therapy*, Alan R. Liss, Inc., 1985) or trioma techniques. The technology for producing hybridomas is well known (see generally *Current Protocols in Immunology*, Coligan et al. ed., John Wiley & Sons, New York, 1994). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a protein of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System*, Catalog No. 27-9400-01; and the Stratagene *SurfZAP Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

The invention also provides recombinant antibodies that specifically bind a protein of the invention. In preferred embodiments, the recombinant antibodies specifically binds a marker protein or fragment thereof. Recombinant antibodies include, but are not limited to, chimeric and humanized monoclonal antibodies, comprising both human and non-human portions, single-chain antibodies and multi-specific antibodies. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Single-chain antibodies have an antigen binding site and consist of a single polypeptides. They can be produced by techniques known in the art, for example using methods described in Ladner et. al U.S. Pat. No. 4,946,778 (which is incorporated herein by reference in its entirety); Bird et al., (1988) *Science* 242:423-426; Whitlow et al., (1991) *Methods in Enzymology* 2:1-9; Whitlow et al., (1991) *Methods in Enzymology* 2:97-105; and Huston et al., (1991) *Methods in Enzymology Molecular Design and Modeling: Concepts and Applications* 203:46-88. Multi-specific antibodies are antibody molecules having at least two antigen-binding sites that specifically bind different antigens. Such molecules can be produced by techniques known in the art, for example using methods described in Segal, U.S. Pat. No. 4,676,980 (the disclosure of which is incorporated herein by reference in its entirety); Holliger et al., (1993) *Proc. Natl. Acad. Sci. USA* 90:6444-6448; Whitlow et al., (1994) *Protein Eng.* 7:1017-1026 and U.S. Pat. No. 6,121,424.

Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.) Humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison (1985) *Science* 229:1202-1207; Oi et al. (1986) *Bio/Techniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

More particularly, humanized antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide corresponding to a marker of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995) *Int. Rev. Immunol.* 13:65-93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope (Jespers et al., 1994, *Bio/technology* 12:899-903).

The antibodies of the invention can be isolated after production (e.g., from the blood or serum of the subject) or synthesis and further purified by well-known techniques. For example, IgG antibodies can be purified using protein A chromatography. Antibodies specific for a protein of the invention can be selected or (e.g., partially purified) or purified by, e.g., affinity chromatography. For example, a recombinantly expressed and purified (or partially purified) protein of the invention is produced as described herein, and covalently or non-covalently coupled to a solid support such as, for example, a chromatography column. The column can then be used to affinity purify antibodies specific for the proteins of the invention from a sample containing antibodies directed against a large number of different epitopes, thereby generating a substantially purified antibody composition, i.e., one that is substantially free of contaminating antibodies. By a substantially purified antibody composition is meant, in this context, that the antibody sample contains at most only 30% (by dry weight) of contaminating antibodies directed against epitopes other than those of the desired protein of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired protein of the invention.

In a preferred embodiment, the substantially purified antibodies of the invention may specifically bind to a signal peptide, a secreted sequence, an extracellular domain, a transmembrane or a cytoplasmic domain or cytoplasmic membrane of a protein of the invention. In a particularly preferred embodiment, the substantially purified antibodies of the invention specifically bind to a secreted sequence or an extracellular domain of the amino acid sequences of a protein of the invention. In a more preferred embodiment, the substantially purified antibodies of the invention specifically bind to a secreted sequence or an extracellular domain of the amino acid sequences of a marker protein.

An antibody directed against a protein of the invention can be used to isolate the protein by standard techniques, such as affinity chromatography or immunoprecipitation. Moreover, such an antibody can be used to detect the marker protein or fragment thereof (e.g., in a cellular lysate or cell supernatant) in order to evaluate the level and pattern of expression of the marker. The antibodies can also be used diagnostically to monitor protein levels in tissues or body fluids (e.g. in a breast-associated body fluid) as part of a clinical testing procedure, e.g., to, for example, determine the efficacy of a given treatment regimen. Detection can be facilitated by the use of an antibody derivative, which comprises an antibody of the invention coupled to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and acquorin, and examples of suitable radioactive material include $^{125}$I, $^{131}$I, $^{35}$S or $^3$H.

Antibodies of the invention may also be used as therapeutic agents in treating cancers. In a preferred embodiment, completely human antibodies of the invention are used for therapeutic treatment of human cancer patients, particularly those having a breast cancer. In another preferred embodiment, antibodies that bind specifically to a marker protein or fragment thereof are used for therapeutic treatment. Further, such therapeutic antibody may be an antibody derivative or immunotoxin comprising an antibody conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugated antibodies of the invention can be used for modifying a given biological response, for the drug moiety is not to be construed as limited to classical chemical therapeutic agents. For example, the drug moiety may be a protein or polypeptide possessing a desired biological activity. Such proteins may include, for example, a toxin such as ribosome-inhibiting protein (see Better et al., U.S. Pat. No. 6,146,631, the disclosure of which is incorporated herein in its entirety), abrin, ricin A, pseudomonas exotoxin, or diphtheria toxin; a protein such as tumor necrosis factor, .alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Accordingly, in one aspect, the invention provides substantially purified antibodies, antibody fragments and derivatives, all of which specifically bind to a protein of the invention and preferably, a marker protein. In various embodiments, the substantially purified antibodies of the invention, or fragments or derivatives thereof, can be human, non-human, chimeric and/or humanized antibodies. In another aspect, the invention provides non-human antibodies, antibody fragments and derivatives, all of which specifically bind to a protein of the invention and preferably, a marker protein. Such non-human antibodies can be goat, mouse, sheep, horse, chicken, rabbit, or rat antibodies. Alternatively, the non-human antibodies of the invention can be chimeric and/or humanized antibodies. In addition, the non-human antibodies of the invention can be polyclonal antibodies or monoclonal antibodies. In still a further aspect, the invention provides monoclonal antibodies, antibody fragments and derivatives, all of which specifically bind to a protein of the invention and preferably, a marker protein. The monoclonal antibodies can be human, humanized, chimeric and/or non-human antibodies.

The invention also provides a kit containing an antibody of the invention conjugated to a detectable substance, and instructions for use. Still another aspect of the invention is a pharmaceutical composition comprising an antibody of the invention and a pharmaceutically acceptable carrier. In one embodiment, the pharmaceutical composition comprises an antibody of the invention, a therapeutic moiety, and a pharmaceutically acceptable carrier.

III. Recombinant Expression Vectors and Host Cells

Another aspect of the invention pertains to vectors, preferably expression vectors, containing a nucleic acid encoding a marker protein (or a portion of such a protein). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

The recombinant expression vectors of the invention can be designed for expression of a marker protein or a segment thereof in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and ,Johnson, 1988, *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301-315) and pET 11d (Studier et al., p. 60-89, In *Gene Expression Technology: Methods in Enzymology* vol.185, Academic Press, San Diego, Calif., 1991). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, p. 119-128, In *Gene Expression Technology: Methods in Enzymology* vol. 185, Academic Press, San Diego, Calif., 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111-2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec1 (Baldari et al., 1987, *EMBO J.* 6:229-234), pMFa (Kurjan and Herskowitz, 1982, *Cell* 30:933-943), pJRY88 (Schultz et al., 1987, *Gene* 54:113-123), pYES2 (Invitrogen Corporation, San Diego, Calif.), and pPicZ,(Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, *Mol. Cell Biol.* 3:2156-2165) and the pVL series (Lucklow and Summers, 1989, *Virology* 170:31-39).

In yet another embodiment, a nucleic acid of the invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banedji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., 1986, *Trends in Genetics, Vol.* 1(1).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker will survive, while the other cells die).

A host cell of the invention, such as a prokaryotic or eukaryotic host cell in culture, can be used to produce a marker protein or a segment thereof. Accordingly, the invention further provides methods for producing a marker protein or a segment thereof using the host cells of the invention. In one embodiment, the method comprises culturing the host cell of the invention (into which a recombinant expression vector encoding a marker protein or a segment thereof has been introduced) in a suitable medium such that the is produced. In another embodiment, the method further comprises isolating the a marker protein or a segment thereof from the medium or the host cell.

The host cells of the invention can also be used to produce nonhuman transgenic animals. For example, in one embodiment, a host cell of the invention is a fertilized oocyte or an embryonic stem cell into which a sequences encoding a marker protein or a segment thereof have been introduced. Such host cells can then be used to create non-human transgenic animals in which exogenous sequences encoding a marker protein of the invention have been introduced into their genome or homologous recombinant animals in which endogenous gene(s) encoding a marker protein have been altered. Such animals are useful for studying the function and/or activity of the marker protein and for identifying and/or evaluating modulators of marker protein. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a nucleic acid encoding a marker protein into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, *Manipulating the Mouse Embryo*, Cold Spring Harbor Laboratory Press, Cold Spring Harbor, N.Y., 1986. Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create an homologous recombinant animal, a vector is prepared which contains at least a portion of a gene encoding a marker protein into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi, 1987, *Cell* 51:503 for a description of homologous recombination vectors). The vector is introduced into an embryonic stem cell line (e.g., by electroporation) and cells in which the introduced gene has homologously recombined with the endogenous gene are selected (see, e.g., Li et al., 1992, *Cell* 69:915). The selected cells are then injected into a blastocyst of an animal (e.g., a mouse) to form aggregation chimeras (see, e.g., Bradley, *Teratocarcinomas and Embryonic Stem Cells: A Practical Approach*, Robertson, Ed., IRL, Oxford, 1987, pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823-829 and in PCT Publication NOS. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al., 1991, *Science* 251:1351-1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810-813 and PCT Publication NOS. WO 97/07668 and WO 97/07669.

IV. Pharmaceutical Compositions

The nucleic acid molecules, polypeptides, and antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a marker nucleic acid or protein: Such methods comprise formulating a pharmaceutically acceptable carrier with an agent which modulates expression or activity of a marker nucleic acid or protein. Such compositions can further include additional active agents. Thus, the invention further includes methods for preparing a pharmaceutical composition by formulating a pharmaceutically acceptable carrier with an agent which modulates expression or activity of a marker nucleic acid or protein and one or more additional active compounds.

The invention also provides methods (also referred to herein as "screening assays") for identifying modulators, i.e., candidate or test compounds or agents (e.g., peptides, peptidomimetics, peptoids, small molecules or other drugs) which (a) bind to the marker, or (b) have a modulatory (e.g., stimulatory or inhibitory) effect on the activity of the marker or, more specifically, (c) have a modulatory effect on the interactions of the marker with one or more of its natural substrates (e.g., peptide, protein, hormone, co-factor, or nucleic acid), or (d) have a modulatory effect on the expression of the marker. Such assays typically comprise a reaction between the marker and one or more assay components. The other components may be either the test compound itself, or a combination of test compound and a natural binding partner of the marker.

The test compounds of the present invention may be obtained from any available source, including systematic libraries of natural and/or synthetic compounds. Test compounds may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten, 1992, *Biotechniques* 13:412-421), or on beads (Lam, 1991, *Nature* 354:82-84), chips (Fodor, 1993, *Nature* 364:555-556), bacteria and/or spores, (Ladner, U.S. Pat. No. 5,223,409), plasmids (Cull et al, 1992, *Proc Natl Acad Sci USA* 89:1865-1869) or on phage (Scott and Smith, 1990, *Science* 249:386-390; Devlin, 1990, *Science* 249:404-406; Cwirla et al, 1990, *Proc. Natl. Acad. Sci.* 87:6378-6382; Felici, 1991, *J. Mol. Biol.* 222:301-310; Ladner, supra.).

In one embodiment, the invention provides assays for screening candidate or test compounds which are substrates of a protein encoded by or corresponding to a marker or biologically active portion thereof. In another embodiment, the invention provides assays for screening candidate or test compounds which bind to a protein encoded by or corresponding to a marker or biologically active portion thereof. Determining the ability of the test compound to directly bind to a protein can be accomplished, for example, by coupling the compound with a radioisotope or enzymatic label such that binding of the compound to the marker can be determined by detecting the labeled marker compound in a complex. For example, compounds (e.g., marker substrates) can be labeled with $^{125}I$, $^{35}S$, $^{14}C$, or $^{3}H$, either directly or indirectly, and the radioisotope detected by direct counting of radioemission or by scintillation counting. Alternatively, assay components can be enzymatically labeled with, for example, horseradish peroxidase, alkaline phosphatase, or luciferase, and the enzymatic label detected by determination of conversion of an appropriate substrate to product.

In another embodiment, the invention provides assays for screening candidate or test compounds which modulate the expression of a marker or the activity of a protein encoded by or corresponding to a marker, or a biologically active portion thereof. In all likelihood, the protein encoded by or corresponding to the marker can, in vivo, interact with one or more molecules, such as but not limited to, peptides, proteins, hormones, cofactors and nucleic acids. For the purposes of this discussion, such cellular and extracellular molecules are referred to herein as "binding partners" or marker "substrate".

One necessary embodiment of the invention in order to facilitate such screening is the use of a protein encoded by or corresponding to marker to identify the protein's natural in vivo binding partners. There are many ways to accomplish this which are known to one skilled in the art. One example is the use of the marker protein as "bait protein" in a two-hybrid assay or three-hybrid assay (see, e.g., U.S. Pat. No. 5,283,317; Zervos et al, 1993, *Cell* 72:223-232; Madura et al, 1993, *J. Biol. Chem.* 268:12046-12054; Bartel et al ,1993, *Biotechniques* 14:920-924; Iwabuchi et al, 1993 *Oncogene* 8:1693-1696; Brent WO94/10300) in order to identify other proteins which bind to or interact with the marker (binding partners) and, therefore, are possibly involved in the natural function of the marker. Such marker binding partners are also likely to be involved in the propagation of signals by the marker protein or downstream elements of a marker protein-mediated signaling pathway. Alternatively, such marker protein binding partners may also be found to be inhibitors of the marker protein.

The two-hybrid system is based on the modular nature of most transcription factors, which consist of separable DNA-binding and activation domains. Briefly, the assay utilizes two different DNA constructs. In one construct, the gene that encodes a marker protein fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a marker-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be readily detected and cell colonies containing the functional transcription factor can be isolated and used to obtain the cloned gene which encodes the protein which interacts with the marker protein.

In a further embodiment, assays may be devised through the use of the invention for the purpose of identifying compounds which modulate (e.g., affect either positively or negatively) interactions between a marker protein and its substrates and/or binding partners. Such compounds can include, but are not limited to, molecules such as antibodies, peptides, hormones, oligonucleotides, nucleic acids, and analogs thereof. Such compounds may also be obtained from any available source, including systematic libraries of natural and/or synthetic compounds. The preferred assay components for use in this embodiment is a breast cancer marker protein identified herein, the known binding partner and/or substrate of same, and the test compound. Test compounds can be supplied from any source.

The basic principle of the assay systems used to identify compounds that interfere with the interaction between the marker protein and its binding partner involves preparing a reaction mixture containing the marker protein and its binding partner under conditions and for a time sufficient to allow the two products to interact and bind, thus forming a complex. In order to test an agent for inhibitory activity, the reaction mixture is prepared in the presence and absence of the test compound. The test compound can be initially included in the reaction mixture, or can be added at a time subsequent to the addition of the marker protein and its binding partner. Control reaction mixtures are incubated without the test compound or with a placebo. The formation of any complexes between the marker protein and its binding partner is then detected. The formation of a complex in the control reaction, but less or no such formation in the reaction mixture containing the test compound, indicates that the compound interferes with the interaction of the marker protein and its binding partner. Conversely, the formation of more complex in the presence of compound than in the control reaction indicates that the compound may enhance interaction of the marker protein and its binding partner.

The assay for compounds that interfere with the interaction of the marker protein with its binding partner may be conducted in a heterogeneous or homogeneous format. Heterogeneous assays involve anchoring either the marker protein or its binding partner onto a solid phase and detecting complexes anchored to the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the marker proteins and the binding partners (e.g., by competition) can be identified by conducting the reaction in the presence of the test substance, i.e., by adding the test substance to the reaction mixture prior to or simultaneously with the marker and its interactive binding partner. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the marker protein or its binding partner is anchored onto a solid surface or matrix, while the other corresponding non-anchored component may be labeled, either directly or indirectly. In practice, microtitre plates are often utilized for this approach. The anchored species can be immobilized by a number of methods, either non-covalent or covalent, that are typically well known to one who practices the art. Non-covalent attachment can often be accomplished simply by coating the solid surface with a solution of the marker protein or its binding partner and drying. Alternatively, an immobilized antibody specific for the assay component to be anchored can be used for this purpose. Such surfaces can often be prepared in advance and stored.

In related embodiments, a fusion protein can be provided which adds a domain that allows one or both of the assay components to be anchored to a matrix. For example, glutathione-S-transferase/marker fusion proteins or glutathione-S-transferase/binding partner can be adsorbed onto glutathione sepharose beads (Sigma Chemical, St. Louis, Mo.) or glutathione derivatized microtiter plates, which are then combined with the test compound or the test compound and either the non-adsorbed marker or its binding partner, and the mixture incubated under conditions conducive to complex formation (e.g., physiological conditions). Following incubation, the beads or microtiter plate wells are washed to remove any unbound assay components, the immobilized complex assessed either directly or indirectly, for example, as described above. Alternatively, the complexes can be dissociated from the matrix, and the level of marker binding or activity determined using standard techniques.

Other techniques for immobilizing proteins on matrices can also be used in the screening assays of the invention. For example, either a marker protein or a marker protein binding partner can be immobilized utilizing conjugation of biotin and streptavidin. Biotinylated marker protein or target molecules can be prepared from biotin-NES (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the protein-immobilized surfaces can be prepared in advance and stored.

In order to conduct the assay, the corresponding partner of the immobilized assay component is exposed to the coated surface with or without the test compound. After the reaction is complete, unreacted assay components are removed (e.g., by washing) and any complexes formed will remain immobilized on the solid surface. The detection of complexes anchored on the solid surface can be accomplished in a number of ways. Where the non-immobilized component is pre-labeled, the detection of label immobilized on the surface indicates that complexes were formed. Where the non-immobilized component is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds which modulate (inhibit or enhance) complex formation or which disrupt preformed complexes can be detected.

In an alternate embodiment of the invention, a homogeneous assay may be used. This is typically a reaction, analogous to those mentioned above, which is conducted in a liquid phase in the presence or absence of the test compound. The formed complexes are then separated from unreacted components, and the amount of complex formed is determined. As mentioned for heterogeneous assay systems, the order of addition of reactants to the liquid phase can yield information about which test compounds modulate (inhibit or enhance) complex formation and which disrupt preformed complexes.

In such a homogeneous assay, the reaction products may be separated from unreacted assay components by any of a number of standard techniques, including but not limited to: differential centrifugation, chromatography, electrophoresis and immunoprecipitation. In differential centrifugation, complexes of molecules may be separated from uncomplexed molecules through a series of centrifugal steps, due to the different sedimentation equilibria of complexes based on their different sizes and densities (see, for example, Rivas, G., and Minton, A. P., *Trends Biochem Sci* 1993 August;18(8): 284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the complex as compared to the uncomplexed molecules may be exploited to differentially separate the complex from the remaining individual reactants, for example through the use of ion-exchange chromatography resins. Such resins and chromatographic techniques are well known to one skilled in the art (see, e.g., Heegaard, 1998, *J Mol. Recognit.* 11:141-148; Hage and Tweed, 1997, *J. Chromatogr. B. Biomed. Sci. Appl.*, 699:499-525). Gel electrophoresis may also be employed to separate complexed molecules from unbound species (see, e.g., Ausubel et al (eds.), In: Current Protocols in Molecular Biology, J. Wiley & Sons, New York. 1999). In this technique, protein or nucleic acid complexes are separated based on size or charge, for example. In order to maintain the binding interaction during the electrophoretic process, nondenaturing gels in the absence of reducing agent are typically preferred, but conditions appropriate to the particular interactants will be well known to one skilled in the art. Immunoprecipitation is another common technique utilized for the isolation of a protein-protein complex from solution (see, e.g., Ausubel et al (eds.), In: Current Protocols in Molecular Biology, J. Wiley & Sons, New York. 1999). In this technique, all proteins binding to an antibody specific to one of the binding molecules are precipitated from solution by conjugating the antibody to a polymer bead that may be readily collected by centrifugation. The bound assay components are released from the beads (through a specific proteolysis event or other technique well known in the art which will not disturb the protein-protein interaction in the complex), and a second immunoprecipitation step is performed, this time utilizing antibodies specific for the correspondingly different interacting assay component. In this manner, only formed complexes should remain attached to the beads. Variations in complex formation in both the presence and the absence of a test compound can be compared, thus offering information about the ability of the compound to modulate interactions between the marker protein and its binding partner.

Also within the scope of the present invention are methods for direct detection of interactions between the marker protein and its natural binding partner and/or a test compound in a homogeneous or heterogeneous assay system without further sample manipulation. For example, the technique of fluorescence energy transfer may be utilized (see, e.g., Lakowicz et al, U.S. Pat. No. 5,631,169; Stavrianopoulos et a/, U.S. Pat. No. 4,868,103). Generally, this technique involves the addition of a fluorophore label on a first 'donor' molecule (e.g., marker or test compound) such that its emitted fluorescent energy will be absorbed by a fluorescent label on a second, 'acceptor' molecule (e.g., marker or test compound), which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter). A test substance which either enhances or hinders participation of one of the species in the preformed complex will result in the generation of a signal variant to that of background. In this way, test substances that modulate interactions between a marker and its binding partner can be identified in controlled assays.

In another embodiment, modulators of marker expression are identified in a method wherein a cell is contacted with a candidate compound and the expression of marker mRNA or protein in the cell, is determined. The level of expression of marker mRNA or protein in the presence of the candidate compound is compared to the level of expression of marker mRNA or protein in the absence of the candidate compound. The candidate compound can then be identified as a modulator of marker expression based on this comparison. For example, when expression of marker mRNA or protein is greater (statistically significantly greater) in the presence of the candidate compound than in its absence, the candidate compound is identified as a stimulator of marker mRNA or protein expression. Conversely, when expression of marker mRNA or protein is less (statistically significantly less) in the presence of the candidate compound than in its absence, the candidate compound is identified as an inhibitor of marker mRNA or protein expression. The level of marker mRNA or protein expression in the cells can be determined by methods described herein for detecting marker mRNA or protein.

In another aspect, the invention pertains to a combination of two or more of the assays described herein. For example, a modulating agent can be identified using a cell-based or a cell free assay, and the ability of the agent to modulate the activity of a marker protein can be further confirmed in vivo, e.g., in a whole animal model for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein (e.g., an marker modulating agent, an antisense marker nucleic acid molecule, an marker-specific antibody, or an marker-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

It is understood that appropriate doses of small molecule agents and protein or polypeptide agents depends upon a number of factors within the knowledge of the ordinarily skilled physician, veterinarian, or researcher. The dose(s) of these agents will vary, for example, depending upon the identity, size, and condition of the subject or sample being treated, further depending upon the route by which the composition is to be administered, if applicable, and the effect which the practitioner desires the agent to have upon the nucleic acid or polypeptide of the invention. Exemplary doses of a small molecule include milligram or microgram amounts per kilogram of subject or sample weight (e.g. about 1 microgram per kilogram to about 500 milligrams per kilogram, about 100 micrograms per kilogram to about 5 milligrams per kilogram, or about 1 microgram per kilogram to about 50 micrograms per kilogram). Exemplary doses of a protein or polypeptide include gram, milligram or microgram amounts per kilogram of subject or sample weight (e.g. about 1 microgram per kilogram to about 5 grams per kilogram, about 100 micrograms per kilogram to about 500 milligrams per kilogram, or about 1 milligram per kilogram to about 50 milligrams per kilogram). It is furthermore understood that appropriate doses of one of these agents depend upon the potency of the agent with respect to the expression or activity to be modulated. Such appropriate doses can be determined using the assays described herein. When one or more of these agents is to be administered to an animal (e.g. a human) in order to modulate expression or activity of a polypeptide or nucleic acid of the invention, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific agent employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediamine-tetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium, and then incorporating the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches, and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes having monoclonal antibodies incorporated therein or thereon) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration. A method for lipidation of antibodies is described by Cruikshank et al. (1997) *J. Acquired Immune Deficiency Syndromes and Human Retrovirology* 14:193.

The invention also provides vaccine compositions for the prevention and/or treatment of breast cancer. The invention provides breast cancer vaccine compositions in which a protein of a marker of Table 1, or a combination of proteins of the markers of Table 1, are introduced into a subject in order to stimulate an immune response against the breast cancer. The invention also provides breast cancer vaccine compositions in which a gene expression construct, which expresses a marker or fragment of a marker identified in Table 1, is introduced into the subject such that a protein or fragment of a protein encoded by a marker of Table 1 is produced by transfected cells in the subject at a higher than normal level and elicits an immune response.

In one embodiment, a breast cancer vaccine is provided and employed as an immunotherapeutic agent for the prevention of breast cancer. In another embodiment, a breast cancer vaccine is provided and employed as an immunotherapeutic agent for the treatment of breast cancer.

By way of example, a breast cancer vaccine comprised of the proteins of the markers of Table 1, may be employed for the prevention and/or treatment of breast cancer in a subject by administering the vaccine by a variety of routes, e.g., intradermally, subcutaneously, or intramuscularly. In addition, the breast cancer vaccine can be administered together with adjuvants and/or immunomodulators to boost the activity of the vaccine and the subject's response. In one embodiment, devices and/or compositions containing the vaccine, suitable for sustained or intermittent release could be, implanted in the body or topically applied thereto for the relatively slow release of such materials into the body. The breast cancer vaccine can be introduced along with immunomodulatory compounds, which can alter the type of immune response produced in order to produce a response which will be more effective in eliminating the cancer.

In another embodiment, a breast cancer vaccine comprised of an expression construct of the markers of Table 1, may be introduced by injection into muscle or by coating onto microprojectiles and using a device designed for the purpose to fire the projectiles at high speed into the skin. The cells of the subject will then express the protein(s) or fragments of proteins of the markers of Table 1 and induce an immune response. In addition, the breast cancer vaccine may be introduced along with expression constructs for immunomodulatory molecules, such as cytokines, which may increase the immune response or modulate the type of immune response produced in order to produce a response which will be more effective in eliminating the cancer.

The marker nucleic acid molecules can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al., 1994, *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Predictive Medicine

The present invention pertains to the field of predictive medicine in which diagnostic assays, prognostic assays, pharmacogenomics, and monitoring clinical trails are used for prognostic (predictive) purposes to thereby treat an individual prophylactically. Accordingly, one aspect of the present invention relates to diagnostic assays for determining the level of expression of one or more marker proteins or nucleic acids, in order to determine whether an individual is at risk of developing breast cancer. Such assays can be used for prognostic or predictive purposes to thereby prophylactically treat an individual prior to the onset of the cancer.

Yet another aspect of the invention pertains to monitoring the influence of agents (e.g., drugs or other compounds administered either to inhibit breast cancer or to treat or prevent any other disorder {i.e. in order to understand any breast carcinogenic effects that such treatment may have}) on the expression or activity of a marker of the invention in clinical trials. These and other agents are described in further detail in the following sections.

A. Diagnostic Assays

An exemplary method for detecting the presence or absence of a marker protein or nucleic acid in a biological sample involves obtaining a biological sample (e.g. a breast associated body fluid) from a test subject and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo. For example, in vitro techniques for detection of mRNA include Northern hybridizations and in situ hybridizations. In vitro techniques for detection of a marker protein include enzyme linked immunosorbent assays (ELISAs), Western blots, immunoprecipitations and immunofluorescence. In vitro techniques for detection of genomic DNA include Southern hybridizations. Furthermore, in vivo techniques for detection of a marker protein include introducing into a subject a labeled antibody directed against the protein or fragment thereof. For example, the antibody can be labeled with a radioactive marker whose presence and location in a subject can be detected by standard imaging techniques.

A general principle of such diagnostic and prognostic assays involves preparing a sample or reaction mixture that may contain a marker, and a probe, under appropriate conditions and for a time sufficient to allow the marker and probe to interact and bind, thus forming a complex that can be removed and/or detected in the reaction mixture. These assays can be conducted in a variety of ways.

For example, one method to conduct such an assay would involve anchoring the marker or probe onto a solid phase support, also referred to as a substrate, and detecting target marker/probe complexes anchored on the solid phase at the end of the reaction. In one embodiment of such a method, a sample from a subject, which is to be assayed for presence and/or concentration of marker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, marker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein.

In a preferred embodiment, the probe, when it is the unanchored assay component, can be labeled for the purpose of detection and readout of the assay, either directly or indirectly, with detectable labels discussed herein and which are well-known to one skilled in the art.

It is also possible to directly detect marker/probe complex formation without further manipulation or labeling of either component (marker or probe), for example by utilizing the technique of fluorescence energy transfer (see, for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a marker can be accomplished without labeling either assay component (probe or marker) by utilizing a technology such as real-time Biomolecular Interaction Analysis (BIA) (see, e.g., Sjolander, S. and Urbaniczky, C., 1991, *Anal. Chem.* 63:2338-2345 and Szabo et al., 1995, *Curr. Opin. Struct. Biol.* 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes may be separated from uncomplexed assay components through a series of centrifugal steps, due to the different sedimentation equilibria of complexes based on their different sizes and densities (see, for example, Rivas, G., and Minton, A. P., 1993, *Trends Biochem Sci.* 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the marker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H., 1998, *J. Mol. Recognit. Winter* 11(1-6):141-8; Hage, D. S., and Tweed, S. A. *J Chromatogr B Biomed Sci Appl* 1997 October 10;699(1-2):499-525). Gel electrophoresis may also be employed to separate complexed assay components from unbound components (see, e.g., Ausubel et al., ed., *Current Protocols in Molecular Biology*, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

In a particular embodiment, the level of marker mRNA can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from breast cells (see, e.g., Ausubel et al, ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a marker of the present invention. Other suitable probes for use in the diagnostic assays of the invention are described herein. Hybridization of an mRNA with the probe indicates that the marker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers of the present invention.

An alternative method for determining the level of mRNA marker in a sample involves the process of nucleic acid amplification, e.g., by rtPCR (the experimental embodiment set forth in Mullis, 1987, U.S. Pat. No. 4,683,202), ligase chain reaction (Barany, 1991, *Proc. Natl. Acad. Sci. USA*, 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the breast cells prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-breast cancer sample, or between samples from different sources.

Alternatively, the expression level can be provided as a relative expression level. To determine a relative expression level of a marker, the level of expression of the marker is determined for 10 or more samples of normal versus cancer cell isolates, preferably 50 or more samples, prior to the determination of the expression level for the sample in question. The mean expression level of each of the genes assayed in the larger number of samples is determined and this is used as a baseline expression level for the marker. The expression level of the marker determined for the test sample (absolute level of expression) is then divided by the mean expression value obtained for that marker. This provides a relative expression level.

Preferably, the samples used in the baseline determination will be from breast cancer or from non-breast cancer cells of breast tissue. The choice of the cell source is dependent on the use of the relative expression level. Using expression found in normal tissues as a mean expression score aids in validating whether the marker assayed is breast specific (versus normal cells). In addition, as more data is accumulated, the mean expression value can be revised, providing improved relative expression values based on accumulated data. Expression data from breast cells provides a means for grading the severity of the breast cancer state.

In another embodiment of the present invention, a marker protein is detected. A preferred agent for detecting marker protein of the invention is an antibody capable of binding to such a protein or a fragment thereof, preferably an antibody with a detectable label. Antibodies can be polyclonal, or more preferably, monoclonal. An intact antibody, or a fragment or derivative thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Proteins from breast cells can be isolated using techniques that are well known to those of skill in the art. The protein isolation methods employed can, for example, be such as those described in Harlow and Lane (Harlow and Lane, 1988, *Antibodies: A Laboratory Manual*, Cold Spring Harbor Laboratory Press, Cold Spring Harbor, N.Y.).

A variety of formats can be employed to determine whether a sample contains a protein that binds to a given antibody. Examples of such formats include, but are not limited to, enzyme immunoassay (EIA), radioimmunoassay (RIA), Western blot analysis and enzyme linked immunoabsorbant assay (ELISA). A skilled artisan can readily adapt known protein/antibody detection methods for use in determining whether breast cells express a marker of the present invention.

In one format, antibodies, or antibody fragments or derivatives, can be used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from breast cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

The invention also encompasses kits for detecting the presence of a marker protein or nucleic acid in a biological sample (e.g. a breast-associated body fluid such as a nipple aspirate). Such kits can be used to determine if a subject is suffering from or is at increased risk of developing breast cancer. For example, the kit can comprise a labeled compound or agent capable of detecting a marker protein or nucleic acid in a biological sample and means for determining the amount of the protein or mRNA in the sample (e.g., an antibody which binds the protein or a fragment thereof, or an oligonucleotide probe which binds to DNA or mRNA encoding the protein). Kits can also include instructions for interpreting the results obtained using the kit.

For antibody-based kits, the kit can comprise, for example: (1) a first antibody (e.g., attached to a solid support) which binds to a marker protein; and, optionally, (2) a second, different antibody which binds to either the protein or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a marker protein or (2) a pair of primers useful for amplifying a marker nucleic acid molecule. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples which can be assayed and compared to the test sample. Each component of the kit can be enclosed within an individual container and all of the various containers can be within a single package, along with instructions for interpreting the results of the assays performed using the kit.

B. Pharmacogenomics

The markers of the invention are also useful as pharmacogenomic markers. As used herein, a "pharmacogenomic marker" is an objective biochemical marker whose expression level correlates with a specific clinical drug response or susceptibility in a patient (see, e.g., McLeod et al. (1999) *Eur. J. Cancer* 35(12): 1650-1652). The presence or quantity of the pharmacogenomic marker expression is related to the predicted responsive of the patient and more particularly the patient's tumor to therapy with a specific drug or class of drugs. By assessing the presence or quantity of the expression of one or more pharmacogenomic markers in a patient, a drug therapy which is most appropriate for the patient, or which is predicted to have a greater degree of success, may be selected. For example, based on the presence or quantity of RNA or protein encoded by specific tumor markers in a patient, a drug or course of treatment may be selected that is optimized for the treatment of the specific tumor likely to be present in the patient. The use of pharmacogenomic markers therefore permits selecting or designing the most appropriate treatment for each cancer patient without trying different drugs or regimes.

Another aspect of pharmacogenomics deals with genetic conditions that alters the way the body acts on drugs. These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C 19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the level of expression of a marker of the invention in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a modulator of expression of a marker of the invention.

C. Monitoring Clinical Trials

Monitoring the influence of agents (e.g., drug compounds) on the level of expression of a marker of the invention can be applied not only in basic drug screening, but also in clinical trials. For example, the effectiveness of an agent to affect marker expression can be monitored in clinical trials of subjects receiving treatment for breast cancer. In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate) comprising the steps of (i) obtaining a pre-administration sample from a subject prior to administration of the agent; (ii) detecting the level of expression of one or more selected markers of the invention in the pre-administration sample; (iii) obtaining one or more post-administration samples from the subject; (iv) detecting the level of expression of the marker(s) in the post-administration samples; (v)

comparing the level of expression of the marker(s) in the pre-administration sample with the level of expression of the marker(s) in the post-administration sample or samples; and (vi) altering the administration of the agent to the subject accordingly. For example, increased expression of marker gene(s) during the course of treatment may indicate ineffective dosage and the desirability of increasing the dosage. Conversely, decreased expression of the marker gene(s) may indicate efficacious treatment and no need to change dosage.

D. Electronic Apparatus Readable Media and Arrays

Electronic apparatus readable media comprising a marker of the present invention is also provided. As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon a marker of the present invention.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the markers of the present invention.

A variety of software programs and formats can be used to store the marker information of the present invention on the electronic apparatus readable medium. For example, the marker nucleic acid sequence can be represented in a word processing text file, formatted in commercially-available software such as WordPerfect and MicroSoft Word, or represented in the form of an ASCII file, stored in a database application, such as DB2, Sybase, Oracle, or the like, as well as in other forms. Any number of data processor structuring formats (e.g., text file or database) may be employed in order to obtain or create a medium having recorded thereon the markers of the present invention.

By providing the markers of the invention in readable form, one can routinely access the marker sequence information for a variety of purposes. For example, one skilled in the art can use the nucleotide or amino acid sequences of the present invention in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has breast cancer or a pre-disposition to breast cancer, wherein the method comprises the steps of determining the presence or absence of a marker and based on the presence or absence of the marker, determining whether the subject has breast cancer or a pre-disposition to breast cancer and/or recommending a particular treatment for breast cancer or pre-breast cancer condition.

The present invention further provides in an electronic system and/or in a network, a method for determining whether a subject has breast cancer or a pre-disposition to breast cancer associated with a marker wherein the method comprises the steps of determining the presence or absence of the marker, and based on the presence or absence of the marker, determining whether the subject has breast cancer or a pre-disposition to breast cancer, and/or recommending a particular treatment for the breast cancer or pre-breast cancer condition. The method may further comprise the step of receiving phenotypic information associated with the subject and/or acquiring from a network phenotypic information associated with the subject.

The present invention also provides in a network, a method for determining whether a subject has breast cancer or a pre-disposition to breast cancer associated with a marker, said method comprising the steps of receiving information associated with the marker receiving phenotypic information associated with the subject, acquiring information from the network corresponding to the marker and/or breast cancer, and based on one or more of the phenotypic information, the marker, and the acquired information, determining whether the subject has a breast cancer or a pre-disposition to breast cancer. The method may further comprise the step of recommending a particular treatment for the breast cancer or pre-breast cancer condition.

The present invention also provides a business method for determining whether a subject has breast cancer or a pre-disposition to breast cancer, said method comprising the steps of receiving information associated with the marker, receiving phenotypic information associated with the subject, acquiring information from the network corresponding to the marker and/or breast cancer, and based on one or more of the phenotypic information, the marker, and the acquired information, determining whether the subject has breast cancer or a pre-disposition to breast cancer. The method may further comprise the step of recommending a particular treatment for the breast cancer or pre-breast cancer condition.

The invention also includes an array comprising a marker of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of breast cancer, progression of breast cancer, and processes, such a cellular transformation associated with breast cancer.

The array is also useful for ascertaining the effect of the expression of a gene on the expression of other genes in the same cell or in different cells. This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes that could serve as a molecular target for diagnosis or therapeutic intervention.

E. Surrogate Markers

The markers of the invention may serve as surrogate markers for one or more disorders or disease states or for conditions leading up to disease states, and in particular, breast cancer. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258-264; and James (1994) *AIDS Treatment News Archive* 209.

The markers of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker transcription or expression, the amplified marker may be in a quantity which is more readily detectable than the drug itself. Also, the marker may be more easily detected due to the nature of the marker itself; for example, using the methods described herein, antibodies may be employed in an immune-based detection system for a protein marker, or marker-specific radiolabeled probes may be used to detect a mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229-238; Schentag (1999) *Am. J. Health-Syst. Pharm.* 56 Suppl. 3: S21-S24; and Nicolau (1999) *Am, J. Health-Syst. Pharm.* 56 Suppl. 3: S16-S20.

VI. Experimental Protocol

A. Identification of Markers and Assembly of Their Sequence

Subtracted libraries were generated using a PCR based method that produced cDNAs of mRNAs that are present at a higher level in one mRNA population (the tester) as compared to a second mRNA population (the driver). Both tester and driver mRNA populations were converted into cDNA by reverse transcription, and then PCR amplified using the SMART PCR kit from Clontech. Tester and driver cDNAs were then hybridized using the PCR-Select cDNA subtraction kit from Clontech. This technique effected both a subtraction and normalization of the cDNA. Normalization approximately equalizes the copy numbers of low-abundance and high-abundance cDNA species. After generation of the subtracted libraries from the subtracted and normalized cDNA, 96 or more cDNA clones from each subtracted library were tested to confirm differential expression by reverse Southern hybridization.

Various subtracted libraries were constructed to isolate cDNA clones of different breast cancer marker genes. For isolating cDNA clones of genes expressed at high levels in aggressive or metastatic breast tumors, the subtracted libraries were constructed using tester cDNA generated from breast tumor tissues of patients having poor clinical outcome or aggressive tumors, or from cell lines derived from aggressive breast tumors, and driver cDNA generated from breast tumor tissues of patients having good clinical outcome or indolent tumors, or from cell lines derived from indolent breast tumors. "Poor clinical outcome" is a situation where the patient suffered cancer relapse within three years following breast cancer surgery. "Good clinical outcome" is a situation where the patient remained cancer free for over five years following breast cancer surgery. For isolating cDNA clones of genes expressed at high levels in non-aggressive or indolent breast tumors, the subtracted libraries were constructed using tester cDNA generated from breast tumor tissues of patients having good clinical outcome or indolent tumors, or from cell lines derived from indolent breast tumors, and driver cDNA generated from breast tumor tissues of patients having poor clinical outcome or having aggressive breast tumors, or from cell lines derived from aggressive breast tumors. Markers 405 and 411 were identified using such subtracted libraries.

Table 1 lists all of the markers of the invention. The markers listed in Table 2 were identified by transcription profiling using mRNA from 23 IDC node negative breast tumors with good outcome, defined as greater than five years of disease-free survival, and 16 IDC node negative breast tumors with poor clinical outcome, defined as less than three years of disease free survival. Clones having expression of at least three-fold higher in at least 25% of poor clinical outcome tumors compared to their expression in node negative, good clinical outcome tumors were designated as poor clinical outcome tumor specific markers. These cDNA clones were selected to have their protein-encoding transcript sequences determined.

The markers listed in Table 3 were identified by transcription profiling using mRNA from 16 IDC node negative breast tumors and 19 IDC node positive breast tumors. Clones having expression of at least five-fold higher in at least 15% of node-positive tumors, as compared to their expression in node negative tumors, were designated as node-positive tumor specific markers. These cDNA clones were selected to have their protein-encoding transcript sequences determined.

The markers of Table 4 were identified by transcription profiling using mRNA from 25 IDC node negative breast tumors with good outcome, defined as greater than five years of disease-free survival, and 18 IDC node negative breast tumors with proof clinical outcome, defined as less than three years of disease free survival. Clones having expression of at least five-fold higher in at least 15% of poor clinical outcome tumors compared to their expression in node negative, good clinical outcome tumors were designated as poor clinical outcome tumor specific markers. These cDNA clones were selected to have their protein-encoding transcript sequences determined.

In order to determine the full-length protein-encoding transcripts for the selected cDNA clones, the clusters in which the selected clones belong were blasted against both public and proprietary sequence databases in order to identify other EST sequences or clusters with significant overlap. Thus, contiguous EST sequences and/or clusters were assembled into protein-encoding transcripts.

An identification of protein sequence within each transcript was accomplished by obtaining one of the following:
 a) a direct match between the protein sequence and at least one EST sequence in one of its 6 possible translations;
 b) a direct match between the nucleotide sequence for the mRNA corresponding to the protein sequence and at least one EST sequence;
 c) a match between the protein sequence and a contiguous assemlby (contig) of the EST sequences with other available EST sequences in the databases in one of its 6 possible translations; or
 d) a match between the nucleotide sequence for the mRNA corresponding to the protein sequence and a contiguous assembly of the EST sequences with other available EST sequences in the databases in one of its 6 possible translations.

Markers M422, M254 and M421 are very similar (>90%) and can be mapped to an overlapping region of chromosome 22. Marker M421 is identical to the probe sequence on the transcriptional profiling array. Each transcript can be destinguished from the others based on the PCR products generated from unique primer pairs. With breast tumor RNA as the template, inly the Marker M421 product was observed. The PCR expression profile correlated very well with the transcriptional profiling data.

The expression of several node-positive tumor specific clones were further examiend by in situ hybridization (ISH) experiments using a tissue microarray containing 23 node negative IDC breast tumors and 26 node-positive IDC paraffin-embedded tumor samples. Table 12 lists markers which showed increased expression in node-positive IDCs, as compared to node-negative IDCs, as determined by in situ hybridization.

B. Summary of the Data

Tables 1-12 list markers of the invention obtained using the foregoing experimental protocol. The Tables provide the name of the gene corresponding to the marker ("Gene Name"), the sequence listing identifier of the cDNA sequence of a nucleotide transcript encoded by or corresponding to the marker ("SEQ ID NO (nts)"), the sequence listing identifier of the amino acid sequence of a protein encoded by the nuclodeite transcript ("SEQ ID NO (AAs)"), and the location of the protein coding sequence wihin the cDNA sequence ("CDS").

Table 1 lists all of the markers of the invention, which are over-expressed in breast cancer cells compared to normal (i.e., non-cancerous) breast cells. Table 2 lists markers identified by transcription profiling using mRNA from 23 IDC node negative breast tumors with good outcome and 16 IDC node negative breast tumors with poor clinical outcome. Table 3 lists markers identified by transcription profiling using mRNA from 16 IDC node negative breast tumors and 19 IDC node positive breast tumors. Table 4 lists markers identified by transcription profiling using mRNA from 25 IDC node negative breast tumors with good outcome and 18 IDC node negative breast tumors with poor clinical outcome. Table 5 lists markers particularly useful in screening for the rpesence of breast cancer ("screening markers"). Table 6 lists markers particualrly useful in assessing aggressiveness of breast cancer ("aggressiveness markers"). Table 7 lists markers particularly useful for both screening breast cancer and assessing aggressiveness of breast cancer. Table 8 lists markers whose over-expression correlates with good clinical outcome, i.e., greater than 5 years of disease-free survival. Table 9 lists markers whose over-expression correlates with poor clinical outcome, i.e., less than 3 years of disease-free survival. Table 10 lists newly identified nucleic acid and amino acid sequences. Table 11 lists newly identifies nucleic acid sequences. Table 12 lists staging markers whose expression correleates with metastasis to lymph nodes.

The contents of all references, patents, published patent applications, and database records including GenBank, IMAGE consotrium and Derwent cited throughout this application, are hereby incorporated by reference.

Other Embodiments

Those skilled in the art will recognize, or be able to ascertain using no more than routine experimentation, many equivalents to the specific emboidments of the invention described herein. Such equivalents are intended to be encompassed by the following claims:

TABLE 1

| Marker | Gene Name | SEQ ID NO (nts) | SEQ ID NO (AAs) | CDS |
|---|---|---|---|---|
| M552 | AEBP1: AE-binding protein 1 | 1 | 2 | 140 . . . 3616 |
| M83 | AKR1C1: aldo-keto reductase family 1, member C1 (20-alpha (3-alpha)-hydroxysteroid dehydrogenase) | 3 | 4 | 7 . . . 978 |
| M84 | AKR1C3: aldo-keto reductase family 1, member C3 (3-alpha hydroxysteroid dehydrogenase, type II) | 5 | 6 | 1 . . . 972 |
| M85 | ALDOB: aldolase B, fructose-bisphosphate | 7 | 8 | 126 . . . 1220 |
| M86 | AQP3: Aquaporin 3, variant 1 | 9 | 10 | 65 . . . 943 |
| M87 | AQP3: Aquaporin 3, variant 2 | 11 | 10 | 65 . . . 943 |
| M88 | AREG: amphiregulin (schwannoma-derived growth factor) | 12 | 13 | 210 . . . 968 |
| M391 | ARHGEF12: Rho guanine exchange factor (GEF) 12 | 14 | 15 | 8 . . . 4642 |
| M672 | ASS: argininosuccinate synthetase, transcript variant 1 | 16 | 17 | 76 . . . 1314 |
| M673 | ASS: argininosuccinate synthetase, transcript variant 2 | 18 | 19 | 81 . . . 1319 |
| M200 | ATP5A1: ATP synthase, H+ transporting, mitochondrial F1 complex, alpha subunit, isoform 1, cardiac muscle | 20 | 21 | 59 . . . 1720 |
| M366 | AZGP1: alpha-2-glycoprotein 1, zinc | 22 | 23 | 1 . . . 897 |
| M392 | BAK1: BCL2-antagonist/killer 1 | 24 | 25 | 201 . . . 836 |
| M89 | BF: B-factor, properdin | 26 | 27 | 41 . . . 2335 |
| M201 | BGN: biglycan | 28 | 29 | 121 . . . 1227 |
| M90 | BMI1: murine leukemia viral (bmi-1) oncogene homolog | 30 | 31 | 480 . . . 1460 |
| M394 | C1orf21: chromosome 1 open reading frame 21 | 32 | 33 | 400 . . . 765 |
| M202 | CALM1: calmodulin 1 (phosphorylase kinase, delta) | 34 | 35 | 200 . . . 649 |
| M92 | CART: cocaine- and amphetamine-regulated transcript | 36 | 37 | 20 . . . 370 |
| M367 | CD24: CD24 antigen (small cell lung carcinoma cluster 4 antigen) | 38 | 39 | 57 . . . 299 |
| M95 | CDC2: cell division cycle 2, G1 to S and G2 to M | 40 | 41 | 127 . . . 1020 |
| M203 | CDH2: cadherin 2, type 1, N-cadherin (neuronal) | 42 | 43 | 102 . . . 2822 |
| M96 | CEGP1: CEGP1 protein | 44 | 45 | 81 . . . 3080 |
| M97 | CEZANNE: zinc finger protein Cezanne | 46 | 47 | 155 . . . 2731 |
| M98 | CGI-52: CGI-52 protein, similar to phosphatidylcholine transfer protein 2 | 48 | 49 | 277 . . . 1356 |
| M99 | CGI-72: CGI-72 protein | 50 | 51 | 70 . . . 1401 |
| M254 | CGI-96: CGI-96 protein | 52 | 53 | 175 . . . 1146 |
| M100 | CLECSF1: C-type (calcium dependent, carbohydrate-recognition domain) lectin, superfamily member 1 (cartilage-derived), variant 1 | 54 | 55 | 80 . . . 673 |
| M553 | CLECSF1: C-type (calcium dependent, carbohydrate-recognition domain) lectin, superfamily member 1 (cartilage-derived), variant 2 | 56 | 57 | 53 . . . 673 |
| M204 | COL10A1: collagen, typeX, alpha 1 (Schmid metaphyseal chondrodysplasia) | 58 | 59 | 1 . . . 2043 |
| M205 | COL12A1: collagen, type XII, alpha 1, variant 1 | 60 | 61 | 1 . . . 9192 |
| M618 | COL12A1: collagen, type XII, alpha 1, variant 2 | 62 | 63 | 114 . . . 9305 |
| M12 | COL1A1: collagen, type I, alpha 1, variant 1 | 64 | 65 | 120 . . . 4514 |
| M494 | COL1Al: collagen, type I, alpha 1, variant 2 | 66 | 65 | 120 . . . 4514 |
| M206 | COL3A1: collagen, type III, alpha 1 (Ehlers-Danlos syndrome type IV, autosomal dominant) | 67 | 68 | 103 . . . 4503 |
| M101 | COL5A2: collagen, type V, alpha 2 | 69 | 70 | 139 . . . 4629 |
| M102 | COMP: cartilage oligomeric matrix protein (pseudoachondroplasia, epiphyseal dysplasia 1, multiple) | 71 | 72 | 26 . . . 2299 |
| M207 | COX6C: cytochrome c oxidase subunit VIc | 73 | 74 | 68 . . . 295 |
| OV7 | CP: ceruloplasmin (ferroxidase), variant 1 | 75 | 76 | <1 . . . 2561 |
| OV8 | CP: ceruloplasmin (ferroxidase), variant 2 | 77 | 78 | 1 . . . 3198 |
| OV66 | CP: ceruloplasmin (ferroxidase), variant 3 | 79 | 80 | 1 . . . 3210 |
| M103 | CRABP2: cellular retinoic acid-binding protein 2 | 81 | 82 | 138 . . . 554 |
| M16 | CRIP1: cysteine-rich protein 1 (intestinal) | 83 | 84 | 1 . . . 234 |
| M104 | CrkRS: CDC2-related protein kinase 7 | 85 | 86 | 34 . . . 4506 |
| M395 | CSK: c-src tyrosine kinase | 87 | 88 | 413 . . . 1765 |
| M105 | CSPG2: chondroitin sulfate proteoglycan 2 (versican) | 89 | 90 | 267 . . . 7496 |
| M208 | CTBP2: C-terminal binding protein 2, isoform 1 | 91 | 92 | 346 . . . 1683 |
| M209 | CTBP2: C-terminal binding protein 2, isoform 2 | 93 | 94 | 137 . . . 3094 |
| M396 | CYP1B1: cytochrome P450, subfamily I (dioxin-inducible), polypeptide 1 | 95 | 96 | 373 . . . 2004 |
| M106 | CYP24: cytochrome P450, subfamily XXIV (vitamin D 24-hydroxylase) | 97 | 98 | 405 . . . 1946 |
| OV40 | DD96: Epithelial protein up-regulated in carcinoma, membrane associated protein 17 | 99 | 100 | 202 . . . 546 |
| M142 | DEME-6: DEME-6 protein | 101 | 102 | <1 . . . 1725 |
| M107 | DJ167A19: hypothetical protein DJ167A19.1 | 103 | 104 | 1 . . . 921 |

TABLE 1-continued

| Marker | Gene Name | SEQ ID NO (nts) | SEQ ID NO (AAs) | CDS |
|---|---|---|---|---|
| M108 | DKFZP564D166: putative ankyrin-repeat containing protein | 105 | 106 | 95...3400 |
| M109 | DKFZP564D206: hypothetical protein DKFZP564D206 | 107 | 108 | <1...405 |
| M82 | DKFZp564I1922: adlican | 109 | 110 | 1...8487 |
| M110 | DKFZP566I133: hypothetical protein DKFZp566I133, variant 1 | 111 | 112 | 134...1354 |
| M554 | DKFZP566I133: hypothetical protein DKFZp566I133, variant 2 | 113 | 114 | 134...1354 |
| M111 | DNAJL1: hypothetical protein similar to mouse Dnajl1 | 115 | 116 | 203...1225 |
| M112 | DRIL1: dead ringer (*Drosophila*)-like 1 | 117 | 118 | 201...1982 |
| M555 | DUSP4: dual specificity phosphatase 4 | 119 | 120 | 502...1686 |
| M210 | EDIL3: EGF-like repeats and discoidin I-like domains 3 | 121 | 122 | 111...1553 |
| M211 | ENO1: enolase 1, (alpha) | 123 | 124 | 95...1399 |
| M113 | ERBB2: v-erb-b2 avian erythroblastic leukemia viral oncogene homolog 2 (neuro/glioblastoma derived oncogene homolog) | 125 | 126 | 151...3919 |
| M114 | ESR1: estrogen receptor 1 | 127 | 128 | 361...2148 |
| M115 | F2R: coagulation factor II (thrombin) receptor | 129 | 130 | 345...1622 |
| M116 | FABP7: B-FABP, fatty acid binding protein 7 | 131 | 132 | 77...475 |
| M117 | FACL2: fatty-acid-Coenzyme A ligase, long-chain 2 | 133 | 134 | 14...2110 |
| M118 | FAP: fibroblast activation protein, alpha | 135 | 136 | 209...2491 |
| M397 | FGF7: fibroblast growth factor 7 (keratinocyte growth factor) | 137 | 138 | 446...1030 |
| M119 | FKBP4: FK506-binding protein 4 | 139 | 140 | 100...1479 |
| M212 | FKSG12: pancreas tumor-related protein | 141 | 142 | 238...1125 |
| M120 | FLJ12425: hypothetical protein FLJ12425 | 143 | 144 | 42...335 |
| M121 | FLJ12910: hypothetical protein FLJ12910 | 145 | 146 | 260...1585 |
| M122 | FLJ13187: hypothetical protein FLJ13187 | 147 | 148 | 98...847 |
| M123 | FLJ14103: hypothetical protein FLJ14103 | 149 | 150 | 76...624 |
| M398 | FLJ20171: hypothetical protein FLJ20171 | 151 | 152 | 58...1134 |
| M514 | FLJ20940: hypothetical protein FLJ20940 | 153 | 154 | 236...742 |
| M399 | FLJ21174: hypothetical protein FLJ21174 | 155 | 156 | 234...881 |
| M124 | FLJ21213: hypothetical protein FLJ21213 | 157 | 158 | 3...809 |
| M125 | FLJ21879: hypothetical protein FLJ21879 | 159 | 160 | 75...1043 |
| M126 | FLJ22002: hypothetical protein FLJ22002 | 161 | 162 | 116...784 |
| M400 | FLJ22418: hypothetical protein FLJ22418 | 163 | 164 | 71...919 |
| M213 | FXYD3: FXYD domain-containing ion transport regulator 3, isoform 1 | 165 | 166 | 176...439 |
| M214 | FXYD3: FXYD domain-containing ion transport regulator 3, isoform 2 | 167 | 168 | 260...601 |
| M127 | G1P3: interferon, alpha-inducible protein (clone IFI-6-16) | 169 | 170 | 108...500 |
| M215 | GABRP: gamma-aminobutyric acid (GABA) A receptor, pi | 171 | 172 | 157...1479 |
| M128 | GATA2: GATA-binding protein 2 | 173 | 174 | 194...1618 |
| M216 | GATA3: GATA-binding protein 3, variant 1 | 175 | 176 | 461...1792 |
| M217 | GATA3: GATA-binding protein 3, variant 2 | 177 | 176 | 461...1792 |
| M218 | GATA3: GATA-binding protein 3, variant 3 | 178 | 176 | 152...1483 |
| M129 | GNLY: granulysin, isoform 519 | 179 | 180 | 281...670 |
| M130 | GNLY: granulysin, isoform NKG5 | 181 | 182 | 129...566 |
| M271 | GOLPH2: golgi phosphoprotein 2 | 183 | 184 | 151...1353 |
| M219 | GPD2: glycerol-3-phosphate dehydrogenase 2 (mitochondrial) | 185 | 186 | 124...2307 |
| M131 | GPI: glucose phosphate isomerase | 187 | 188 | 16...1692 |
| M132 | GRIA2: glutamate receptor, ionotropic, AMPA 2 | 189 | 190 | 161...2812 |
| M495 | GSTP1: glutathione S-transferase pi | 191 | 192 | 30...662 |
| M220 | GUCY1A3: guanylate cyclase 1, soluble, alpha 3, variant 1 | 193 | 194 | 520...2592 |
| M221 | GUCY1A3: guanylate cyclase 1, soluble, alpha 3, variant 2 | 195 | 194 | 386...2458 |
| M222 | GUCY1A3: guanylate cyclase 1, soluble, alpha 3, variant 3 | 196 | 194 | 407...2479 |
| M133 | GZMA: Granzyme A (Cytotoxic T-lymphocyte-associated serine esterase-3; Hanukah factor serine protease); CTL tryptase | 197 | 198 | 39...827 |
| M199 | HAG-2: anterior gradient 2 (*Xenopus laevis*) homolog | 199 | 200 | 59...586 |
| M196 | HAG-3: anterior gradient protein 3, variant 1 | 201 | 202 | 49...549 |
| M225 | HAG-3: anterior gradient protein 3, variant 2 | 203 | 204 | 116...129 |
| M134 | HDAC2: histone deacetylase 2 | 205 | 206 | 205...1671 |
| M273 | HMGCS2: 3-hydroxy-3-methylglutaryl-Coenzyme A synthase 2 (mitochondrial) | 207 | 208 | 52...1578 |
| M674 | HN1: hematological and neurological expressed 1 | 209 | 210 | 104...568 |
| M223 | HNF3A: hepatocyte nuclear factor 3, alpha | 211 | 212 | 88...1509 |

TABLE 1-continued

| Marker | Gene Name | SEQ ID NO (nts) | SEQ ID NO (AAs) | CDS |
|---|---|---|---|---|
| M135 | HOXB2: homeo box B2 | 213 | 214 | 79 ... 1149 |
| M136 | HPD: 4-hydroxyphenylpyruvate dioxygenase | 215 | 216 | 26 ... 1207 |
| M137 | HPGD: hydroxyprostaglandin dehydrogenase 15-(NAD) | 217 | 218 | 18 ... 818 |
| M401 | HSCP1: serine carboxypeptidase 1 precursor protein | 219 | 220 | 33 ... 1391 |
| M224 | HSPC155: hypothetical protein HSPC155 | 221 | 222 | 241 ... 744 |
| M402 | HSPD1: heat shock 60 kD protein 1 (chaperonin) | 223 | 224 | 25 ... 1746 |
| M403 | IGF1R: insulin-like growth factor 1 receptor | 225 | 226 | 46 ... 4149 |
| M139 | IGSF1: IGCD1, IGDC1, KIAA036, immunoglobulin superfamily, member 1 | 227 | 228 | 81 ... 4091 |
| M404 | IL6ST: interleukin 6 signal transducer (gp130, oncostatin M receptor) | 229 | 230 | 256 ... 3012 |
| M34 | INHBA: Inhibin, beta-1 (activin A, activin AB alpha polypeptide) | 231 | 232 | 86 ... 1366 |
| M140 | ISG15: interferon-stimulated protein, 15 kDa | 233 | 234 | 76 ... 573 |
| M226 | JCL-1: hepatocellular carcinoma associated protein; breast cancer associated gene 1 | 235 | 236 | 70 ... 1890 |
| M556 | JUN: v-jun avian sarcoma virus 17 oncogene homolog | 237 | 238 | 975 ... 1970 |
| M141 | KIAA0215: KIAA0215 protein | 239 | 240 | 299 ... 2770 |
| M227 | KIAA0878: KIAA0878 protein | 241 | 242 | 336 ... 2171 |
| M228 | KIAA0882: KIAA0882 protein | 243 | 244 | <1 ... 2776 |
| M143 | KIAA1051: KIAA1051 protein | 245 | 246 | <1 ... 1030 |
| M405 | KIAA1077: KIAA1077 protein | 247 | 248 | 267 ... 2882 |
| M557 | KIAA1181: KIAA1181 protein | 249 | 250 | <1 ... 1012 |
| M144 | KIAA1277: KIAA1277 protein | 251 | 252 | <5 ... 3079 |
| M145 | KIAA1361: KIAA1361 protein | 253 | 254 | <141 ... 3158 |
| M146 | KIAA1598: KIAA1598 protein | 255 | 256 | 111 ... 488 |
| M147 | KRT8: Keratin-8 | 257 | 258 | 60 ... 1511 |
| M148 | LBP: lipopolysaccharide-binding protein | 259 | 260 | 18 ... 1463 |
| M229 | LDHB: lactate dehydrogenase B | 261 | 262 | 85 ... 1089 |
| M149 | LIV-1: LIV-1 protein, estrogen regulated | 263 | 264 | 138 ... 2387 |
| M558 | LOC118430: small breast epithelial mucin | 265 | 266 | 69 ... 341 |
| M406 | LOC51242: hypothetical protein LOC51242 | 267 | 268 | 1 ... 435 |
| M230 | LOC57402: S100-type calcium binding protein A14 | 269 | 270 | 99 ... 413 |
| M559 | LPHB: lipophilin B (uteroglobin family member), prostatein-like | 271 | 272 | 64 ... 336 |
| M152 | MDS024: MDS024 protein | 273 | 274 | 65 ... 838 |
| M153 | ME1: malic enzyme 1, NADP(+)-dependent, cytosolic | 275 | 276 | 108 ... 1826 |
| M560 | MGB1: mammaglobin 1 | 277 | 278 | 61 ... 342 |
| M458 | MGB2: mammaglobin 2 | 279 | 280 | 65 ... 352 |
| M154 | MGC10765: hypothetical protein MGC10765 | 281 | 282 | 14 ... 679 |
| M155 | MGC2771: hypothetical protein MGC2771 | 283 | 284 | 185 ... 1987 |
| M231 | MGC3038: hypothetical protein MGC3038 similar to actin related protein 2/3 complex, subunit 5 | 285 | 286 | 87 ... 548 |
| M232 | MGC3077: hypothetical protein MGC3077 | 287 | 288 | 137 ... 703 |
| M675 | MGC9753: hypothetical protein MGC9753 | 289 | 290 | 1092 ... 1814 |
| M47 | MGP: matrix Gla protein | 291 | 292 | 47 ... 358 |
| M156 | MIG: monokine induced by gamma interferon | 293 | 294 | 40 ... 417 |
| M157 | MLN64: steroidogenic acute regulatory protein related | 295 | 296 | 122 ... 1459 |
| M158 | MMP11: matrix metalloproteinase 11 preproprotein; stromelysin 3 | 297 | 298 | 23 ... 1489 |
| OV52 | MMP7: matrix metalloproteinase 7 (matrilysin, uterine) | 299 | 300 | 28 ... 831 |
| M407 | MS4A7: membrane-spanning 4-domains, subfamily A, member 7, variant 1 | 301 | 302 | 147 ... 869 |
| M676 | MS4A7: membrane-spanning 4-domains, subfamily A, member 7, variant 2 | 303 | 302 | 118 ... 840 |
| M150 | MSC: mitochondrial solute carrier, hypothetical protein PRO1278; HT015 protein | 304 | 305 | 368 ... 652 |
| M151 | MST4: serine/threonine protein kinase MASK | 306 | 307 | 118 ... 1368 |
| M159 | MTHFD2: methylene tetrahydrofolate dehydrogenase (NAD+ dependent), methenyltetrahydrofolate cyclohydrolase | 308 | 309 | 16 ... 1050 |
| M669 | MUC1: mucin 1, transmembrane | 310 | 311 | 74 ... 3841 |
| M160 | MYCBP: c-myc binding protein | 312 | 313 | 39 ... 350 |
| M233 | MYO5A: myosin VA (heavy polypeptide 12, myoxin) | 314 | 315 | 251 ... 5818 |
| M161 | MYO6: myosin VI | 316 | 317 | 140 ... 3997 |
| M162 | NAT1: N-acetyltransferase 1 (arylamine N-acetyltransferase) | 318 | 319 | 1 ... 873 |
| M163 | NAT1: N-acetyltransferase 1 (arylamine N-acetyltransferase), NAT1*11B allele | 320 | 319 | 441 ... 1313 |
| M677 | NCALD: neurocalcin delta | 321 | 322 | 121 ... 702 |
| M408 | NDRG1: N-myc downstream regulated protein | 323 | 324 | 111 ... 1295 |

TABLE 1-continued

| Marker | Gene Name | SEQ ID NO (nts) | SEQ ID NO (AAs) | CDS |
|---|---|---|---|---|
| M561 | NDUFA8: NADH dehydrogenase (ubiquinone) 1 alpha subcomplex, 8 (19 kD, PGIV) | 325 | 326 | 68 . . . 586 |
| M164 | NET-6: tetraspan NET-6 protein | 327 | 328 | 163 . . . 777 |
| M165 | NPY1R: neuropeptide Y receptor Y1 | 329 | 330 | 209 . . . 1363 |
| M236 | NY-BR-1.1: breast cancer antigen NY-BR-1.1 | 331 | 332 | 181 . . . 3858 |
| M235 | NY-BR-1: breast cancer antigen NY-BR-1 | 333 | 334 | 100 . . . 4125 |
| OV48 | OPN-a: Secreted phosphoprotein-1 (osteopontin, bone sialoprotein) | 335 | 336 | 1 . . . 942 |
| OV49 | OPN-b: Secreted phosphoprotein-1 (osteopontin, bone sialoprotein) | 337 | 338 | 88 . . . 990 |
| OV50 | OPN-c: Secreted phosphoprotein-1 (osteopontin, bone sialoprotein) | 339 | 340 | 1 . . . 861 |
| M56 | OSF-2: osteoblast specific factor 2 (fasciclin I-like) | 341 | 342 | 12 . . . 2522 |
| M176 | P4HB: procollagen-proline, 2-oxoglutarate 4-dioxygenase (proline 4-hydroxylase), beta polypeptide (protein disulfide isomerase; thyroid hormone binding protein p55) | 343 | 344 | 30 . . . 1556 |
| M166 | PAFAH1B3: platelet-activating factor acetylhydrolase, isoform Ib, gamma subunit | 345 | 346 | 114 . . . 809 |
| M409 | PAR6B: PAR-6 beta | 347 | 348 | 1 . . . 1119 |
| M410 | PC4: activated RNA polymerase II: transcription cofactor 4 | 349 | 350 | 1 . . . 384 |
| M167 | PCSK1: proprotein convertase subtilisin/kexin type 1 | 351 | 352 | 190 . . . 2451 |
| M411 | PCTA-1: prostate carcinoma tumor antigen | 353 | 354 | 55 . . . 1007 |
| M412 | PDCD9: programmed cell death 9 | 355 | 356 | 39 . . . 1358 |
| M562 | PIP: prolactin-induced protein | 357 | 358 | 37 . . . 477 |
| M168 | PKIB: protein kinase (cAMP-dependent, catalytic) inhibitor beta | 359 | 360 | 112 . . . 348 |
| M414 | PLAUR: plasminogen activator, urokinase receptor | 361 | 362 | 427 . . . 1434 |
| M169 | PLU-1: putative DNA/chromatin binding motif | 363 | 364 | 90 . . . 4724 |
| M170 | PPARBP, PPAR binding protein, thyroid hormone receptor interactor 2; PPARG binding protein | 365 | 366 | 236 . . . 4936 |
| M171 | PPIF: peptidylprolyl isomerase F (cyclophilin F), variant 1 | 367 | 368 | 72 . . . 695 |
| M172 | PPIF: peptidylprolyl isomerase F (cyclophilin F), variant 2 | 369 | 368 | 84 . . . 707 |
| M173 | PPIF: peptidylprolyl isomerase F (cyclophilin F), variant 3 | 370 | 371 | 84 . . . 659 |
| M174 | PRLR: prolactin receptor | 372 | 373 | 285 . . . 2153 |
| M175 | PRO2000: PRO2000 protein | 374 | 375 | 651 . . . 1739 |
| M177 | PROML1: prominin (mouse)-like 1; hematopoietic stem cell antigen | 376 | 377 | 38 . . . 2635 |
| M237 | PSMB3: proteasome (prosome, macropain) subunit, beta type, 3 | 378 | 379 | 18 . . . 635 |
| M678 | PSMB9: proteasome (prosome, macropain) subunit, beta type, 9 (large multifunctional protease 2) | 380 | 381 | 41 . . . 700 |
| M178 | PSMD3: proteasome (prosome, macropain) 26S subunit, non-ATPase, 3 | 382 | 383 | 158 . . . 1762 |
| M415 | PTP4A2: protein tyrosine phosphatase type IVA, member 2 | 384 | 385 | 424 . . . 927 |
| M416 | RAB22B: small GTP-binding protein RAB22B | 386 | 387 | 129 . . . 716 |
| M417 | RAB27B: RAB27B, member RAS oncogene family | 388 | 389 | 93 . . . 749 |
| M179 | RAB5EP: rabaptin-5 | 390 | 391 | 189 . . . 2777 |
| M180 | RAMP3: receptor (calcitonin) activity modifying protein 3 precursor, calcitonin receptor-like receptor activity modifying protein 3 | 392 | 393 | 30 . . . 476 |
| M679 | RARRES1: retinoic acid receptor responder (tazarotene induced) 1, variant 1 | 394 | 395 | 37 . . . 723 |
| M680 | RARRES1: retinoic acid receptor responder (tazarotene induced) 1, variant 2 | 396 | 397 | 128 . . . 1012 |
| M91 | RASGRP1: RAS guanyl releasing protein 1 (calcium and DAG-regulated) | 398 | 399 | <1 . . . 2351 |
| M238 | RNB6: RNB6 protein, variant 1 | 400 | 401 | 62 . . . 1318 |
| M418 | RNB6: RNB6 protein, variant 2 | 402 | 403 | 125 . . . 1285 |
| M181 | RPL19: ribosomal protein L19 | 404 | 405 | 29 . . . 619 |
| M182 | RQCD1: rcd1 (required for cell differentiation, S. pombe) homolog 1 | 406 | 407 | 1 . . . 900 |
| M183 | S100A8: S100 calcium-binding protein A8 | 408 | 409 | 56 . . . 340 |
| M239 | SCD: stearoyl-CoA desaturase (delta-9-desaturase) | 410 | 411 | 236 . . . 1315 |
| M419 | SCYB10: small inducible cytokine subfamily B (Cys-X-Cys), member 10 | 412 | 413 | 67 . . . 363 |
| M563 | SEMA3E: sema domain, immunoglobulin domain (Ig), short basic domain, secreted, (semaphorin) 3E | 414 | 415 | 467 . . . 2794 |
| M421 | SERHL: kraken-like, variant 1 | 416 | 417 | 118 . . . 1062 |
| M422 | SERHL: kraken-like, variant 2 | 418 | 419 | 82 . . . 693 |

TABLE 1-continued

| Marker | Gene Name | SEQ ID NO (nts) | SEQ ID NO (AAs) | CDS |
|---|---|---|---|---|
| M240 | SERPINA3: serine (or cysteine) proteinase inhibitor, clade A (alpha-1 antiproteinase, antitrypsin), member 3 | 420 | 421 | 26 ... 1327 |
| M564 | SHARP: SMART/HSAC1 associated repressor protein | 422 | 423 | 205 ... 11199 |
| M241 | SIAH2: seven in absentia (*Drosophila*) homolog 2, variant 1 | 424 | 425 | 527 ... 1501 |
| M619 | SIAH2: seven in absentia (*Drosophila*) homolog 2, variant 2 | 426 | 425 | 527 ... 1501 |
| M184 | SLC9A3R1: solute carrier family 9 (sodium/hydrogen exchanger), isoform 3 regulatory factor 1 | 427 | 428 | 213 ... 1289 |
| M185 | SLPI: secretory leukocyte protease inhibitor (antileukoproteinase), variant 1 | 429 | 430 | 19 ... 417 |
| M681 | SLPI: secretory leukocyte protease inhibitor (antileukoproteinase), variant 2 | 431 | 430 | 23 ... 421 |
| M186 | SPN: asporin (LRR class 1) | 432 | 433 | 247 ... 810 |
| M423 | SQLE: squalene epoxidase | 434 | 435 | 876 ... 2600 |
| M424 | STAT4: signal transducer and activator of transcription 4, variant 1 | 436 | 437 | 82 ... 1353 |
| M425 | STAT4: signal transducer and activator of transcription 4, variant 2 | 438 | 439 | 82 ... 2328 |
| M187 | STC1: stanniocalcin 1 | 440 | 441 | 285 ... 1028 |
| M426 | STC2: stanniocalcin 2 | 442 | 443 | 135 ... 1043 |
| M188 | STHM: sialyltransferase | 444 | 445 | 40 ... 1164 |
| M565 | SYTL2: synaptotagmin-like 2 | 446 | 447 | 261 ... 1766 |
| M566 | SYTL2: synaptotagmin-like 2, isoform a | 448 | 449 | 572 ... 3304 |
| M567 | SYTL2: synaptotagmin-like 2, isoform b | 450 | 451 | 690 ... 1820 |
| M189 | TAF1C: TATA box binding protein (TBP)-associated factor, RNA polymerase I, C, 110 kD | 452 | 453 | 185 ... 2794 |
| M190 | TDP52: tumor protein D52 | 454 | 455 | 92 ... 646 |
| M568 | TFAP2A: transcription factor AP-2 alpha (activating enhancer-binding protein 2 alpha), variant 1 | 456 | 457 | 282 ... 1601 |
| M569 | TFAP2A: transcription factor AP-2 alpha (activating enhancer-binding protein 2 alpha), variant 2 | 458 | 457 | 282 ... 1601 |
| M620 | TFAP2B: transcription factor AP-2 beta (activating enhancer binding protein 2 beta), variant 1 | 459 | 460 | 257 ... 1639 |
| M621 | TFAP2B: transcription factor AP-2 beta (activating enhancer binding protein 2 beta), variant 2 | 461 | 462 | 257 ... 1666 |
| M242 | TFF1: trefoil factor 1 (breast cancer, estrogen-inducible sequence expressed in) | 463 | 464 | 41 ... 295 |
| M243 | TFF3: trefoil factor 3 (intestinal), variant 1 | 465 | 466 | 2 ... 226 |
| M682 | TFF3: trefoil factor 3 (intestinal), variant 2 | 467 | 468 | 128 ... 520 |
| M191 | TLN1: talin 1 | 469 | 470 | 127 ... 7752 |
| M192 | TRPS1: trichorhinophalangeal syndrome I | 471 | 472 | 639 ... 4484 |
| M427 | UGDH: UDP-glucose dehydrogenase | 473 | 474 | 79 ... 1563 |
| M193 | unnamed gene (1) | 475 | 476 | 75 ... 1697 |
| M194 | unnamed gene (2) | 477 | 478 | 23 ... 1066 |
| M234 | unnamed gene (3) | 479 | 480 | 55 ... 676 |
| M393 | unnamed gene (4) | 481 | 482 | 287 ... 406 |
| M420 | unnamed gene (5) | 483 | 484 | 203 ... 1951 |
| M428 | unnamed gene (6), variant 1 | 485 | 486 | 75 ... 2471 |
| M429 | unnamed gene (6), variant 2 | 487 | 488 | 75 ... 1535 |
| M622 | unnamed gene (7) | 489 | 490 | 579 à 803 |
| M93 | unnamed gene (CASB619), variant 1 | 491 | 492 | 310 ... 3351 |
| M94 | unnamed gene (CASB619), variant 2 | 493 | 494 | 310 ... 3324 |
| M138 | unnamed gene (HSECP) | 495 | 496 | 27 ... 863 |
| M195 | VAV3: vav 3 oncogene | 497 | 498 | 48 ... 2591 |
| OV25 | WFDC2: Epididymis-specific, whey-acidic protein type, four-disulfide core | 499 | 500 | 28 ... 405 |
| M197 | XBP1: X-box binding protein 1, variant 1 | 501 | 502 | 49 ... 834 |
| M244 | XBP1: X-box binding protein 1, variant 2 | 503 | 504 | 49 ... 834 |
| M198 | ZNF217: zinc finger protein 217 | 505 | 506 | 272 ... 3418 |

TABLE 2

| Marker | Gene Name | SEQ ID NO (nts) | SEQ ID NO (AAs) | CDS |
|---|---|---|---|---|
| M552 | AEBP1: AE-binding protein 1 | 1 | 2 | 140 ... 3616 |
| M391 | ARHGEF12: Rho guanine exchange factor (GEF) 12 | 14 | 15 | 8 ... 4642 |
| M672 | ASS: argininosuccinate synthetase, transcript variant 1 | 16 | 17 | 76 ... 1314 |
| M673 | ASS: argininosuccinate synthetase, transcript variant 2 | 18 | 19 | 81 ... 1319 |

TABLE 2-continued

| Marker | Gene Name | SEQ ID NO (nts) | SEQ ID NO (AAs) | CDS |
|---|---|---|---|---|
| M200 | ATP5A1: ATP synthase, H+ transporting, mitochondrial F1 complex, alpha subunit, isoform 1, cardiac muscle | 20 | 21 | 59...1720 |
| M366 | AZGP1: alpha-2-glycoprotein 1, zinc | 22 | 23 | 1...897 |
| M392 | BAK1: BCL2-antagonist/killer 1 | 24 | 25 | 201...836 |
| M201 | BGN: biglycan | 28 | 29 | 121...1227 |
| M394 | C1orf21: chromosome 1 open reading frame 21 | 32 | 33 | 400...765 |
| M202 | CALM1: calmodulin 1 (phosphorylase kinase, delta) | 34 | 35 | 200...649 |
| M367 | CD24: CD24 antigen (small cell lung carcinoma cluster 4 antigen) | 38 | 39 | 57...299 |
| M203 | CDH2: cadherin 2, type 1, N-cadherin (neuronal) | 42 | 43 | 102...2822 |
| M254 | CGI-96: CGI-96 protein | 52 | 53 | 175...1146 |
| M553 | CLECSF1: C-type (calcium dependent, carbohydrate-recognition domain) lectin, superfamily member 1 (cartilage-derived), variant 2 | 56 | 57 | 53...673 |
| M204 | COL10A1: collagen, type X, alpha 1 (Schmid metaphyseal chondrodysplasia) | 58 | 59 | 1...2043 |
| M205 | COL12A1: collagen, type XII, alpha 1, variant 1 | 60 | 61 | 1...9192 |
| M618 | COL12A1: collagen, type XII, alpha 1, variant 2 | 62 | 63 | 114...9305 |
| M494 | COL1A1: collagen, type I, alpha 1, variant 2 | 66 | 65 | 120...4514 |
| M206 | COL3A1: collagen, type III, alpha 1 (Ehlers-Danlos syndrome type IV, autosomal dominant) | 67 | 68 | 103...4503 |
| M101 | COL5A2: collagen, type V, alpha 2 | 69 | 70 | 139...4629 |
| M207 | COX6C: cytochrome c oxidase subunit VIc | 73 | 74 | 68...295 |
| M16 | CRIP1: cysteine-rich protein 1 (intestinal) | 83 | 84 | 1...234 |
| M395 | CSK: c-src tyrosine kinase | 87 | 88 | 413...1765 |
| M208 | CTBP2: C-terminal binding protein 2, isoform 1 | 91 | 92 | 346...1683 |
| M209 | CTBP2: C-terminal binding protein 2, isoform 2 | 93 | 94 | 137...3094 |
| M396 | CYP1B1: cytochrome P450, subfamily I (dioxin-inducible), polypeptide 1 | 95 | 96 | 373...2004 |
| M554 | DKFZP566I133: hypothetical protein DKFZp566I133, variant 2 | 113 | 114 | 134...1354 |
| M555 | DUSP4: dual specificity phosphatase 4 | 119 | 120 | 502...1686 |
| M210 | EDIL3: EGF-like repeats and discoidin I-like domains 3 | 121 | 122 | 111...1553 |
| M211 | ENO1: enolase 1, (alpha) | 123 | 124 | 95...1399 |
| M114 | ESR1: estrogen receptor 1 | 127 | 128 | 361...2148 |
| M397 | FGF7: fibroblast growth factor 7 (keratinocyte growth factor) | 137 | 138 | 446...1030 |
| M212 | FKSG12: pancreas tumor-related protein | 141 | 142 | 238...1125 |
| M398 | FLJ20171: hypothetical protein FLJ20171 | 151 | 152 | 58...1134 |
| M514 | FLJ20940: hypothetical protein FLJ20940 | 153 | 154 | 236...742 |
| M399 | FLJ21174: hypothetical protein FLJ21174 | 155 | 156 | 234...881 |
| M400 | FLJ22418: hypothetical protein FLJ22418 | 163 | 164 | 71...919 |
| M213 | FXYD3: FXYD domain-containing ion transport regulator 3, isoform 1 | 165 | 166 | 176...439 |
| M214 | FXYD3: FXYD domain-containing ion transport regulator 3, isoform 2 | 167 | 168 | 260...601 |
| M215 | GABRP: gamma-aminobutyric acid (GABA) A receptor, pi | 171 | 172 | 157...1479 |
| M216 | GATA3: GATA-binding protein 3, variant 1 | 175 | 176 | 461...1792 |
| M217 | GATA3: GATA-binding protein 3, variant 2 | 177 | 176 | 461...1792 |
| M218 | GATA3: GATA-binding protein 3, variant 3 | 178 | 176 | 152...1483 |
| M271 | GOLPH2: golgi phosphoprotein 2 | 183 | 184 | 151...1353 |
| M219 | GPD2: glycerol-3-phosphate dehydrogenase 2 (mitochondrial) | 185 | 186 | 124...2307 |
| M495 | GSTP1: glutathione S-transferase pi | 191 | 192 | 30...662 |
| M220 | GUCY1A3: guanylate cyclase 1, soluble, alpha 3, variant 1 | 193 | 194 | 520...2592 |
| M221 | GUCY1A3: guanylate cyclase 1, soluble, alpha 3, variant 2 | 195 | 194 | 386...2458 |
| M222 | GUCY1A3: guanylate cyclase 1, soluble, alpha 3, variant 3 | 196 | 194 | 407...2479 |
| M199 | HAG-2: anterior gradient 2 (*Xenopus laevis*) homolog | 199 | 200 | 59...586 |
| M225 | HAG-3: anterior gradient protein 3, variant 2 | 203 | 204 | 116...129 |
| M273 | HMGCS2: 3-hydroxy-3-methylglutaryl-Coenzyme A synthase 2 (mitochondrial) | 207 | 208 | 52...1578 |
| M674 | HN1: hematological and neurological expressed 1 | 209 | 210 | 104...568 |
| M223 | HNF3A: hepatocyte nuclear factor 3, alpha | 211 | 212 | 88...1509 |
| M401 | HSCP1: serine carboxypeptidase 1 precursor protein | 219 | 220 | 33...1391 |
| M224 | HSPC155: hypothetical protein HSPC155 | 221 | 222 | 241...744 |
| M402 | HSPD1: heat shock 60 kD protein 1 (chaperonin) | 223 | 224 | 25...1746 |
| M403 | IGF1R: insulin-like growth factor 1 receptor | 225 | 226 | 46...4149 |

TABLE 2-continued

| Marker | Gene Name | SEQ ID NO (nts) | SEQ ID NO (AAs) | CDS |
|---|---|---|---|---|
| M404 | IL6ST: interleukin 6 signal transducer (gp130, oncostatin M receptor) | 229 | 230 | 256 . . . 3012 |
| M34 | INHBA: Inhibin, beta-1 (activin A, activin AB alpha polypeptide) | 231 | 232 | 86 . . . 1366 |
| M226 | JCL-1: hepatocellular carcinoma associated protein; breast cancer associated gene 1 | 235 | 236 | 70 . . . 1890 |
| M556 | JUN: v-jun avian sarcoma virus 17 oncogene homolog | 237 | 238 | 975 . . . 1970 |
| M227 | KIAA0878: KIAA0878 protein | 241 | 242 | 336 . . . 2171 |
| M228 | KIAA0882: KIAA0882 protein | 243 | 244 | <1 . . . 2776 |
| M557 | KIAA1181: KIAA1181 protein | 249 | 250 | <1 . . . 1012 |
| M229 | LDHB: lactate dehydrogenase B | 261 | 262 | 85 . . . 1089 |
| M149 | LIV-1: LIV-1 protein, estrogen regulated | 263 | 264 | 138 . . . 2387 |
| M558 | LOC118430: small breast epithelial mucin | 265 | 266 | 69 . . . 341 |
| M406 | LOC51242: hypothetical protein LOC51242 | 267 | 268 | 1 . . . 435 |
| M230 | LOC57402: S100-type calcium binding protein A14 | 269 | 270 | 99 . . . 413 |
| M559 | LPHB: lipophilin B (uteroglobin family member), prostatein-like | 271 | 272 | 64 . . . 336 |
| M560 | MGB1: mammaglobin 1 | 277 | 278 | 61 . . . 342 |
| M458 | MGB2: mammaglobin 2 | 279 | 280 | 65 . . . 352 |
| M155 | MGC2771: hypothetical protein MGC2771 | 283 | 284 | 185 . . . 1987 |
| M231 | MGC3038: hypothetical protein MGC3038 similar to actin related protein 2/3 complex, subunit 5 | 285 | 286 | 87 . . . 548 |
| M232 | MGC3077: hypothetical protein MGC3077 | 287 | 288 | 137 . . . 703 |
| M675 | MGC9753: hypothetical protein MGC9753 | 289 | 290 | 1092 . . . 1814 |
| M47 | MGP: matrix Gla protein | 291 | 292 | 47 . . . 358 |
| M407 | MS4A7: membrane-spanning 4-domains, subfamily A, member 7, variant 1 | 301 | 302 | 147 . . . 869 |
| M676 | MS4A7: membrane-spanning 4-domains, subfamily A, member 7, variant 2 | 303 | 302 | 118 . . . 840 |
| M669 | MUC1 mucin 1, transmembrane | 310 | 311 | 74 . . . 3841 |
| M233 | MYO5A: myosin VA (heavy polypeptide 12, myoxin) | 314 | 315 | 251 . . . 5818 |
| M162 | NAT1: N-acetyltransferase 1 (arylamine N-acetyltransferase) | 318 | 319 | 1 . . . 873 |
| M677 | NCALD: neurocalcin delta | 321 | 322 | 121 . . . 702 |
| M408 | NDRG1: N-myc downstream regulated protein | 323 | 324 | 111 . . . 1295 |
| M561 | NDUFA8: NADH dehydrogenase (ubiquinone) 1 alpha subcomplex, 8 (19 kD, PGIV) | 325 | 326 | 68 . . . 586 |
| M164 | NET-6: tetraspan NET-6 protein | 327 | 328 | 163 . . . 777 |
| M236 | NY-BR-1.1: breast cancer antigen NY-BR-1.1 | 331 | 332 | 181 . . . 3858 |
| M235 | NY-BR-1: breast cancer antigen NY-BR-1 | 333 | 334 | 100 . . . 4125 |
| M56 | OSF-2: osteoblast specific factor 2 (fasciclin I-like) | 341 | 342 | 12 . . . 2522 |
| M409 | PAR6B: PAR-6 beta | 347 | 348 | 1 . . . 1119 |
| M410 | PC4: activated RNA polymerase II: transcription cofactor 4 | 349 | 350 | 1 . . . 384 |
| M412 | PDCD9: programmed cell death 9 | 355 | 356 | 39 . . . 1358 |
| M562 | PIP: prolactin-induced protein | 357 | 358 | 37 . . . 477 |
| M414 | PLAUR: plasminogen activator, urokinase receptor | 361 | 362 | 427 . . . 1434 |
| M237 | PSMB3: proteasome (prosome, macropain) subunit, beta type, 3 | 378 | 379 | 18 . . . 635 |
| M678 | PSMB9: proteasome (prosome, macropain) subunit, beta type, 9 (large multifunctional protease 2) | 380 | 381 | 41 . . . 700 |
| M415 | PTP4A2: protein tyrosine phosphatase type IVA, member 2 | 384 | 385 | 424 . . . 927 |
| M416 | RAB22B: small GTP-binding protein RAB22B | 386 | 387 | 129 . . . 716 |
| M417 | RAB27B: RAB27B, member RAS oncogene family | 388 | 389 | 93 . . . 749 |
| M679 | RARRES1: retinoic acid receptor responder (tazarotene induced) 1, variant 1 | 394 | 395 | 37 . . . 723 |
| M680 | RARRES1: retinoic acid receptor responder (tazarotene induced) 1, variant 2 | 396 | 397 | 128 . . . 1012 |
| M238 | RNB6: RNB6 protein, variant 1 | 400 | 401 | 62 . . . 1318 |
| M418 | RNB6: RNB6 protein, variant 2 | 402 | 403 | 125 . . . 1285 |
| M239 | SCD: stearoyl-CoA desaturase (delta-9-desaturase) | 410 | 411 | 236 . . . 1315 |
| M419 | SCYB10: small inducible cytokine subfamily B (Cys-X-Cys), member 10 | 412 | 413 | 67 . . . 363 |
| M563 | SEMA3E: sema domain, immunoglobulin domain (Ig), short basic domain, secreted, (semaphorin) 3E | 414 | 415 | 467 . . . 2794 |
| M421 | SERHL: kraken-like, variant 1 | 416 | 417 | 118 . . . 1062 |
| M422 | SERHL: kraken-like, variant 2 | 418 | 419 | 82 . . . 693 |
| M240 | SERPINA3: serine (or cysteine) proteinase inhibitor, clade A (alpha-1 antiproteinase, antitrypsin), member 3 | 420 | 421 | 26 . . . 1327 |

TABLE 2-continued

| Marker | Gene Name | SEQ ID NO (nts) | SEQ ID NO (AAs) | CDS |
|---|---|---|---|---|
| M564 | SHARP: SMART/HDAC1 associated repressor protein | 422 | 423 | 205 . . . 11199 |
| M241 | SIAH2: seven in absentia (*Drosophila*) homolog 2, variant 1 | 424 | 425 | 527 . . . 1501 |
| M619 | SIAH2: seven in absentia (*Drosophila*) homolog 2, variant 2 | 426 | 425 | 527 . . . 1501 |
| M681 | SLPI: secretory leukocyte protease inhibitor (antileukoproteinase), variant 2 | 431 | 430 | 23 . . . 421 |
| M423 | SQLE: squalene epoxidase | 434 | 435 | 876 . . . 2600 |
| M424 | STAT4: signal transducer and activator of transcription 4, variant 1 | 436 | 437 | 82 . . . 1353 |
| M425 | STAT4: signal transducer and activator of transcription 4, variant 2 | 438 | 439 | 82 . . . 2328 |
| M426 | STC2: stanniocalcin 2 | 442 | 443 | 135 . . . 1043 |
| M565 | SYTL2: synaptotagmin-like 2 | 446 | 447 | 261 . . . 1766 |
| M566 | SYTL2: synaptotagmin-like 2, isoform a | 448 | 449 | 572 . . . 3304 |
| M567 | SYTL2: synaptotagmin-like 2, isoform b | 450 | 451 | 690 . . . 1820 |
| M568 | TFAP2A: transcription factor AP-2 alpha (activating enhancer-binding protein 2 alpha), variant 1 | 456 | 457 | 282 . . . 1601 |
| M569 | TFAP2A: transcription factor AP-2 alpha (activating enhancer-binding protein 2 alpha), variant 2 | 458 | 457 | 282 . . . 1601 |
| M620 | TFAP2B: transcription factor AP-2 beta (activating enhancer binding protein 2 beta), variant 1 | 459 | 460 | 257 . . . 1639 |
| M621 | TFAP2B: transcription factor AP-2 beta (activating enhancer binding protein 2 beta), variant 2 | 461 | 462 | 257 . . . 1666 |
| M242 | TFF1: trefoil factor 1 (breast cancer, estrogen-inducible sequence expressed in) | 463 | 464 | 41 . . . 295 |
| M243 | TFF3: trefoil factor 3 (intestinal), variant 1 | 465 | 466 | 2 . . . 226 |
| M192 | TRPS1: trichorhinophalangeal syndrome I | 471 | 472 | 639 . . . 4484 |
| M427 | UGDH: UDP-glucose dehydrogenase | 473 | 474 | 79 . . . 1563 |
| M194 | unnamed gene (2) | 477 | 478 | 23 . . . 1066 |
| M234 | unnamed gene (3) | 479 | 480 | 55 . . . 676 |
| M393 | unnamed gene (4) | 481 | 482 | 287 . . . 406 |
| M420 | unnamed gene (5) | 483 | 484 | 203 . . . 1951 |
| M428 | unnamed gene (6), variant 1 | 485 | 486 | 75 . . . 2471 |
| M429 | unnamed gene (6), variant 2 | 487 | 488 | 75 . . . 1535 |
| M622 | unnamed gene (7) | 489 | 490 | 579à803 |
| OV25 | WFDC2: Epididymis-specific, whey-acidic protein type, four-disulfide core | 499 | 500 | 28 . . . 405 |
| M244 | XBP1: X-box binding protein 1, variant 2 | 503 | 504 | 49 . . . 834 |

TABLE 3

| Marker | Gene Name | SEQ ID NO (nts) | SEQ ID NO (AAs) | CDS |
|---|---|---|---|---|
| M83 | AKR1C1: aldo-keto reductase family 1, member C1 (20-alpha (3-alpha)-hydroxysteroid dehydrogenase) | 3 | 4 | 7 . . . 978 |
| M84 | AKR1C3: aldo-keto reductase family 1, member C3 (3-alpha hydroxysteroid dehydrogenase, type II) | 5 | 6 | 1 . . . 972 |
| M85 | ALDOB: aldolase B, fructose-bisphosphate | 7 | 8 | 126 . . . 1220 |
| M86 | AQP3: Aquaporin 3, variant 1 | 9 | 10 | 65 . . . 943 |
| M87 | AQP3: Aquaporin 3, variant 2 | 11 | 10 | 65 . . . 943 |
| M88 | AREG: amphiregulin (schwannoma-derived growth factor) | 12 | 13 | 210 . . . 968 |
| M89 | BF: B-factor, properdin | 26 | 27 | 41 . . . 2335 |
| M90 | BMI1: murine leukemia viral (bmi-1) oncogene homolog | 30 | 31 | 480 . . . 1460 |
| M92 | CART: cocaine- and amphetamine-regulated transcript | 36 | 37 | 20 . . . 370 |
| M95 | CDC2: cell division cycle 2, G1 to S and G2 to M | 40 | 41 | 127 . . . 1020 |
| M96 | CEGP1: CEGP1 protein | 44 | 45 | 81 . . . 3080 |
| M97 | CEZANNE: zinc finger protein Cezanne | 46 | 47 | 155 . . . 2731 |
| M98 | CGI-52: CGI-52 protein, similar to phosphatidylcholine transfer protein 2 | 48 | 49 | 277 . . . 1356 |
| M99 | CGI-72: CGI-72 protein | 50 | 51 | 70 . . . 1401 |
| M100 | CLECSF1: C-type (calcium dependent, carbohydrate-recognition domain) lectin, superfamily member 1 (cartilage-derived), variant 1 | 54 | 55 | 80 . . . 673 |
| M12 | COL1A1: collagen, type I, alpha 1, variant 1 | 64 | 65 | 120 . . . 4514 |
| M102 | COMP: cartilage oligomeric matrix protein (pseudoachondroplasia, epiphyseal dysplasia 1, multiple) | 71 | 72 | 26 . . . 2299 |
| OV7 | CP: ceruloplasmin (ferroxidase), variant 1 | 75 | 76 | <1 . . . 2561 |

TABLE 3-continued

| Marker | Gene Name | SEQ ID NO (nts) | SEQ ID NO (AAs) | CDS |
|---|---|---|---|---|
| OV8 | CP: ceruloplasmin (ferroxidase), variant 2 | 77 | 78 | 1 . . . 3198 |
| OV66 | CP: ceruloplasmin (ferroxidase), variant 3 | 79 | 80 | 1 . . . 3210 |
| M103 | CRABP2: cellular retinoic acid-binding protein 2 | 81 | 82 | 138 . . . 554 |
| M104 | CrkRS: CDC2-related protein kinase 7 | 85 | 86 | 34 . . . 4506 |
| M105 | CSPG2: chondroitin sulfate proteoglycan 2 (versican) | 89 | 90 | 267 . . . 7496 |
| M106 | CYP24: cytochrome P450, subfamily XXIV (vitamin D 24-hydroxylase) | 97 | 98 | 405 . . . 1946 |
| OV40 | DD96: Epithelial protein up-regulated in carcinoma, membrane associated protein 17 | 99 | 100 | 202 . . . 546 |
| M142 | DEME-6: DEME-6 protein | 101 | 102 | <1 . . . 1725 |
| M107 | DJ167A19: hypothetical protein DJ167A19.1 | 103 | 104 | 1 . . . 921 |
| M108 | DKFZP564D166: putative ankyrin-repeat containing protein | 105 | 106 | 95 . . . 3400 |
| M109 | DKFZP564D206: hypothetical protein DKFZP564D206 | 107 | 108 | <1 . . . 405 |
| M82 | DKFZp564I1922: adlican | 109 | 110 | 1 . . . 8487 |
| M110 | DKFZP566I133: hypothetical protein DKFZp566I133, variant 1 | 111 | 112 | 134 . . . 1354 |
| M111 | DNAJL1: hypothetical protein similar to mouse Dnajl1 | 115 | 116 | 203 . . . 1225 |
| M112 | DRIL1: dead ringer (*Drosophila*)-like 1 | 117 | 118 | 201 . . . 1982 |
| M113 | ERBB2: v-erb-b2 avian erythroblastic leukemia viral oncogene homolog 2 (neuro/glioblastoma derived oncogene homolog) | 125 | 126 | 151 . . . 3919 |
| M116 | FABP7: B-FABP, fatty acid binding protein 7 | 131 | 132 | 77 . . . 475 |
| M118 | FAP: fibroblast activation protein, alpha | 135 | 136 | 209 . . . 2491 |
| M119 | FKBP4: FK506-binding protein 4 | 139 | 140 | 100 . . . 1479 |
| M120 | FLJ12425: hypothetical protein FLJ12425 | 143 | 144 | 42 . . . 335 |
| M121 | FLJ12910: hypothetical protein FLJ12910 | 145 | 146 | 260 . . . 1585 |
| M122 | FLJ13187: hypothetical protein FLJ13187 | 147 | 148 | 98 . . . 847 |
| M123 | FLJ14103: hypothetical protein FLJ14103 | 149 | 150 | 76 . . . 624 |
| M124 | FLJ21213: hypothetical protein FLJ21213 | 157 | 158 | 3 . . . 809 |
| M125 | FLJ21879: hypothetical protein FLJ21879 | 159 | 160 | 75 . . . 1043 |
| M126 | FLJ22002: hypothetical protein FLJ22002 | 161 | 162 | 116 . . . 784 |
| M127 | G1P3: interferon, alpha-inducible protein (clone IFI-6-16) | 169 | 170 | 108 . . . 500 |
| M128 | GATA2: GATA-binding protein 2 | 173 | 174 | 194 . . . 1618 |
| M129 | GNLY: granulysin, isoform 519 | 179 | 180 | 281 . . . 670 |
| M130 | GNLY: granulysin, isoform NKG5 | 181 | 182 | 129 . . . 566 |
| M132 | GRIA2: glutamate receptor, ionotropic, AMPA 2 | 189 | 190 | 161 . . . 2812 |
| M133 | GZMA: Granzyme A (Cytotoxic T-lymphocyte-associated serine esterase-3; Hanukah factor serine protease); CTL tryptase | 197 | 198 | 39 . . . 827 |
| M134 | HDAC2: histone deacetylase 2 | 205 | 206 | 205 . . . 1671 |
| M135 | HOXB2: homeo box B2 | 213 | 214 | 79 . . . 1149 |
| M136 | HPD: 4-hydroxyphenylpyruvate dioxygenase | 215 | 216 | 26 . . . 1207 |
| M137 | HPGD: hydroxyprostaglandin dehydrogenase 15-(NAD) | 217 | 218 | 18 . . . 818 |
| M139 | IGSF1: IGCD1, IGDC1, KIAA036, immunoglobulin superfamily, member 1 | 227 | 228 | 81 . . . 4091 |
| M140 | ISG15: interferon-stimulated protein, 15 kDa | 233 | 234 | 76 . . . 573 |
| M141 | KIAA0215: KIAA0215 protein | 239 | 240 | 299 . . . 2770 |
| M143 | KIAA1051: KIAA1051 protein | 245 | 246 | <1 . . . 1030 |
| M144 | KIAA1277: KIAA1277 protein | 251 | 252 | <5 . . . 3079 |
| M145 | KIAA1361: KIAA1361 protein | 253 | 254 | <141 . . . 3158 |
| M146 | KIAA1598: KIAA1598 protein | 255 | 256 | 111 . . . 488 |
| M147 | KRT8: Keratin-8 | 257 | 258 | 60 . . . 1511 |
| M148 | LBP: lipopolysaccharide-binding protein | 259 | 260 | 18 . . . 1463 |
| M152 | MDS024: MDS024 protein | 273 | 274 | 65 . . . 838 |
| M153 | ME1: malic enzyme 1, NADP(+)-dependent, cytosolic | 275 | 276 | 108 . . . 1826 |
| M154 | MGC10765: hypothetical protein MGC10765 | 281 | 282 | 14 . . . 679 |
| M156 | MIG: monokine induced by gamma interferon | 293 | 294 | 40 . . . 417 |
| M157 | MLN64: steroidogenic acute regulatory protein related | 295 | 296 | 122 . . . 1459 |
| OV52 | MMP7: matrix metalloproteinase 7 (matrilysin, uterine) | 299 | 300 | 28 . . . 831 |
| M150 | MSC: mitochondrial solute carrier, hypothetical protein PRO1278; HT015 protein | 304 | 305 | 368 . . . 652 |
| M151 | MST4: serine/threonine protein kinase MASK | 306 | 307 | 118 . . . 1368 |
| M160 | MYCBP: c-myc binding protein | 312 | 313 | 39 . . . 350 |
| M161 | MYO6: myosin VI | 316 | 317 | 140 . . . 3997 |
| M165 | NPY1R: neuropeptide Y receptor Y1 | 329 | 330 | 209 . . . 1363 |
| OV48 | OPN-a: Secreted phosphoprotein-1 (osteopontin, bone sialoprotein) | 335 | 336 | 1 . . . 942 |

TABLE 3-continued

| Marker | Gene Name | SEQ ID NO (nts) | SEQ ID NO (AAs) | CDS |
|---|---|---|---|---|
| OV49 | OPN-b: Secreted phosphoprotein-1 (osteopontin, bone sialoprotein) | 337 | 338 | 88 ... 990 |
| OV50 | OPN-c: Secreted phosphoprotein-1 (osteopontin, bone sialoprotein) | 339 | 340 | 1 ... 861 |
| M176 | P4HB: procoilagen-proline, 2-oxoglutarate 4-dioxygenase (proline 4-hydroxylase), beta polypeptide (protein disulfide isomerase; thyroid hormone binding protein p55) | 343 | 344 | 30 ... 1556 |
| M166 | PAFAH1B3: platelet-activating factor acetylhydrolase, isoform Ib, gamma subunit | 345 | 346 | 114 ... 809 |
| M167 | PCSK1: proprotein convertase subtilisin/kexin type 1 | 351 | 352 | 190 ... 2451 |
| M168 | PKIB: protein kinase (cAMP-dependent, catalytic) inhibitor beta | 359 | 360 | 112 ... 348 |
| M169 | PLU-1: putative DNA/chromatin binding motif | 363 | 364 | 90 ... 4724 |
| M170 | PPARBP, PPAR binding protein, thyroid hormone receptor interactor 2; PPARG binding protein | 365 | 366 | 236 ... 4936 |
| M171 | PPIF: peptidylprolyl isomerase F (cyclophilin F), variant 1 | 367 | 368 | 72 ... 695 |
| M172 | PPIF: peptidylprolyl isomerase F (cyclophilin F), variant 2 | 369 | 368 | 84 ... 707 |
| M173 | PPIF: peptidylprolyl isomerase F (cyclophilin F), variant 3 | 370 | 371 | 84 ... 659 |
| M174 | PRLR: prolactin receptor | 372 | 373 | 285 ... 2153 |
| M175 | PRO2000: PRO2000 protein | 374 | 375 | 651 ... 1739 |
| M177 | PROML1: prominin (mouse)-like 1; hematopoietic stem cell antigen | 376 | 377 | 38 ... 2635 |
| M179 | RAB5EP: rabaptin-5 | 390 | 391 | 189 ... 2777 |
| M180 | RAMP3: receptor (calcitonin) activity modifying protein 3 precursor; calcitonin receptor-like receptor activity modifying protein 3 | 392 | 393 | 30 ... 476 |
| M91 | RASGRP1: RAS guanyl releasing protein 1 (calcium and DAG-regulated) | 398 | 399 | <1 ... 2351 |
| M182 | RQCD1: rcd1 (required for cell differentiation, S. pombe) homolog 1 | 406 | 407 | 1 ... 900 |
| M183 | S100A8: S100 calcium-binding protein A8 | 408 | 409 | 56 ... 340 |
| M184 | SLC9A3R1: solute carrier family 9 (sodium/hydrogen exchanger), isoform 3 regulatory factor 1 | 427 | 428 | 213 ... 1289 |
| M185 | SLPI: secretory leukocyte protease inhibitor (antileukoproteinase), variant 1 | 429 | 430 | 19 ... 417 |
| M186 | SPN: asporin (LRR class 1) | 432 | 433 | 247 ... 810 |
| M188 | STHM: sialyltransferase | 444 | 445 | 40 ... 1164 |
| M189 | TAF1C: TATA box binding protein (TBP)-associated factor, RNA polymerase I, C, 110 kD | 452 | 453 | 185 ... 2794 |
| M190 | TDP52: tumor protein D52 | 454 | 455 | 92 ... 646 |
| M682 | TFF3: trefoil factor 3 (intestinal), variant 2 | 467 | 468 | 128 ... 520 |
| M191 | TLN1: talin 1 | 469 | 470 | 127 ... 7752 |
| M193 | unnamed gene (1) | 475 | 476 | 75 ... 1697 |
| M93 | unnamed gene (CASB619), variant 1 | 491 | 492 | 310 ... 3351 |
| M94 | unnamed gene (CASB619), variant 2 | 493 | 494 | 310 ... 3324 |
| M138 | unnamed gene (HSECP) | 495 | 496 | 27 ... 863 |
| M195 | VAV3: vav 3 oncogene | 497 | 498 | 48 ... 2591 |
| M197 | XBP1: X-box binding protein 1, variant 1 | 501 | 502 | 49 ... 834 |
| M198 | ZNF217: zinc finger protein 217 | 505 | 506 | 272 ... 3418 |

TABLE 4

| Marker | Gene Name | SEQ ID NO (nts) | SEQ ID NO (AAs) | CDS |
|---|---|---|---|---|
| M115 | F2R: coagulation factor II (thrombin) receptor | 129 | 130 | 345 ... 1622 |
| M117 | FACL2: fatty-acid-Coenzyme A ligase, long-chain 2 | 133 | 134 | 14 ... 2110 |
| M131 | GPI: glucose phosphate isomerase | 187 | 188 | 16 ... 1692 |
| M196 | HAG-3: anterior gradient protein 3, variant 1 | 201 | 202 | 49 ... 549 |
| M158 | MMP11: matrix metalloproteinase 11 preproprotein; stromelysin 3 | 297 | 298 | 23 ... 1489 |
| M159 | MTHFD2: methylene tetrahydrofolate dehydrogenase (NAD+ dependent), methenyltetrahydrofolate cyclohydrolase | 308 | 309 | 16 ... 1050 |
| M163 | NAT1: N-acetyltransferase 1 (arylamine N-acetyltransferase), NAT1*11B allele | 320 | 319 | 441 ... 1313 |

TABLE 4-continued

| Marker | Gene Name | SEQ ID NO (nts) | SEQ ID NO (AAs) | CDS |
|---|---|---|---|---|
| M178 | PSMD3: proteasome (prosome, macropain) 26S subunit, non-ATPase, 3 | 382 | 383 | 158 . . . 1762 |
| M181 | RPL19: ribosomal protein L19 | 404 | 405 | 29 . . . 619 |
| M187 | STC1: stanniocalcin 1 | 440 | 441 | 285 . . . 1028 |

TABLE 5

| Marker | Gene Name | SEQ ID NO (nts) | SEQ ID NO (AAs) | CDS |
|---|---|---|---|---|
| M552 | AEBP1: AE-binding protein 1 | 1 | 2 | 140 . . . 3616 |
| M85 | ALDOB: aldolase B, fructose-bisphosphate | 7 | 8 | 126 . . . 1220 |
| M88 | AREG: amphiregulin (schwannoma-derived growth factor) | 12 | 13 | 210 . . . 968 |
| M366 | AZGP1: alpha-2-glycoprotein 1, zinc | 22 | 23 | 1 . . . 897 |
| M89 | BF: B-factor, properdin | 26 | 27 | 41 . . . 2335 |
| M201 | BGN: biglycan | 28 | 29 | 121 . . . 1227 |
| M90 | BMI1: murine leukemia viral (bmi-1) oncogene homolog | 30 | 31 | 480 . . . 1460 |
| M92 | CART: cocaine- and amphetamine-regulated transcript | 36 | 37 | 20 . . . 370 |
| M203 | CDH2: cadherin 2, type 1, N-cadherin (neuronal) | 42 | 43 | 102 . . . 2822 |
| M96 | CEGP1: CEGP1 protein | 44 | 45 | 81 . . . 3080 |
| M97 | CEZANNE zinc finger protein Cezanne | 46 | 47 | 155 . . . 2731 |
| M98 | CGI-52: CGI-52 protein, similar to phosphatidylcholine transfer protein 2 | 48 | 49 | 277 . . . 1356 |
| M99 | CGI-72: CGI-72 protein | 50 | 51 | 70 . . . 1401 |
| M100 | CLECSF1: C-type (calcium dependent, carbohydrate-recognition domain) lectin, superfamily member 1 (cartilage-derived), variant 1 | 54 | 55 | 80 . . . 673 |
| M553 | CLECSF1: C-type (calcium dependent, carbohydrate-recognition domain) lectin, superfamily member 1 (cartilage-derived), variant 2 | 56 | 57 | 53 . . . 673 |
| M204 | COL10A1: collagen, type X, alpha 1 (Schmid metaphyseal chondrodysplasia) | 58 | 59 | 1 . . . 2043 |
| M205 | COL12A1: collagen, type XII, alpha 1, variant 1 | 60 | 61 | 1 . . . 9192 |
| M618 | COL12A1: collagen, type XII, alpha 1, variant 2 | 62 | 63 | 114 . . . 9305 |
| M12 | COL1A1: collagen, type I, alpha 1, variant 1 | 64 | 65 | 120 . . . 4514 |
| M494 | COL1A1: collagen, type I, alpha 1, variant 2 | 66 | 65 | 120 . . . 4514 |
| M206 | COL3A1: collagen, type III, alpha 1 (Ehlers-Danlos syndrome type IV, autosomal dominant) | 67 | 68 | 103 . . . 4503 |
| M101 | COL5A2: collagen, type V, alpha 2 | 69 | 70 | 139 . . . 4629 |
| M102 | COMP: cartilage oligomeric matrix protein (pseudoachondroplasia, epiphyseal dysplasia 1, multiple) | 71 | 72 | 26 . . . 2299 |
| M207 | COX6C: cytochrome c oxidase subunit VIc | 73 | 74 | 68 . . . 295 |
| OV7 | CP: ceruloplasmin (ferroxidase), variant 1 | 75 | 76 | <1 . . . 2561 |
| OV8 | CP: ceruloplasmin (ferroxidase), variant 2 | 77 | 78 | 1 . . . 3198 |
| OV66 | CP: ceruloplasmin (ferroxidase), variant 3 | 79 | 80 | 1 . . . 3210 |
| M103 | CRABP2: cellular retinoic acid-binding protein 2 | 81 | 82 | 138 . . . 554 |
| M16 | CRIP1: cysteine-rich protein 1 (intestinal) | 83 | 84 | 1 . . . 234 |
| M105 | CSPG2: chondroitin sulfate proteoglycan 2 (versican) | 89 | 90 | 267 . . . 7496 |
| M208 | CTBP2: C-terminal binding protein 2, isoform 1 | 91 | 92 | 346 . . . 1683 |
| M209 | CTBP2: C-terminal binding protein 2, isoform 2 | 93 | 94 | 137 . . . 3094 |
| OV40 | DD96: Epithelial protein up-regulated in carcinoma, membrane associated protein 17 | 99 | 100 | 202 . . . 546 |
| M142 | DEME-6: DEME-6 protein | 101 | 102 | <1 . . . 1725 |
| M107 | DJ167A19: hypothetical protein DJ167A19.1 | 103 | 104 | 1 . . . 921 |
| M108 | DKFZP564D166: putative ankyrin-repeat containing protein | 105 | 106 | 95 . . . 3400 |
| M82 | DKFZp564I1922: adlican | 109 | 110 | 1 . . . 8487 |
| M110 | DKFZP566I133: hypothetical protein DKFZp566I133, variant 1 | 111 | 112 | 134 . . . 1354 |
| M554 | DKFZP566I133: hypothetical protein DKFZp566I133, variant 2 | 113 | 114 | 134 . . . 1354 |
| M111 | DNAJL1: hypothetical protein similar to mouse Dnajl1 | 115 | 116 | 203 . . . 1225 |
| M555 | DUSP4: dual specificity phosphatase 4 | 119 | 120 | 502 . . . 1686 |
| M210 | EDIL3: EGF-like repeats and discoidin I-like domains 3 | 121 | 122 | 111 . . . 1553 |
| M114 | ESR1: estrogen receptor 1 | 127 | 128 | 361 . . . 2148 |
| M118 | FAP: fibroblast activation protein, alpha | 135 | 136 | 209 . . . 2491 |
| M119 | FKBP4: FK506-binding protein 4 | 139 | 140 | 100 . . . 1479 |
| M212 | FKSG12: pancreas tumor-related protein | 141 | 142 | 238 . . . 1125 |

TABLE 5-continued

| Marker | Gene Name | SEQ ID NO (nts) | SEQ ID NO (AAs) | CDS |
|---|---|---|---|---|
| M120 | FLJ12425: hypothetical protein FLJ12425 | 143 | 144 | 42 ... 335 |
| M121 | FLJ12910: hypothetical protein FLJ12910 | 145 | 146 | 260 ... 1585 |
| M122 | FLJ13187: hypothetical protein FLJ13187 | 147 | 148 | 98 ... 847 |
| M123 | FLJ14103: hypothetical protein FLJ14103 | 149 | 150 | 76 ... 624 |
| M398 | FLJ20171: hypothetical protein FLJ20171 | 151 | 152 | 58 ... 1134 |
| M124 | FLJ21213: hypothetical protein FLJ21213 | 157 | 158 | 3 ... 809 |
| M125 | FLJ21879: hypothetical protein FLJ21879 | 159 | 160 | 75 ... 1043 |
| M126 | FLJ22002: hypothetical protein FLJ22002 | 161 | 162 | 116 ... 784 |
| M213 | FXYD3: FXYD domain-containing ion transport regulator 3, isoform 1 | 165 | 166 | 176 ... 439 |
| M214 | FXYD3: FXYD domain-containing ion transport regulator 3, isoform 2 | 167 | 168 | 260 ... 601 |
| M127 | G1P3: interferon, alpha-inducible protein (clone IFI-6-16) | 169 | 170 | 108 ... 500 |
| M216 | GATA3: GATA-binding protein 3, variant 1 | 175 | 176 | 461 ... 1792 |
| M217 | GATA3: GATA-binding protein 3, variant 2 | 177 | 176 | 461 ... 1792 |
| M218 | GATA3: GATA-binding protein 3, variant 3 | 178 | 176 | 152 ... 1483 |
| M271 | GOLPH2: golgi phosphoprotein 2 | 183 | 184 | 151 ... 1353 |
| M219 | GPD2: glycerol-3-phosphate dehydrogenase 2 (mitochondrial) | 185 | 186 | 124 ... 2307 |
| M132 | GRIA2: glutamate receptor, ionotropic, AMPA 2 | 189 | 190 | 161 ... 2812 |
| M199 | HAG-2: anterior gradient 2 (*Xenopus laevis*) homolog | 199 | 200 | 59 ... 586 |
| M196 | HAG-3: anterior gradient protein 3, variant 1 | 201 | 202 | 49 ... 549 |
| M225 | HAG-3: anterior gradient protein 3, variant 2 | 203 | 204 | 116 ... 129 |
| M223 | HNF3A: hepatocyte nuclear factor 3, alpha | 211 | 212 | 88 ... 1509 |
| M135 | HOXB2: homeo box B2 | 213 | 214 | 79 ... 1149 |
| M224 | HSPC155: hypothetical protein HSPC155 | 221 | 222 | 241 ... 744 |
| M403 | IGF1R: insulin-like growth factor 1 receptor | 225 | 226 | 46 ... 4149 |
| M34 | INHBA: Inhibin, beta-1 (activin A, activin AB alpha polypeptide) | 231 | 232 | 86 ... 1366 |
| M140 | ISG15: interferon-stimulated protein, 15 kDa | 233 | 234 | 76 ... 573 |
| M226 | JCL-1: hepatocellular carcinoma associated protein; breast cancer associated gene 1 | 235 | 236 | 70 ... 1890 |
| M556 | JUN: v-jun avian sarcoma virus 17 oncogene homolog | 237 | 238 | 975 ... 1970 |
| M141 | KIAA0215: KIAA0215 protein | 239 | 240 | 299 ... 2770 |
| M227 | KIAA0878: KIAA0878 protein | 241 | 242 | 336 ... 2171 |
| M228 | KIAA0882: KIAA0882 protein | 243 | 244 | <1 ... 2776 |
| M143 | KIAA1051: KIAA1051 protein | 245 | 246 | <1 ... 1030 |
| M405 | KIAA1077: KIAA1077 protein | 247 | 248 | 267 ... 2882 |
| M557 | KIAA1181: KIAA1181 protein | 249 | 250 | <1 ... 1012 |
| M146 | KIAA1598: KIAA1598 protein | 255 | 256 | 111 ... 488 |
| M147 | KRT8: Keratin-8 | 257 | 258 | 60 ... 1511 |
| M149 | LIV-1: LIV-1 protein, estrogen regulated | 263 | 264 | 138 ... 2387 |
| M559 | LPHB: lipophilin B (uteroglobin family member), prostatein-like | 271 | 272 | 64 ... 336 |
| M560 | MGB1: mammaglobin 1 | 277 | 278 | 61 ... 342 |
| M458 | MGB2: mammaglobin 2 | 279 | 280 | 65 ... 352 |
| M154 | MGC10765: hypothetical protein MGC10765 | 281 | 282 | 14 ... 679 |
| M155 | MGC2771: hypothetical protein MGC2771 | 283 | 284 | 185 ... 1987 |
| M231 | MGC3038: hypothetical protein MGC3038 similar to actin related protein 2/3 complex, subunit 5 | 285 | 286 | 87 ... 548 |
| M232 | MGC3077: hypothetical protein MGC3077 | 287 | 288 | 137 ... 703 |
| M47 | MGP: matrix Gla protein | 291 | 292 | 47 ... 358 |
| M156 | MIG: monokine induced by gamma interferon | 293 | 294 | 40 ... 417 |
| M157 | MLN64: steroidogenic acute regulatory protein related | 295 | 296 | 122 ... 1459 |
| M158 | MMP11: matrix metalloproteinase 11 preproprotein; stromelysin 3 | 297 | 298 | 23 ... 1489 |
| M160 | MYCBP: c-myc binding protein | 312 | 313 | 39 ... 350 |
| M161 | MYO6: myosin VI | 316 | 317 | 140 ... 3997 |
| M162 | NAT1: N-acetyltransferase 1 (arylamine N-acetyltransferase) | 318 | 319 | 1 ... 873 |
| M163 | NAT1: N-acetyltransferase 1 (arylamine N-acetyltransferase), NAT1*11B allele | 320 | 319 | 441 ... 1313 |
| M561 | NDUFA8: NADH dehydrogenase (ubiquinone) 1 alpha subcomplex, 8 (19 kD, PGIV) | 325 | 326 | 68 ... 586 |
| M164 | NET-6: tetraspan NET-6 protein | 327 | 328 | 163 ... 777 |
| M165 | NPY1R: neuropeptide Y receptor Y1 | 329 | 330 | 209 ... 1363 |
| M236 | NY-BR-1.1: breast cancer antigen NY-BR-1.1 | 331 | 332 | 181 ... 3858 |
| M235 | NY-BR-1: breast cancer antigen NY-BR-1 | 333 | 334 | 100 ... 4125 |
| OV48 | OPN-a: Secreted phosphoprotein-1 (osteopontin, bone sialoprotein) | 335 | 336 | 1 ... 942 |
| OV49 | OPN-b: Secreted phosphoprotein-1 (osteopontin, bone sialoprotein) | 337 | 338 | 88 ... 990 |

TABLE 5-continued

| Marker | Gene Name | SEQ ID NO (nts) | SEQ ID NO (AAs) | CDS |
|---|---|---|---|---|
| OV50 | OPN-c: Secreted phosphoprotein-1 (osteopontin, bone sialoprotein) | 339 | 340 | 1 . . . 861 |
| M56 | OSF-2: osteoblast specific factor 2 (fasciclin I-like) | 341 | 342 | 12 . . . 2522 |
| M176 | P4HB: procollagen-proline, 2-oxoglutarate 4-dioxygenase (proline 4-hydroxylase), beta polypeptide (protein disulfide isomerase; thyroid hormone binding protein p55) | 343 | 344 | 30 . . . 1556 |
| M166 | PAFAH1B3: platelet-activating factor acetylhydrolase, isoform Ib, gamma subunit | 345 | 346 | 114 . . . 809 |
| M409 | PAR6B: PAR-6 beta | 347 | 348 | 1 . . . 1119 |
| M410 | PC4: activated RNA polymerase II: transcription cofactor 4 | 349 | 350 | 1 . . . 384 |
| M167 | PCSK1: proprotein convertase subtilisin/kexin type 1 | 351 | 352 | 190 . . . 2451 |
| M411 | PCTA-1: prostate carcinoma tumor antigen | 353 | 354 | 55 . . . 1007 |
| M412 | PDCD9: programmed cell death 9 | 355 | 356 | 39 . . . 1358 |
| M562 | PIP: prolactin-induced protein | 357 | 358 | 37 . . . 477 |
| M168 | PKIB: protein kinase (cAMP-dependent, catalytic) inhibitor beta | 359 | 360 | 112 . . . 348 |
| M414 | PLAUR: plasminogen activator, urokinase receptor | 361 | 362 | 427 . . . 1434 |
| M169 | PLU-1: putative DNA/chromatin binding motif | 363 | 364 | 90 . . . 4724 |
| M172 | PPIF: peptidylprolyl isomerase F (cyclophilin F), variant 2 | 369 | 368 | 84 . . . 707 |
| M174 | PRLR: prolactin receptor | 372 | 373 | 285 . . . 2153 |
| M175 | PRO2000: PRO2000 protein | 374 | 375 | 651 . . . 1739 |
| M415 | PTP4A2: protein tyrosine phosphatase type IVA, member 2 | 384 | 385 | 424 . . . 927 |
| M416 | RAB22B: small GTP-binding protein RAB22B | 386 | 387 | 129 . . . 716 |
| M417 | RAB27B: RAB27B, member RAS oncogene family | 388 | 389 | 93 . . . 749 |
| M179 | RAB5EP: rabaptin-5 | 390 | 391 | 189 . . . 2777 |
| M238 | RNB6: RNB6 protein, variant 1 | 400 | 401 | 62 . . . 1318 |
| M419 | SCYB10: small inducible cytokine subfamily B (Cys-X-Cys), member 10 | 412 | 413 | 67 . . . 363 |
| M563 | SEMA3E: sema domain, immunoglobulin domain (Ig), short basic domain, secreted, (semaphorin) 3E | 414 | 415 | 467 . . . 2794 |
| M240 | SERPINA3: serine (or cysteine) proteinase inhibitor, clade A (alpha-1 antiproteinase, antitrypsin), member 3 | 420 | 421 | 26 . . . 1327 |
| M564 | SHARP: SMART/HDAC1 associated repressor protein | 422 | 423 | 205 . . . 11199 |
| M241 | SIAH2: seven in absentia (Drosophila) homolog 2, variant 1 | 424 | 425 | 527 . . . 1501 |
| M619 | SIAH2: seven in absentia (Drosophila) homolog 2, variant 2 | 426 | 425 | 527 . . . 1501 |
| M184 | SLC9A3R1: solute carrier family 9 (sodium/hydrogen exchanger), isoform 3 regulatory factor 1 | 427 | 428 | 213 . . . 1289 |
| M186 | SPN: asporin (LRR class 1) | 432 | 433 | 247 . . . 810 |
| M423 | SQLE: squalene epoxidase | 434 | 435 | 876 . . . 2600 |
| M426 | STC2: stanniocalcin 2 | 442 | 443 | 135 . . . 1043 |
| M188 | STHM: sialyltransferase | 444 | 445 | 40 . . . 1164 |
| M565 | SYTL2: synaptotagmin-like 2 | 446 | 447 | 261 . . . 1766 |
| M566 | SYTL2: synaptotagmin-like 2, isoform a | 448 | 449 | 572 . . . 3304 |
| M567 | SYTL2: synaptotagmin-like 2, isoform b | 450 | 451 | 690 . . . 1820 |
| M190 | TDP52: tumor protein D52 | 454 | 455 | 92 . . . 646 |
| M568 | TFAP2A: transcription factor AP-2 alpha (activating enhancer-binding protein 2 alpha), variant 1 | 456 | 457 | 282 . . . 1601 |
| M569 | TFAP2A: transcription factor AP-2 alpha (activating enhancer-binding protein 2 alpha), variant 2 | 458 | 457 | 282 . . . 1601 |
| M620 | TFAP2B: transcription factor AP-2 beta (activating enhancer binding protein 2 beta), variant 1 | 459 | 460 | 257 . . . 1639 |
| M621 | TFAP2B: transcription factor AP-2 beta (activating enhancer binding protein 2 beta), variant 2 | 461 | 462 | 257 . . . 1666 |
| M242 | TFF1: trefoil factor 1 (breast cancer, estrogen-inducible sequence expressed in) | 463 | 464 | 41 . . . 295 |
| M243 | TFF3: trefoil factor 3 (intestinal), variant 1 | 465 | 466 | 2 . . . 226 |
| M682 | TFF3: trefoil factor 3 (intestinal), variant 2 | 467 | 468 | 128 . . . 520 |
| M192 | TRPS1: trichorhinophalangeal syndrome I | 471 | 472 | 639 . . . 4484 |
| M427 | UGDH: UDP-glucose dehydrogenase | 473 | 474 | 79 . . . 1563 |
| M193 | unnamed gene (1) | 475 | 476 | 75 . . . 1697 |
| M194 | unnamed gene (2) | 477 | 478 | 23 . . . 1066 |
| M420 | unnamed gene (5) | 483 | 484 | 203 . . . 1951 |
| M428 | unnamed gene (6), variant 1 | 485 | 486 | 75 . . . 2471 |
| M429 | unnamed gene (6), variant 2 | 487 | 488 | 75 . . . 1535 |
| M622 | unnamed gene (7) | 489 | 490 | 579 à 803 |
| M93 | unnamed gene (CASB619), variant 1 | 491 | 492 | 310 . . . 3351 |
| M94 | unnamed gene (CASB619), variant 2 | 493 | 494 | 310 . . . 3324 |
| M138 | unnamed gene (HSECP) | 495 | 496 | 27 . . . 863 |
| M195 | VAV3: vav 3 oncogene | 497 | 498 | 48 . . . 2591 |

TABLE 5-continued

| Marker | Gene Name | SEQ ID NO (nts) | SEQ ID NO (AAs) | CDS |
|---|---|---|---|---|
| OV25 | WFDC2: Epididymis-specific, whey-acidic protein type, four-disulfide core | 499 | 500 | 28...405 |
| M197 | XBP1: X-box binding protein 1, variant 1 | 501 | 502 | 49...834 |
| M244 | XBP1: X-box binding protein 1, variant 2 | 503 | 504 | 49...834 |

TABLE 6

| Marker | Gene Name | SEQ ID NO (nts) | SEQ ID NO (AAs) | CDS |
|---|---|---|---|---|
| M83 | AKR1C1: aldo-keto reductase family 1, member C1 (20-alpha (3-alpha)-hydroxysteroid dehydrogenase) | 3 | 4 | 7...978 |
| M84 | AKR1C3: aldo-keto reductase family 1, member C3 (3-alpha hydroxysteroid dehydrogenase, type II) | 5 | 6 | 1...972 |
| M86 | AQP3: Aquaporin 3, variant 1 | 9 | 10 | 65...943 |
| M87 | AQP3: Aquaporin 3, variant 2 | 11 | 10 | 65...943 |
| M391 | ARHGEF12: Rho guanine exchange factor (GEF) 12 | 14 | 15 | 8...4642 |
| M672 | ASS: argininosuccinate synthetase, transcript variant 1 | 16 | 17 | 76...1314 |
| M673 | ASS: argininosuccinate synthetase, transcript variant 2 | 18 | 19 | 81...1319 |
| M200 | ATP5A1: ATP synthase, H+ transporting, mitochondrial F1 complex, alpha subunit, isoform 1, cardiac muscle | 20 | 21 | 59...1720 |
| M392 | BAK1: BCL2-antagonist/killer 1 | 24 | 25 | 201...836 |
| M394 | C1orf21: chromosome 1 open reading frame 21 | 32 | 33 | 400...765 |
| M202 | CALM1: calmodulin 1 (phosphorylase kinase, delta) | 34 | 35 | 200...649 |
| M367 | CD24: CD24 antigen (small cell lung carcinoma cluster 4 antigen) | 38 | 39 | 57...299 |
| M95 | CDC2: cell division cycle 2, G1 to S and G2 to M | 40 | 41 | 127...1020 |
| M254 | CGI-96: CGI-96 protein | 52 | 53 | 175...1146 |
| M104 | CrkRS: CDC2-related protein kinase 7 | 85 | 86 | 34...4506 |
| M395 | CSK: c-src tyrosine kinase | 87 | 88 | 413...1765 |
| M396 | CYP1B1: cytochrome P450, subfamily I (dioxin-inducible), polypeptide 1 | 95 | 96 | 373...2004 |
| M106 | CYP24: cytochrome P450, subfamily XXIV (vitamin D 24-hydroxylase) | 97 | 98 | 405...1946 |
| M109 | DKFZP564D206: hypothetical protein DKFZP564D206 | 107 | 108 | <1...405 |
| M112 | DRIL1: dead ringer (Drosophila)-like 1 | 117 | 118 | 201...1982 |
| M211 | ENO1: enolase 1, (alpha) | 123 | 124 | 95...1399 |
| M113 | ERBB2: v-erb-b2 avian erythroblastic leukemia viral oncogene homolog 2 (neuro/glioblastoma derived oncogene homolog) | 125 | 126 | 151...3919 |
| M114 | ESR1: estrogen receptor 1 | 127 | 128 | 361...2148 |
| M115 | F2R: coagulation factor II (thrombin) receptor | 129 | 130 | 345...1622 |
| M116 | FABP7: B-FABP, fatty acid binding protein 7 | 131 | 132 | 77...475 |
| M117 | FACL2: fatty-acid-Coenzyme A ligase, long-chain 2 | 133 | 134 | 14...2110 |
| M397 | FGF7: fibroblast growth factor 7 (keratinocyte growth factor) | 137 | 138 | 446...1030 |
| M514 | FLJ20940: hypothetical protein FLJ20940 | 153 | 154 | 236...742 |
| M399 | FLJ21174: hypothetical protein FLJ21174 | 155 | 156 | 234...881 |
| M400 | FLJ22418: hypothetical protein FLJ22418 | 163 | 164 | 71...919 |
| M215 | GABRP: gamma-aminobutyric acid (GABA) A receptor, pi | 171 | 172 | 157...1479 |
| M128 | GATA2: GATA-binding protein 2 | 173 | 174 | 194...1618 |
| M216 | GATA3: GATA-binding protein 3, variant 1 | 175 | 176 | 461...1792 |
| M217 | GATA3: GATA-binding protein 3, variant 2 | 177 | 176 | 461...1792 |
| M218 | GATA3: GATA-binding protein 3, variant 3 | 178 | 176 | 152...1483 |
| M129 | GNLY: granulysin, isoform 5199 | 179 | 180 | 281...670 |
| M130 | GNLY: granulysin, isoform NKG5 | 181 | 182 | 129...566 |
| M131 | GPI: glucose phosphate isomerase | 187 | 188 | 16...1692 |
| M495 | GSTP1: glutathione S-transferase pi | 191 | 192 | 30...662 |
| M220 | GUCY1A3: guanylate cyclase 1, soluble, alpha 3, variant 1 | 193 | 194 | 520...2592 |
| M221 | GUCY1A3: guanylate cyclase 1, soluble, alpha 3, variant 2 | 195 | 194 | 386...2458 |
| M222 | GUCY1A3: guanylate cyclase 1, soluble, alpha 3, variant 3 | 196 | 194 | 407...2479 |
| M133 | GZMA: Granzyme A (Cytotoxic T-lymphocyte-associated serine esterase-3; Hanukah factor serine protease); CTL tryptase | 197 | 198 | 39...827 |
| M196 | HAG-3: anterior gradient protein 3, variant 1 | 201 | 202 | 49...549 |
| M134 | HDAC2: histone deacetylase 2 | 205 | 206 | 205...1671 |

TABLE 6-continued

| Marker | Gene Name | SEQ ID NO (nts) | SEQ ID NO (AAs) | CDS |
|---|---|---|---|---|
| M273 | HMGCS2: 3-hydroxy-3-methylglutaryl-Coenzyme A synthase 2 (mitochondrial) | 207 | 208 | 52 . . . 1578 |
| M674 | HN1: hematological and neurological expressed 1 | 209 | 210 | 104 . . . 568 |
| M136 | HPD: 4-hydroxyphenylpyruvate dioxygenase | 215 | 216 | 28 . . . 1207 |
| M137 | HPGD: hydroxyprostaglandin dehydrogenase 15-(NAD) | 217 | 218 | 18 . . . 818 |
| M401 | HSCP1: serine carboxypeptidase 1 precursor protein | 219 | 220 | 33 . . . 1391 |
| M402 | HSPD1: heat shock 60 kD protein 1 (chaperonin) | 223 | 224 | 25 . . . 1746 |
| M139 | IGSF1: IGCD1, IGDC1, KIAA036, immunoglobulin superfamily, member 1 | 227 | 228 | 81 . . . 4091 |
| M404 | IL6ST: interleukin 6 signal transducer (gp130, oncostatin M receptor) | 229 | 230 | 256 . . . 3012 |
| M144 | KIAA1277: KIAA1277 protein | 251 | 252 | <5 . . . 3079 |
| M145 | KIAA1361: KIAA1361 protein | 253 | 254 | <141 . . . 3158 |
| M148 | LBP: lipopolysaccharide-binding protein | 259 | 260 | 18 . . . 1463 |
| M229 | LDHB: lactate dehydrogenase B | 261 | 262 | 85 . . . 1089 |
| M558 | LOC118430: small breast epithelial mucin | 265 | 266 | 69 . . . 341 |
| M406 | LOC51242: hypothetical protein LOC51242 | 267 | 268 | 1 . . . 435 |
| M230 | LOC57402: S100-type calcium binding protein A14 | 269 | 270 | 99 . . . 413 |
| M152 | MDS024: MDS024 protein | 273 | 274 | 65 . . . 838 |
| M153 | ME1: malic enzyme 1, NADP(+)-dependent, cytosolic | 275 | 276 | 108 . . . 1826 |
| M675 | MGC9753: hypothetical protein MGC9753 | 289 | 290 | 1092 . . . 1814 |
| M156 | MIG: monokine induced by gamma interferon | 293 | 294 | 40 . . . 417 |
| M157 | MLN64: steroidogenic acute regulatory protein related | 295 | 296 | 122 . . . 1459 |
| M158 | MMP11: matrix metalloproteinase 11 preproprotein; stromelysin 3 | 297 | 298 | 23 . . . 1489 |
| OV52 | MMP7: matrix metalloproteinase 7 (matrilysin, uterine) | 299 | 300 | 28 . . . 831 |
| M407 | MS4A7: membrane-spanning 4-domains, subfamily A, member 7, variant 1 | 301 | 302 | 147 . . . 869 |
| M676 | MS4A7: membrane-spanning 4-domains, subfamily A, member 7, variant 2 | 303 | 302 | 118 . . . 840 |
| M150 | MSC: mitochondrial solute carrier, hypothetical protein PRO1278; HT015 protein | 304 | 305 | 368 . . . 652 |
| M151 | MST4: serine/threonine protein kinase MASK | 306 | 307 | 118 . . . 1368 |
| M159 | MTHFD2: methylene tetrahydrofolate dehydrogenase (NAD+ dependent), methenyltetrahydrofolate cyclohydrolase | 308 | 309 | 16 . . . 1050 |
| M669 | MUC1: mucin 1, transmembrane | 310 | 311 | 74 . . . 3841 |
| M233 | MYO5A: myosin VA (heavy polypeptide 12, myoxin) | 314 | 315 | 251 . . . 5818 |
| M162 | NAT1: N-acetyltransferase 1 (arylamine N-acetyltransferase) | 318 | 319 | 1 . . . 873 |
| M163 | NAT1: N-acetyltransferase 1 (arylamine N-acetyltransferase), NAT1*11B allele | 320 | 319 | 441 . . . 1313 |
| M677 | NCALD: neurocalcin delta | 321 | 322 | 121 . . . 702 |
| M408 | NDRG1: N-myc downstream regulated protein | 323 | 324 | 111 . . . 1295 |
| M165 | NPY1R: neuropeptide Y receptor Y1 | 329 | 330 | 209 . . . 1363 |
| OV48 | OPN-a: Secreted phosphoprotein-1 (osteopontin, bone sialoprotein) | 335 | 336 | 1 . . . 942 |
| OV49 | OPN-b: Secreted phosphoprotein-1 (osteopontin, bone sialoprotein) | 337 | 338 | 88 . . . 990 |
| OV50 | OPN-c: Secreted phosphoprotein-1 (osteopontin, bone sialoprotein) | 339 | 340 | 1 . . . 861 |
| M170 | PPARBP, PPAR binding protein, thyroid hormone receptor interactor 2; PPARG binding protein | 365 | 366 | 236 . . . 4936 |
| M171 | PPIF: peptidylprolyl isomerase F (cyclophilin F), variant 1 | 367 | 368 | 72 . . . 695 |
| M173 | PPIF: peptidylprolyl isomerase F (cyclophilin F), variant 3 | 370 | 371 | 84 . . . 659 |
| M177 | PROML1: prominin (mouse)-like 1; hematopoietic stem cell antigen | 376 | 377 | 38 . . . 2635 |
| M237 | PSMB3: proteasome (prosome, macropain) subunit, beta type, 3 | 378 | 379 | 18 . . . 635 |
| M678 | PSMB9: proteasome (prosome, macropain) subunit, beta type, 9 (large multifunctional protease 2) | 380 | 381 | 41 . . . 700 |
| M178 | PSMD3: proteasome (prosome, macropain) 26S subunit, non-ATPase, 3 | 382 | 383 | 158 . . . 1762 |
| M180 | RAMP3: receptor (calcitonin) activity modifying protein 3 precursor; calcitonin receptor-like receptor activity modifying protein 3 | 392 | 393 | 30 . . . 476 |
| M679 | RARRES1: retinoic acid receptor responder (tazarotene induced) 1, variant 1 | 394 | 395 | 37 . . . 723 |
| M680 | RARRES1: retinoic acid receptor responder (tazarotene induced) 1, variant 2 | 396 | 397 | 128 . . . 1012 |

TABLE 6-continued

| Marker | Gene Name | SEQ ID NO (nts) | SEQ ID NO (AAs) | CDS |
|---|---|---|---|---|
| M91 | RASGRP1: RAS guanyl releasing protein 1 (calcium and DAG-regulated) | 398 | 399 | <1...2351 |
| M418 | RNB6: RNB6 protein, variant 2 | 402 | 403 | 125...1285 |
| M181 | RPL19: ribosomal protein L19 | 404 | 405 | 29...619 |
| M182 | RQCD1: rodi (required for cell differentiation, S. pombe) homolog 1 | 406 | 407 | 1...900 |
| M183 | S100A8: S100 calcium-binding protein A8 | 408 | 409 | 56...340 |
| M239 | SCD: stearoyl-CoA desaturase (delta-9-desaturase) | 410 | 411 | 236...1315 |
| M421 | SERHL: kraken-like, variant 1 | 416 | 417 | 118...1062 |
| M422 | SERHL: kraken-like, variant 2 | 418 | 419 | 82...693 |
| M185 | SLPI: secretory leukocyte protease inhibitor (antileukoproteinase), variant 1 | 429 | 430 | 19...417 |
| M681 | SLPI: secretory leukocyte protease inhibitor (antileukoproteinase), variant 2 | 431 | 430 | 23...421 |
| M424 | STAT4: signal transducer and activator of transcription 4, variant 1 | 436 | 437 | 82...1353 |
| M425 | STAT4: signal transducer and activator of transcription 4, variant 2 | 438 | 439 | 82...2328 |
| M187 | STC1: stanniocalcin 1 | 440 | 441 | 285...1028 |
| M189 | TAF1C: TATA box binding protein (TBP)-associated factor, RNA polymerase I, C, 110 kD | 452 | 453 | 185...2794 |
| M242 | TFF1: trefoil factor 1 (breast cancer, estrogen-inducible sequence expressed in) | 463 | 464 | 41...295 |
| M191 | TLN1: talin 1 | 469 | 470 | 127...7752 |
| M427 | UGDH: UDP-glucose dehydrogenase | 473 | 474 | 79...1563 |
| M194 | unnamed gene (2) | 477 | 478 | 23...1066 |
| M234 | unnamed gene (3) | 479 | 480 | 55...676 |
| M393 | unnamed gene (4) | 481 | 482 | 287...406 |
| M198 | ZNF217: zinc finger protein 217 | 505 | 506 | 272...3418 |

TABLE 7

| Marker | Gene Name | SEQ ID NO (nts) | SEQ ID NO (AAs) | CDS |
|---|---|---|---|---|
| M114 | ESR1: estrogen receptor 1 | 127 | 128 | 361...2148 |
| M216 | GATA3: GATA-binding protein 3, variant 1 | 175 | 176 | 461...1792 |
| M217 | GATA3: GATA-binding protein 3, variant 2 | 177 | 176 | 461...1792 |
| M218 | GATA3: GATA-binding protein 3, variant 3 | 178 | 176 | 152...1483 |
| M196 | HAG-3: anterior gradient protein 3, variant 1 | 201 | 202 | 49...549 |
| M156 | MIG: monokine induced by gamma interferon | 293 | 294 | 40...417 |
| M158 | MMP11: matrix metalloproteinase 11 preproprotein; stromelysin 3 | 297 | 298 | 23...1489 |
| M162 | NAT1: N-acetyltransferase 1 (arylamine N-acetyltransferase) | 318 | 319 | 1...873 |
| M163 | NAT1: N-acetyltransferase 1 (arylamine N-acetyltransferase), NAT1*11B allele | 320 | 319 | 441...1313 |
| M165 | NPY1R: neuropeptide Y receptor Y1 | 329 | 330 | 209...1363 |
| OV48 | OPN-a: Secreted phosphoprotein-1 (osteopontin, bone sialoprotein) | 335 | 336 | 1...942 |
| OV49 | OPN-b: Secreted phosphoprotein-1 (osteopontin, bone sialoprotein) | 337 | 338 | 88...990 |
| OV50 | OPN-c: Secreted phosphoprotein-1 (osteopontin, bone sialoprotein) | 339 | 340 | 1...861 |
| M242 | TFF1: trefoil factor 1 (breast cancer, estrogen-inducible sequence expressed in) | 463 | 464 | 41...295 |
| M427 | UGDH: UDP-glucose dehydrogenase | 473 | 474 | 79...1563 |
| M194 | unnamed gene (2) | 477 | 478 | 23...1066 |

TABLE 8

| Marker | Gene Name | SEQ ID NO (nts) | SEQ ID NO (AAs) | CDS |
|---|---|---|---|---|
| M394 | C1orf21: chromosome 1 open reading frame 21 | 32 | 33 | 400...765 |
| M106 | CYP24: cytochrome P450, subfamily XXIV (vitamin D 24-hydroxylase) | 97 | 98 | 405...1946 |
| M112 | DRIL1: dead ringer (Drosophila)-like 1 | 117 | 118 | 201...1982 |
| M114 | ESR1: estrogen receptor 1 | 127 | 128 | 361...2148 |
| M399 | FLJ21174: hypothetical protein FLJ21174 | 155 | 156 | 234...881 |
| M400 | FLJ22418: hypothetical protein FLJ22418 | 163 | 164 | 71...919 |
| M216 | GATA3: GATA-binding protein 3, variant 1 | 175 | 176 | 461...1792 |
| M217 | GATA3: GATA-binding protein 3, variant 2 | 177 | 176 | 461...1792 |
| M218 | GATA3: GATA-binding protein 3, variant 3 | 178 | 176 | 152...1483 |

TABLE 8-continued

| Marker | Gene Name | SEQ ID NO (nts) | SEQ ID NO (AAs) | CDS |
|---|---|---|---|---|
| M220 | GUCY1A3: guanylate cyclase 1, soluble, alpha 3, variant 1 | 193 | 194 | 520...2592 |
| M221 | GUCY1A3: guanylate cyclase 1, soluble, alpha 3, variant 2 | 195 | 194 | 386...2458 |
| M222 | GUCY1A3: guanylate cyclase 1, soluble, alpha 3, variant 3 | 196 | 194 | 407...2479 |
| M273 | HMGCS2: 3-hydroxy-3-methylglutaryl-Coenzyme A synthase 2 (mitochondrial) | 207 | 208 | 52...1578 |
| M136 | HPD: 4-hydroxyphenylpyruvate dioxygenase | 215 | 216 | 26...1207 |
| M137 | HPGD: hydroxyprostaglandin dehydrogenase 15- (NAD) | 217 | 218 | 18...818 |
| M404 | IL6ST: interleukin 6 signal transducer (gp130, oncostatin M receptor) | 229 | 230 | 256...3012 |
| M229 | LDHB: lactate dehydrogenase B | 261 | 262 | 85...1089 |
| M676 | MS4A7: membrane-spanning 4-domains, subfamily A, member 7, variant 2 | 303 | 302 | 118...840 |
| M162 | NAT1: N-acetyltransferase 1 (arylamine N-acetyltransferase) | 318 | 319 | 1...873 |
| M163 | NAT1: N-acetyltransferase 1 (arylamine N-acetyltransferase), NAT1*11B allele | 320 | 319 | 441...1313 |
| M677 | NCALD: neurocalcin delta | 321 | 322 | 121...702 |
| M91 | RASGRP1: RAS guanyl releasing protein 1 (calcium and DAG-regulated) | 398 | 399 | <1...2351 |
| M418 | RNB6: RNB6 protein, variant 2 | 402 | 403 | 125...1285 |
| M182 | RQCD1: rcd1 (required for cell differentiation, S. pombe) homolog 1 | 406 | 407 | 1...900 |
| M189 | TAF1C: TATA box binding protein (TBP)-associated factor, RNA polymerase I, C, 110 kD | 452 | 453 | 185...2794 |
| M242 | TFF1: trefoil factor 1 (breast cancer, estrogen-inducible sequence expressed in) | 463 | 464 | 41...295 |
| M427 | UGDH: UDP-glucose dehydrogenase | 473 | 474 | 79...1563 |
| M194 | unnamed gene (2) | 477 | 478 | 23...1066 |
| M393 | unnamed gene (4) | 481 | 482 | 287...406 |
| M198 | ZNF217: zinc finger protein 217 | 505 | 506 | 272...3418 |

TABLE 9

| Marker | Gene Name | SEQ ID NO (nts) | SEQ ID NO (AAs) | CDS |
|---|---|---|---|---|
| M83 | AKR1C1: aldo-keto reductase family 1, member C1 (20-alpha (3-alpha)-hydroxysteroid dehydrogenase) | 3 | 4 | 7...978 |
| M84 | AKR1C3: aldo-keto reductase family 1, member C3 (3-alpha hydroxysteroid dehydrogenase, type II) | 5 | 6 | 1...972 |
| M86 | AQP3: Aquaporin 3, variant 1 | 9 | 10 | 65...943 |
| M87 | AQP3: Aquaporin 3, variant 2 | 11 | 10 | 65...943 |
| M391 | ARHGEF12: Rho guanine exchange factor (GEF) 12 | 14 | 15 | 8...4642 |
| M672 | ASS: argininosuccinate synthetase, transcript variant 1 | 16 | 17 | 76...1314 |
| M673 | ASS: argininosuccinate synthetase, transcript variant 2 | 18 | 19 | 81...1319 |
| M200 | ATP5A1: ATP synthase, H+ transporting, mitochondrial F1 complex, alpha subunit, isoform 1, cardiac muscle | 20 | 21 | 59...1720 |
| M392 | BAK1: BCL2-antagonist/killer 1 | 24 | 25 | 201...836 |
| M202 | CALM1: calmodulin 1 (phosphorylase kinase, delta) | 34 | 35 | 200...649 |
| M367 | CD24: CD24 antigen (small cell lung carcinoma cluster 4 antigen) | 38 | 39 | 57...299 |
| M95 | CDC2: cell division cycle 2, G1 to S and G2 to M | 40 | 41 | 127...1020 |
| M254 | CGI-96: CGI-96 protein | 52 | 53 | 175...1146 |
| M104 | CrkRS: CDC2-related protein kinase 7 | 85 | 86 | 34...4506 |
| M395 | CSK: c-src tyrosine kinase | 87 | 88 | 413...1765 |
| M396 | CYP1B1: cytochrome P450, subfamily I (dioxin-inducible), polypeptide 1 | 95 | 96 | 373...2004 |
| M109 | DKFZP564D206: hypothetical protein DKFZP564D206 | 107 | 108 | <1...405 |
| M211 | ENO1: enolase 1, (alpha) | 123 | 124 | 95...1399 |
| M113 | ERBB2: v-erb-b2 avian erythroblastic leukemia viral oncogene homolog 2 (neuro/glioblastoma derived oncogene homolog) | 125 | 126 | 151...3919 |
| M115 | F2R: coagulation factor II (thrombin) receptor | 129 | 130 | 345...1622 |
| M116 | FABP7: B-FABP, fatty acid binding protein 7 | 131 | 132 | 77...475 |

TABLE 9-continued

| Marker | Gene Name | SEQ ID NO (nts) | SEQ ID NO (AAs) | CDS |
|---|---|---|---|---|
| M117 | FACL2: fatty-acid-Coenzyme A ligase, long-chain 2 | 133 | 134 | 14 ... 2110 |
| M397 | FGF7: fibroblast growth factor 7 (keratinocyte growth factor) | 137 | 138 | 446 ... 1030 |
| M514 | FLJ20940: hypothetical protein FLJ20940 | 153 | 154 | 236 ... 742 |
| M215 | GABRP: gamma-aminobutyric acid (GABA) A receptor, pi | 171 | 172 | 157 ... 1479 |
| M128 | GATA2: GATA-binding protein 2 | 173 | 174 | 194 ... 1618 |
| M129 | GNLY: granulysin, isoform 519 | 179 | 180 | 281 ... 670 |
| M130 | GNLY: granulysin, isoform NKG5 | 181 | 182 | 129 ... 566 |
| M131 | GPI: glucose phosphate isomerase | 187 | 188 | 16 ... 1692 |
| M495 | GSTP1: glutathione S-transferase pi | 191 | 192 | 30 ... 662 |
| M133 | GZMA: Granzyme A (Cytotoxic T-lymphocyte-associated serine esterase-3; Hanukah factor serine protease); CTL tryptase | 197 | 198 | 39 ... 827 |
| M196 | HAG-3: anterior gradient protein 3, variant 1 | 201 | 202 | 49 ... 549 |
| M134 | HDAC2: histone deacetylase 2 | 205 | 206 | 205 ... 1671 |
| M674 | HN1: hematological and neurological expressed 1 | 209 | 210 | 104 ... 568 |
| M401 | HSCP1: serine carboxypeptidase 1 precursor protein | 219 | 220 | 33 ... 1391 |
| M402 | HSPD1: heat shock 60 kD protein 1 (chaperonin) | 223 | 224 | 25 ... 1746 |
| M139 | IGSF1: IGCD1, IGDC1, KIAA036, immunoglobulin superfamily, member 1 | 227 | 228 | 81 ... 4091 |
| M144 | KIAA1277: KIAA1277 protein | 251 | 252 | <5 ... 3079 |
| M145 | KIAA1361: KIAA1361 protein | 253 | 254 | <141 ... 3158 |
| M148 | LBP: lipopolysaccharide-binding protein | 259 | 260 | 18 ... 1463 |
| M558 | LOC118430: small breast epithelial mucin | 265 | 266 | 69 ... 341 |
| M406 | LOC51242: hypothetical protein LOC51242 | 267 | 268 | 1 ... 435 |
| M230 | LOC57402: S100-type calcium binding protein A14 | 269 | 270 | 99 ... 413 |
| M152 | MDS024: MDS024 protein | 273 | 274 | 65 ... 838 |
| M153 | ME1: malic enzyme 1, NADP(+)-dependent, cytosolic | 275 | 276 | 108 ... 1826 |
| M675 | MGC9753: hypothetical protein MGC9753 | 289 | 290 | 1092 ... 1814 |
| M156 | MIG: monokine induced by gamma interferon | 293 | 294 | 40 ... 417 |
| M157 | MLN64: steroidogenic acute regulatory protein related | 295 | 296 | 122 ... 1459 |
| M158 | MMP11: matrix metalloproteinase 11 preproprotein; stromelysin 3 | 297 | 298 | 23 ... 1489 |
| OV52 | MMP7: matrix metalloproteinase 7 (matrilysin, uterine) | 299 | 300 | 28 ... 831 |
| M407 | MS4A7: membrane-spanning 4-domains, subfamily A, member 7, variant 1 | 301 | 302 | 147 ... 869 |
| M150 | MSC: mitochondrial solute carrier, hypothetical protein PRO1278; HT015 protein | 304 | 305 | 368 ... 652 |
| M151 | MST4: serine/threonine protein kinase MASK | 306 | 307 | 118 ... 1368 |
| M159 | MTHFD2: methylene tetrahydrofolate dehydrogenase (NAD+ dependent), methenyltetrahydrofolate cyclohydrolase | 308 | 309 | 16 ... 1050 |
| M669 | MUC1: mucin 1, transmembrane | 310 | 311 | 74 ... 3841 |
| M233 | MYO5A: myosin VA (heavy polypeptide 12, myoxin) | 314 | 315 | 251 ... 5818 |
| M408 | NDRG1: N-myc downstream regulated protein | 323 | 324 | 111 ... 1295 |
| M165 | NPY1R: neuropeptide Y receptor Y1 | 329 | 330 | 209 ... 1363 |
| OV48 | OPN-a: Secreted phosphoprotein-1 (osteopontin, bone sialoprotein) | 335 | 336 | 1 ... 942 |
| OV49 | OPN-b: Secreted phosphoprotein-1 (osteopontin, bone sialoprotein) | 337 | 338 | 88 ... 990 |
| OV50 | OPN-c: Secreted phosphoprotein-1 (osteopontin, bone sialoprotein) | 339 | 340 | 1 ... 861 |
| M170 | PPARBP, PPAR binding protein, thyroid hormone receptor interactor 2; PPARG binding protein | 365 | 366 | 236 ... 4936 |
| M171 | PPIF: peptidylprolyl isomerase F (cyclophilin F), variant 1 | 367 | 368 | 72 ... 695 |
| M173 | PPIF: peptidylprolyl isomerase F (cyclophilin F), variant 3 | 370 | 371 | 84 ... 659 |
| M177 | PROML1: prominin (mouse)-like 1; hematopojetic stem cell antigen | 376 | 377 | 38 ... 2635 |
| M237 | PSMB3: proteasome (prosome, macropain) subunit, beta type, 3 | 378 | 379 | 18 ... 635 |
| M678 | PSMB9: proteasome (prosome, macropain) subunit, beta type, 9 (large multifunctional protease 2) | 380 | 381 | 41 ... 700 |
| M178 | PSMD3: proteasome (prosome, macropain) 26S subunit, non-ATPase, 3 | 382 | 383 | 158 ... 1762 |
| M180 | RAMP3: receptor (calcitonin) activity modifying protein 3 precursor; calcitonin receptor-like receptor activity modifying protein 3 | 392 | 393 | 30 ... 476 |

TABLE 9-continued

| Marker | Gene Name | SEQ ID NO (nts) | SEQ ID NO (AAs) | CDS |
|---|---|---|---|---|
| M679 | RARRES1: retinoic acid receptor responder (tazarotene induced) 1, variant 1 | 394 | 395 | 37...723 |
| M680 | RARRES1: retinoic acid receptor responder (tazarotene induced) 1, variant 2 | 396 | 397 | 128...1012 |
| M181 | RPL19: ribosomal protein L19 | 404 | 405 | 29...619 |
| M183 | S100A8: S100 calcium-binding protein A8 | 408 | 409 | 56...340 |
| M239 | SCD: stearoyl-CoA desaturase (delta-9-desaturase) | 410 | 411 | 236...1315 |
| M421 | SERHL: kraken-like, variant 1 | 416 | 417 | 118...1062 |
| M422 | SERHL: kraken-like, variant 2 | 418 | 419 | 82...693 |
| M185 | SLPI: secretory leukocyte protease inhibitor (antileukoproteinase), variant 1 | 429 | 430 | 19...417 |
| M681 | SLPI: secretory leukocyte protease inhibitor (antileukoproteinase), variant 2 | 431 | 430 | 23...421 |
| M424 | STAT4: signal transducer and activator of transcription 4, variant 1 | 436 | 437 | 82...1353 |
| M425 | STAT4: signal transducer and activator of transcription 4, variant 2 | 438 | 439 | 82...2328 |
| M187 | STC1: stanniocalcin 1 | 440 | 441 | 285...1028 |
| M191 | TLN1: talin 1 | 469 | 470 | 127...7752 |
| M234 | unnamed gene (3) | 479 | 480 | 55...676 |

TABLE 10

| Marker | Gene Name | SEQ ID NO (nts) | SEQ ID NO (AAs) | CDS |
|---|---|---|---|---|
| M553 | CLECSF1: C-type (calcium dependent, carbohydrate-recognition domain) lectin, superfamily member 1 (cartilage-derived), variant 2 | 56 | 57 | 3...673 |
| OV66 | CP: ceruloplasmin (ferroxidase), variant 3 | 79 | 80 | 1...3210 |
| M554 | DKFZP566I133: hypothetical protein DKFZp566I133, variant 2 | 113 | 114 | 134...1354 |
| M120 | FLJ12425: hypothetical protein FLJ12425 | 143 | 144 | 42...335 |
| M220 | GUCY1A3: guanylate cyclase 1, soluble, alpha 3, variant 1 | 193 | 194 | 520...2592 |
| M221 | GUCY1A3: guanylate cyclase 1, soluble, alpha 3, variant 2 | 195 | 194 | 386...2458 |
| M222 | GUCY1A3: guanylate cyclase 1, soluble, alpha 3, variant 3 | 196 | 194 | 407...2479 |
| M225 | HAG-3: anterior gradient protein 3, variant 2 | 203 | 204 | 116...129 |
| M405 | KIAA1077: KIAA1077 protein | 247 | 248 | 267...2882 |
| M236 | NY-BR-1.1: breast cancer antigen NY-BR-1.1 | 331 | 332 | 181...3858 |
| M173 | PPIF: peptidylprolyl isomerase F (cyclophilin F), variant 3 | 370 | 371 | 84...659 |
| M680 | RARRES1: retinoic acid receptor responder (tazarotene induced) 1, variant 2 | 396 | 397 | 128...1012 |
| M418 | RNB6: RNB6 protein, variant 2 | 402 | 403 | 125...1285 |
| M423 | SQLE: squalene epoxidase | 434 | 435 | 876...2600 |
| M424 | STAT4: signal transducer and activator of transcription 4, variant 1 | 436 | 437 | 82...1353 |
| M565 | SYTL2: synaptotagmin-like 2 | 446 | 447 | 261...1766 |
| M620 | TFAP2B: transcription factor AP-2 beta (activating enhancer binding protein 2 beta), variant 1 | 459 | 460 | 257...1639 |
| M621 | TFAP2B: transcription factor AP-2 beta (activating enhancer binding protein 2 beta), variant 2 | 461 | 462 | 257...1666 |
| M193 | unnamed gene (1) | 475 | 476 | 75...1697 |
| M194 | unnamed gene (2) | 477 | 478 | 23...1066 |
| M234 | unnamed gene (3) | 479 | 480 | 55...676 |
| M428 | unnamed gene (6), variant 1 | 485 | 486 | 75...2471 |
| M429 | unnamed gene (6), variant 2 | 487 | 488 | 75...1535 |
| M622 | unnamed gene (7) | 489 | 490 | 579à803 |
| M93 | unnamed gene (CASB619), variant 1 | 491 | 492 | 310...3351 |
| M94 | unnamed gene (CASB619), variant 2 | 493 | 494 | 310...3324 |

TABLE 11

| Marker | Gene Name | SEQ ID NO (nts) | SEQ ID NO (AAs) | CDS |
|---|---|---|---|---|
| M86 | AQP3: Aquaporin 3, variant 1 | 9 | 10 | 65...943 |
| M205 | COL12A1: collagen, type XII, alpha 1, variant 1 | 60 | 61 | 1...9192 |
| M618 | COL12A1: collagen, type XII, alpha 1, variant 2 | 62 | 63 | 114...9305 |
| M555 | DUSP4: dual specificity phosphatase 4 | 119 | 120 | 502...1686 |

TABLE 11-continued

| Marker | Gene Name | SEQ ID NO (nts) | SEQ ID NO (AAs) | CDS |
|---|---|---|---|---|
| M216 | GATA3: GATA-binding protein 3, variant 1 | 175 | 176 | 461...1792 |
| M217 | GATA3: GATA-binding protein 3, variant 2 | 177 | 176 | 461...1792 |
| M227 | KIAA0878: KIAA0878 protein | 241 | 242 | 336...2171 |
| M407 | MS4A7: membrane-spanning 4-domains, subfamily A, member 7, variant 1 | 301 | 302 | 147...869 |
| M561 | NDUFA8: NADH dehydrogenase (ubiquinone) 1 alpha subcomplex, 8 (19 kD, PGIV) | 325 | 326 | 68...586 |
| M421 | SERHL: kraken-like, variant 1 | 416 | 417 | 118...1062 |
| M619 | SIAH2: seven in absentia (Drosophila) homolog 2, variant 2 | 426 | 425 | 527...1501 |
| M568 | TFAP2A: transcription factor AP-2 alpha (activating enhancer-binding protein 2 alpha), variant 1 | 456 | 457 | 282...1601 |
| M569 | TFAP2A: transcription factor AP-2 alpha (activating enhancer-binding protein 2 alpha), variant 2 | 458 | 457 | 282...1601 |

TABLE 12

| Marker | Gene Name | SEQ ID NO (nts) | SEQ ID NO (AA) |
|---|---|---|---|
| M82 | AF245505, adlican mRNA, complete cds | 109 | 110 |
| M113 | ERBB2, v-erb-b2 avian erythroblastic leukemia viral oncogene homolog 2 (neuro/glioblastoma derived oncogene homolog); | 125 | 126 |
| M116 | FABP7, B-FABP, fatty acid binding protein 7, brain; | 131 | 132 |
| M130 | GNLY, granulysin, isoform NKG5 | 181 | 182 |
| M157 | MLN64, steroidogenic acute regulatory protein related | 295 | 296 |
| M170 | PPARBP, PPAR binding protein, thyroid hormone receptor interactor 2; PPARG binding protein | 365 | 366 |
| M171 | PPIF, peptidylprolyl isomerase F (cyclophilin F), variant 1 | 367 | 368 |
| M173 | PPIF, peptidylprolyl isomerase F (cyclophilin F), variant 3 | 370 | 371 |
| M180 | RAMP3, receptor (calcitonin) activity modifying protein 3 precursor; calcitonin receptor-like receptor activity modifying protein 3 | 392 | 393 |
| M183 | S100A8, S100 calcium-binding protein A8; 60B8AG | 408 | 409 |
| M185 | SLPI, secretory leukocyte protease inhibitor (antileukoproteinase) | 429 | 430 |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07705120B2). An electronic copy of the "Sequence Listing" will also be available from the USPTO upon request and payment of the fee set forth in 37 CFR 1.19(b)(3).

What is claimed:

1. An isolated polypeptide which is encoded by a nucleic acid molecule comprising a nucleotide sequence which is at least 95% identical to the entire nucleotide sequence of SEQ ID NO: 331.

2. The isolated polypeptide of claim 1, further comprising heterologous amino acid sequences.

3. An isolated fusion polypeptide comprising the polypeptide of claim 1 operably linked to a heterologous polypeptide.

4. The isolated polypeptide of claim 1, wherein the isolated polypeptide is encoded by a nucleic acid molecule comprising a nucleotide sequence which is at least 97% identical to the entire nucleotide sequence of SEQ ID NO: 331.

5. The isolated polypeptide of claim 1, wherein the isolated polypeptide is encoded by a nucleic acid molecule comprising a nucleotide sequence which is at least 98% identical to the entire nucleotide sequence of SEQ ID NO: 331.

6. The isolated polypeptide of claim 4, further comprising heterologous amino acid sequences.

7. An isolated fusion polypeptide comprising the polypeptide of claim 4 operably linked to a heterologous polypeptide.

8. The isolated polypeptide of claim 5, further comprising heterologous amino acid sequences.

9. An isolated fusion polypeptide comprising the polypeptide of claim 5 operably linked to a heterologous polypeptide.

10. An isolated polypeptide comprising an amino acid sequence which is at least 95% identical to the entire amino acid sequence of SEQ ID NO: 332.

11. The isolated polypeptide of claim 10, wherein the isolated polypeptide comprises an amino acid sequence which is at least 97% identical to the entire amino acid sequence of SEQ ID NO: 332.

12. The isolated polypeptide of claim 10, wherein the isolated polypeptide comprises an amino acid sequence which is at least 98% identical to the entire amino acid sequence of SEQ ID NO: 332.

13. The isolated polypeptide of claim 10, further comprising heterologous amino acid sequences.

14. An isolated fusion polypeptide comprising the polypeptide of claim 10 operably linked to a heterologous polypeptide.

15. The isolated polypeptide of claim 11, further comprising heterologous amino acid sequences.

16. An isolated fusion polypeptide comprising the polypeptide of claim 11 operably linked to a heterologous polypeptide.

17. The isolated polypeptide of claim 12, further comprising heterologous amino acid sequences.

18. An isolated fusion polypeptide comprising the polypeptide of claim 12 operably linked to a heterologous polypeptide.

19. An isolated polypeptide comprising the amino acid sequence of SEQ ID NO: 332.

20. The isolated polypeptide of claim 19, further comprising heterologous amino acid sequences.

21. An isolated fusion polypeptide comprising the polypeptide of claim 19 operably linked to a heterologous polypeptide.

22. An isolated polypeptide which is encoded by a nucleic acid molecule comprising the nucleotide sequence of SEQ ID NO: 331.

23. The isolated polypeptide of claim 22, further comprising heterologous amino acid sequences.

24. An isolated fusion polypeptide comprising the polypeptide of claim 22 operably linked to a heterologous polypeptide.

* * * * *